(12) United States Patent
Zhan et al.

(10) Patent No.: US 11,298,338 B2
(45) Date of Patent: Apr. 12, 2022

(54) COMPOSITIONS AND METHODS FOR CANCER THERAPY

(71) Applicant: UNIVERSITY OF IOWA RESEARCH FOUNDATION, Iowa City, IA (US)

(72) Inventors: Fenghuang Zhan, Iowa City, IA (US); Ivana Frech, Iowa City, IA (US); Guido Tricot, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 16/307,240

(22) PCT Filed: Jun. 6, 2017

(86) PCT No.: PCT/US2017/036146
§ 371 (c)(1),
(2) Date: Dec. 5, 2018

(87) PCT Pub. No.: WO2017/214140
PCT Pub. Date: Dec. 14, 2017

(65) Prior Publication Data
US 2019/0216771 A1 Jul. 18, 2019

Related U.S. Application Data

(60) Provisional application No. 62/447,293, filed on Jan. 17, 2017, provisional application No. 62/346,271, filed on Jun. 6, 2016.

(51) Int. Cl.
| | |
|---|---|
| *A61K 31/375* | (2006.01) |
| *A61K 31/198* | (2006.01) |
| *A61P 35/00* | (2006.01) |
| *A61K 31/381* | (2006.01) |
| *A61K 31/4184* | (2006.01) |
| *A61K 31/496* | (2006.01) |
| *A61K 31/5377* | (2006.01) |
| *A61K 9/00* | (2006.01) |
| *A61K 45/06* | (2006.01) |

(52) U.S. Cl.
CPC .......... *A61K 31/375* (2013.01); *A61K 9/0019* (2013.01); *A61K 31/198* (2013.01); *A61K 31/381* (2013.01); *A61K 31/4184* (2013.01); *A61K 31/496* (2013.01); *A61K 31/5377* (2013.01); *A61K 45/06* (2013.01); *A61P 35/00* (2018.01)

(58) Field of Classification Search
CPC ................ A61K 31/375; A61K 9/0019; A61K 31/5377; A61K 31/496; A61K 31/4184; A61K 31/381; A61K 45/06; A61K 31/198; A61P 35/00
See application file for complete search history.

(56) References Cited

U.S. PATENT DOCUMENTS

| | | |
|---|---|---|
| 9,238,070 B2 | 1/2016 | Gallatin et al. |
| 2009/0042845 A1 | 2/2009 | Aylor et al. |
| 2009/0274698 A1 | 11/2009 | Bhagwat et al. |
| 2018/0338935 A1* | 11/2018 | Glazier ............... A61K 31/198 |

FOREIGN PATENT DOCUMENTS

WO  2015191668 A1  12/2015

OTHER PUBLICATIONS

Heidi Fritz et al., IntraIntravenous Vitamin C and Cancer: A Systematic Review, Integrative Cancer Therapies 2014, vol. 13(4) 280-300 (Year: 2014).*
Berenson et al., Efficacy and safety of melphalan, arsenic trioxide and ascorbic acid combination therapy in patients with relapsed or refractory multiple myeloma: a prospective, multicentre, phase II, single-arm study, Br J Haematol. 2006;135:174-183 (Year: 2006).*
Salem et al., The road to cure in multiple myeloma starts with smoldering disease, Expert Opin Orphan Drugs. Apr. 12, 2015; 3(6): . doi:10.1517/21678707.2015.1036740 (Year: 2015).*
Banerjee, R , et al., "TRIP13 promotes error-prone nonhomologous end joining and induces chemoresistance in head and neck cancer", Nature Communications 5, 4527, 18 pages (2014).
Chauhan, D , et al., "A Small Molecule Inhibitor of Ubiquitin-Specific Protease-7 Induces Apoptosis in Multiple Myeloma Cells and Overcomes Bortezomib Resistance", Cancer Cell 22(3), 345-358 (2012).
Chen, Q , et al., "Pharmacologic doses of ascorbate act as a prooxidant and decrease growth of aggressive tumor xenografts in mice", PNAS 105(32), 11105-11109 (2008).
Creagan, E , et al., "Failure of high-dose vitamin C (ascorbic acid) therapy to benefit patients with advanced cancer. A controlled trial", N Engl J Med 301, 687-690 (1979).
Gao, M , et al., "Identification and Characterization of Tumor-Initiating Cells in Multiple Myeloma", JNCI: Journal of the National Cancer Institute, djz159, https://doi.org/10.1093/jnci/djz159, 50 pages, (published Aug. 12, 2019).
Gu, Z , et al., "Decreased Ferroportin Promotes Myeloma Cell Growth and Osteoclast Differentiation", Cancer Res 75 (11), 2211-2221 (2015).
Hernando, H , et al., "EZH2 Inhibition Blocks Multiple Myeloma Cell Growth through Upregulation of Epithelial Tumor Suppressor Genes", Molecular Cancers Therapeutics 15(2), 287-298 (2015).
Luo, J , et al., "Association between vitamin C intake and lung cancer: a dose-response meta-analysis", Sci Rep 4, 6161 (2014).
Moertel, C , et al., "High-Dose Vitamin C versus Placebo in the Treatment of Patients with Advanced Cancer Who Have Had No Prior Chemotherapy—A Randomized Double-Blind Comparison", N Engl J Med 312, 137-141 (1985).

(Continued)

*Primary Examiner* — Jason Deck
(74) *Attorney, Agent, or Firm* — Viksnins Harris Padys Malen LLP

(57) ABSTRACT

The invention provides compositions and methods to treat a hyperproliferative disorder with ascorbate or a pharmaceutically acceptable salt thereof, and one or more anti-cancer therapies.

8 Claims, 37 Drawing Sheets

(56) References Cited

OTHER PUBLICATIONS

Patent Cooperation Treaty, International Searching Authority, Search Report and Written Opinion for PCT/US2017/036146, 12 pages, dated Aug. 11, 2017.

Qazilbash, M, et al., "Arsenic Trioxide with Ascorbic Acid and High-Dose Melphalan: Results of a Phase II Randomized Trial", American Society for Blood and Marrow Transplantation 14, 1401-1407 (2008).

Riordan, H, et al., "Intravenous ascorbic acid: protocol for its application and use", Puerto Rico Health Sciences Journal 22(3), 287-290 (2003).

Xia, J, et al., "Multiple Myeloma Tumor Cells are Selectively Killed by Pharmacologically-dosed Ascorbic Acid", EBioMedicine 18, 41-49 (2017).

* cited by examiner

MULTIPLE MYELOMA (9, 69.2%), MGUS (2, 15.4%), SMOLDERING MYELOMA (2, 15.4%)

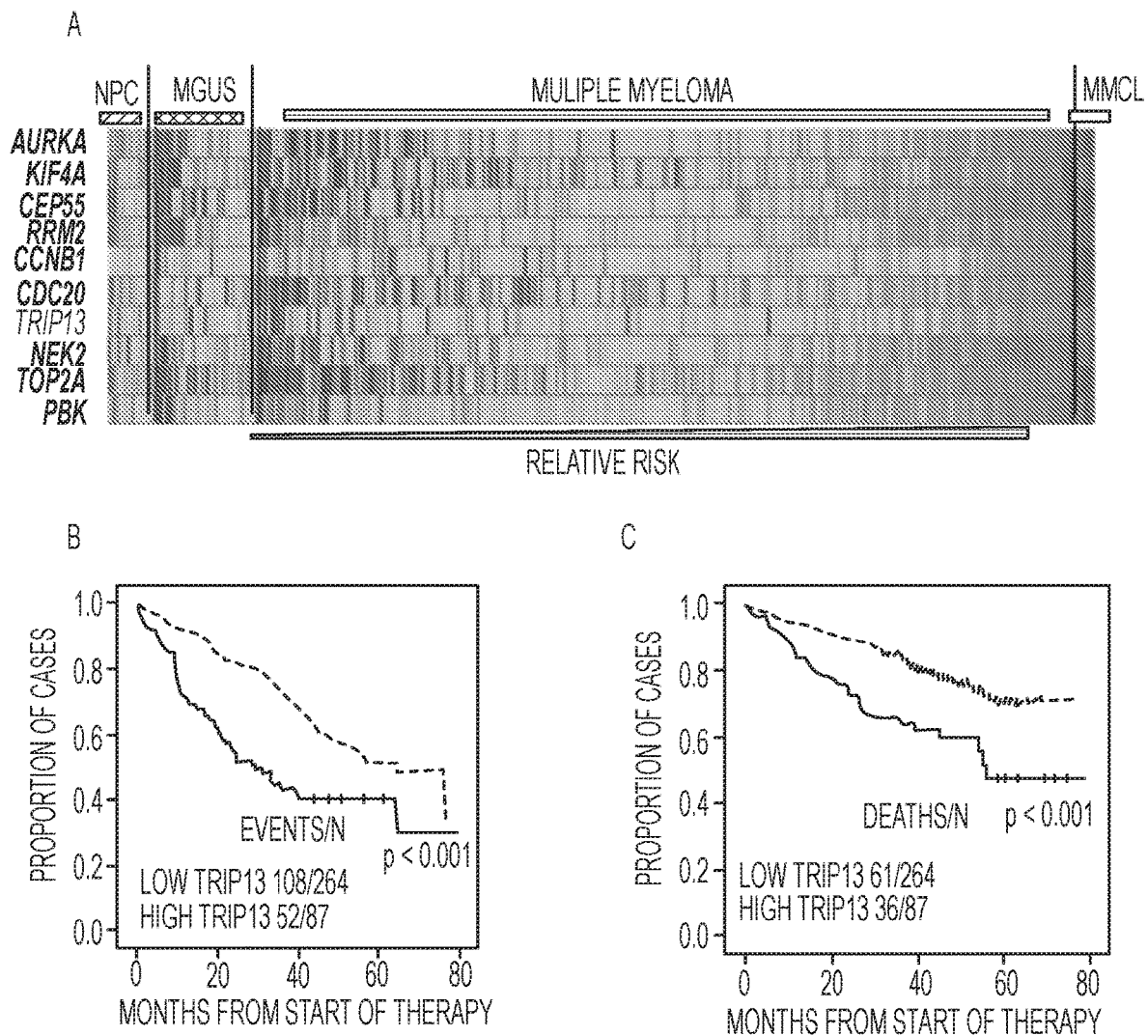
Figures 26A-C

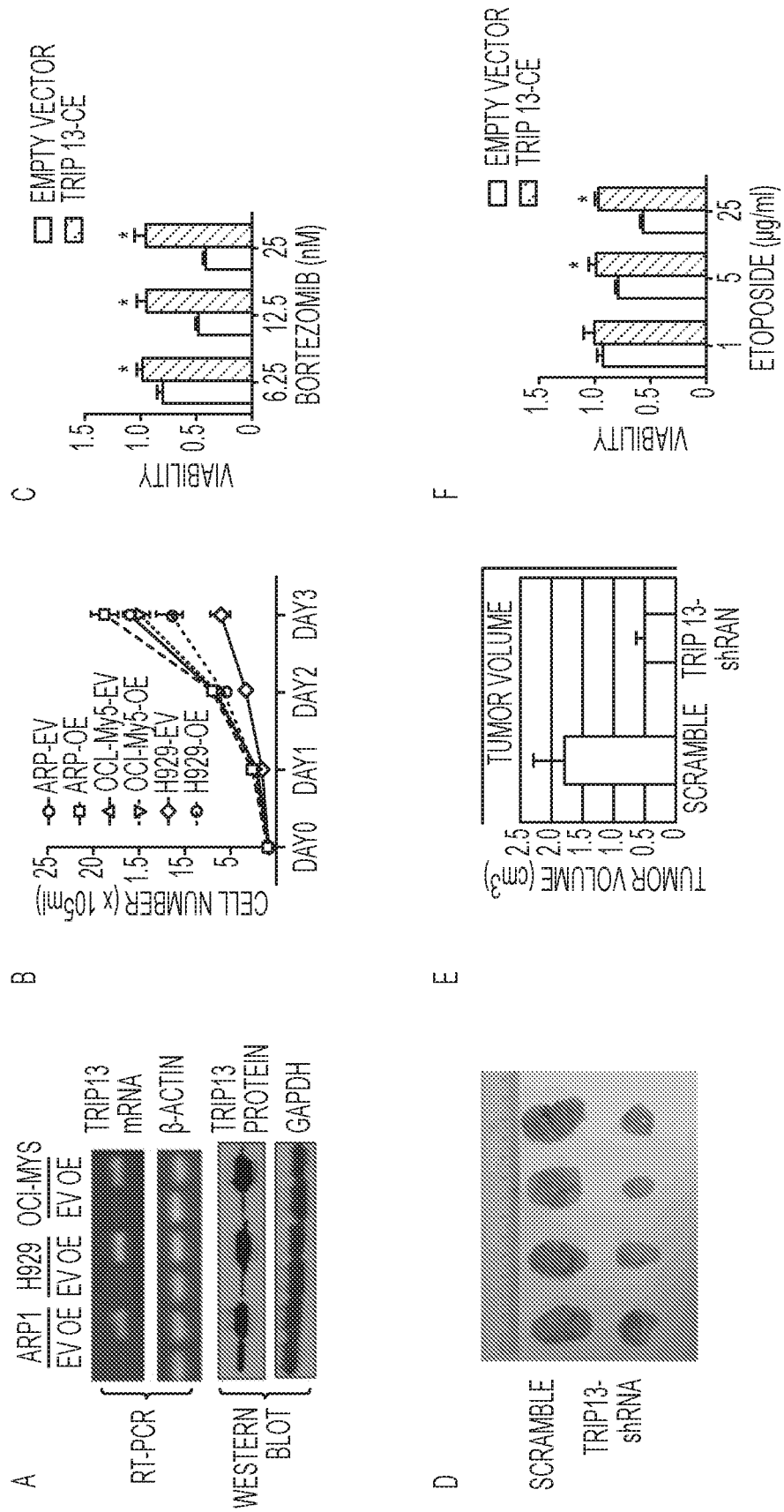
Figures 27A-F

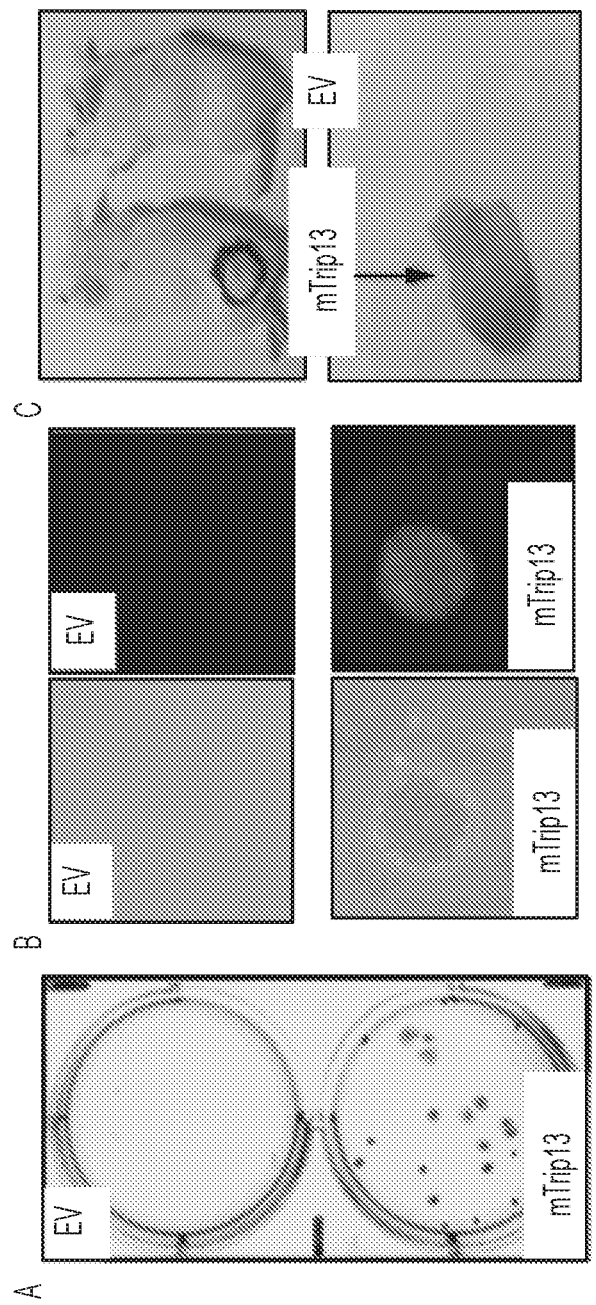
Figures 28A-C

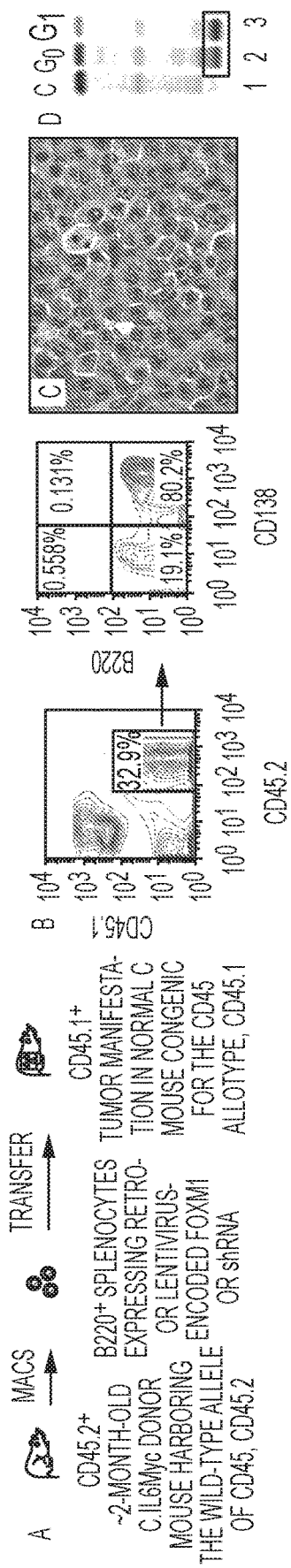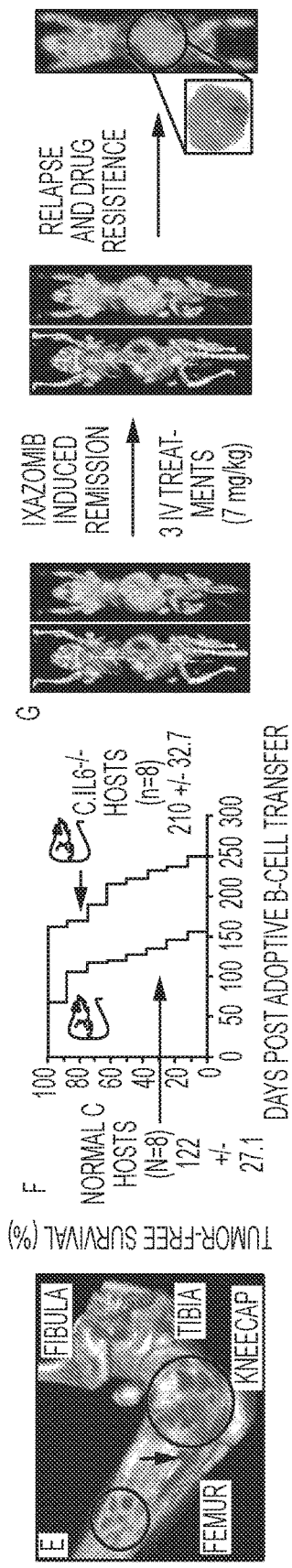
Figures 29A-G

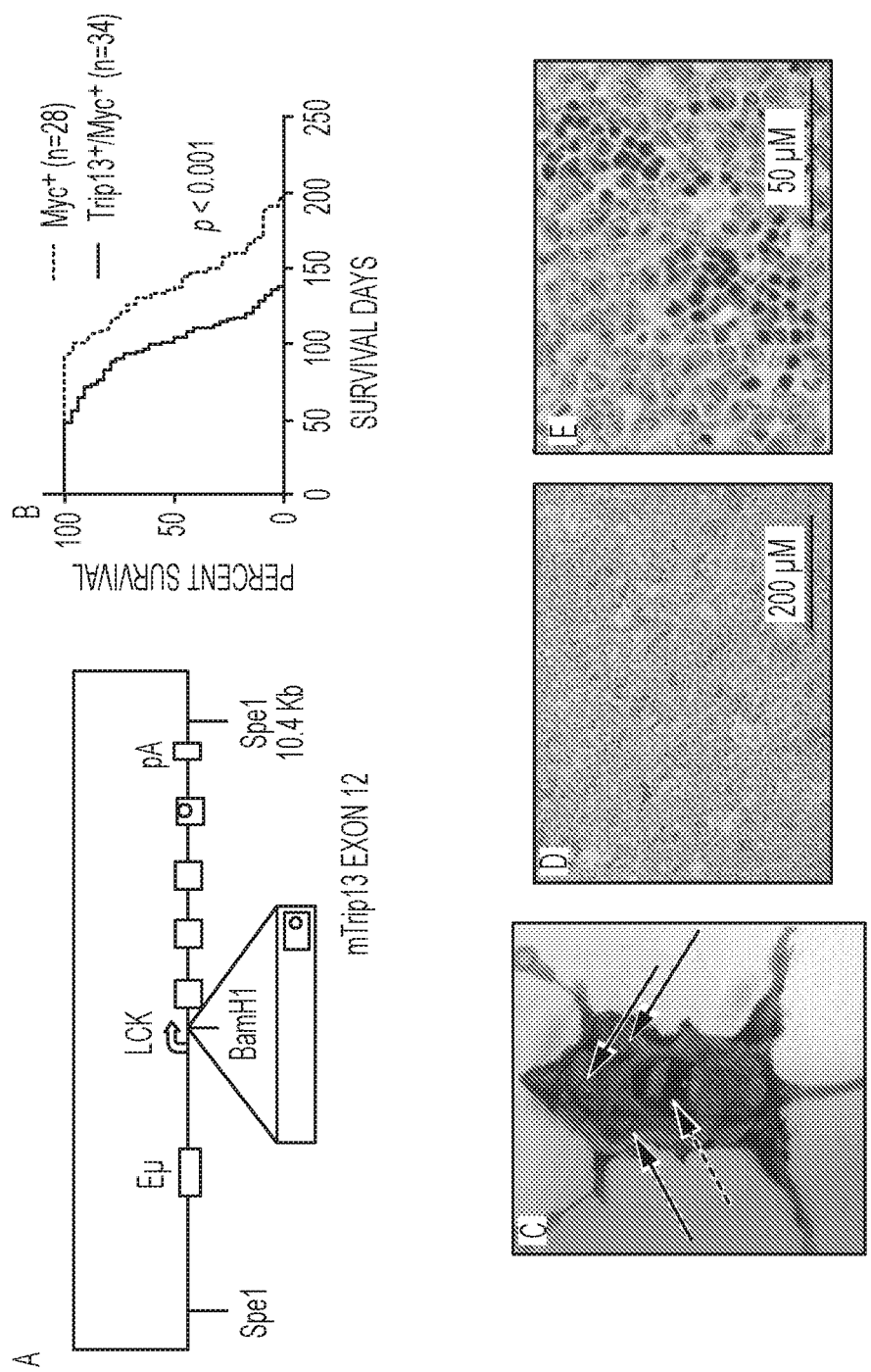
Figures 30A-E

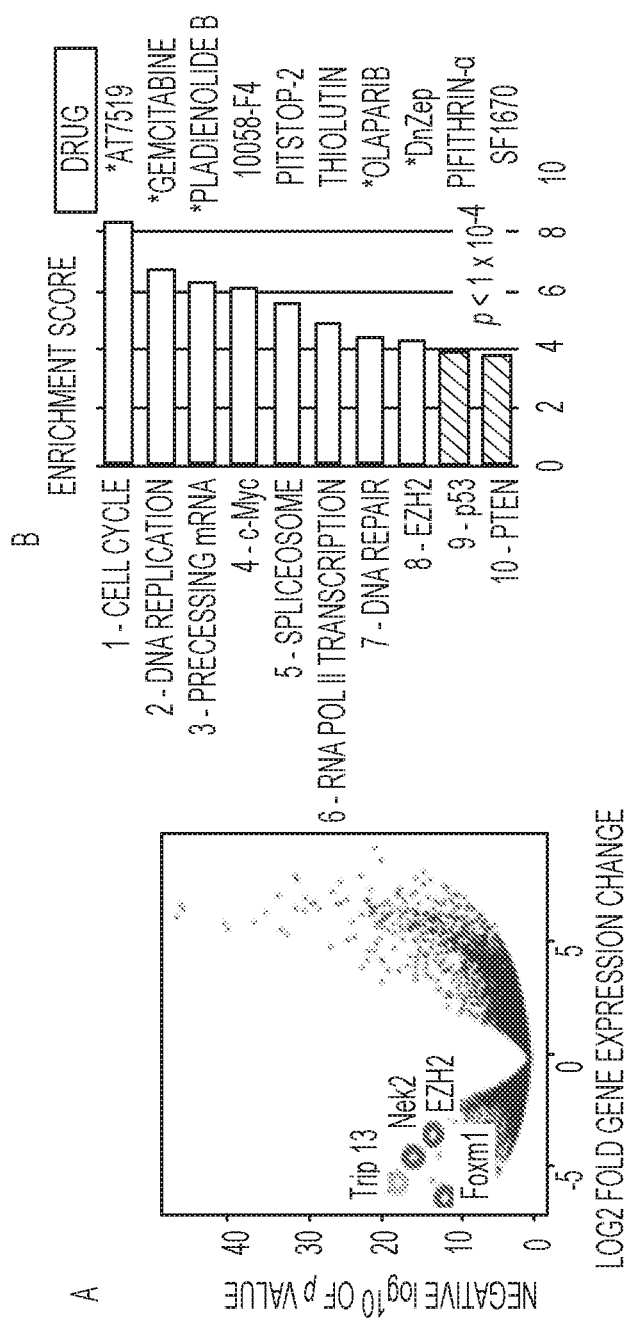
Figures 31A-B

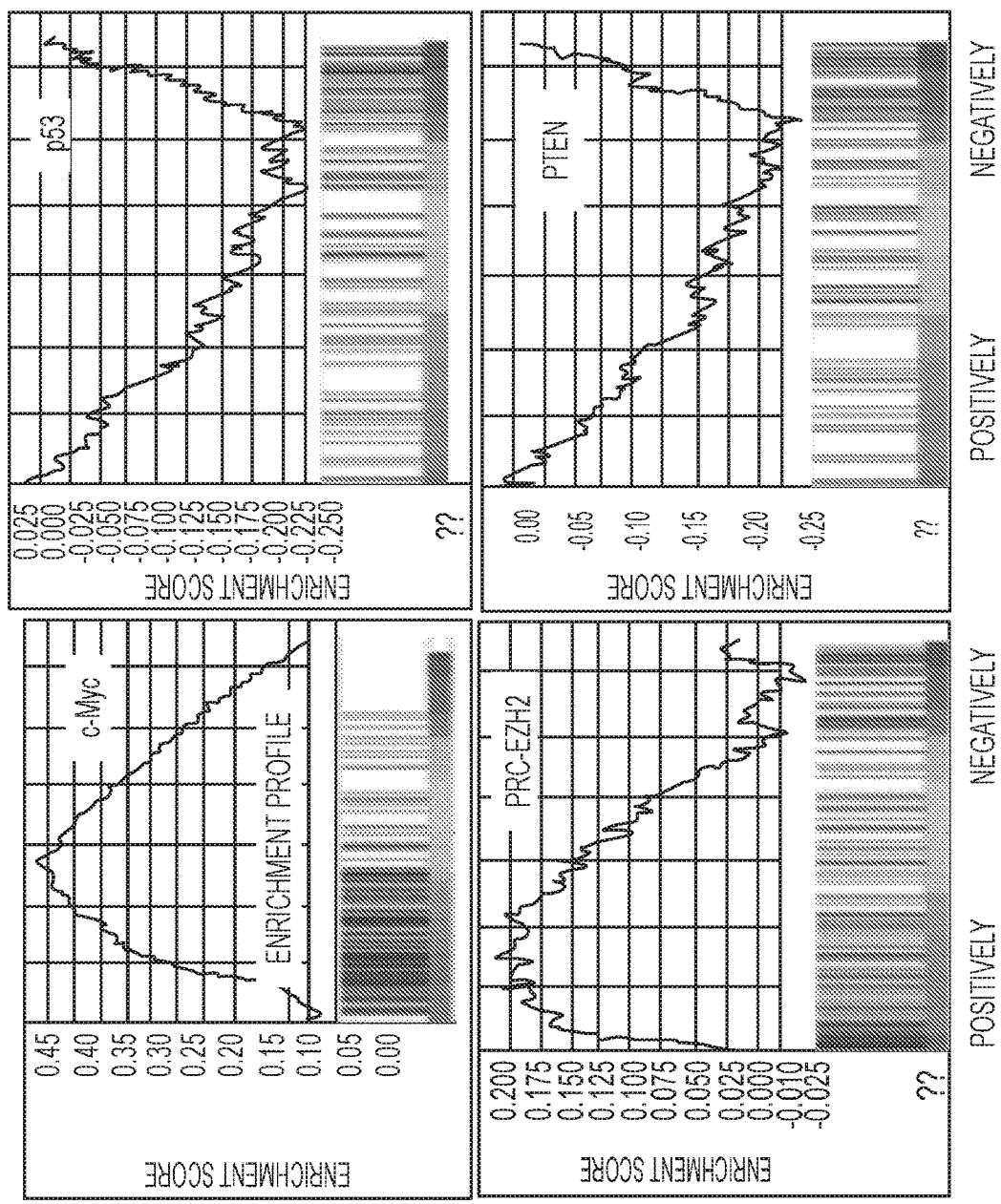
Figures 32A-B

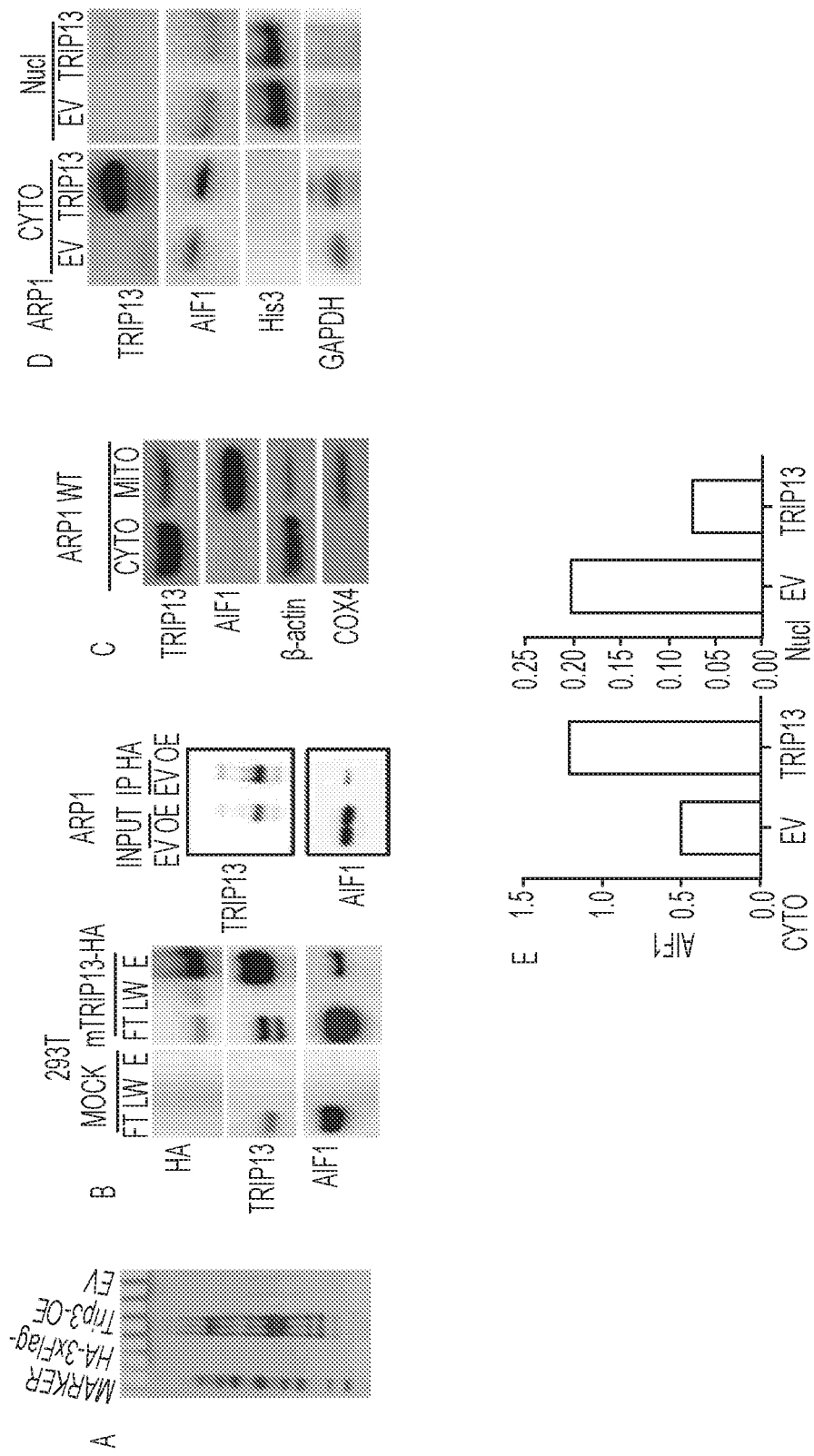
Figures 33A-E

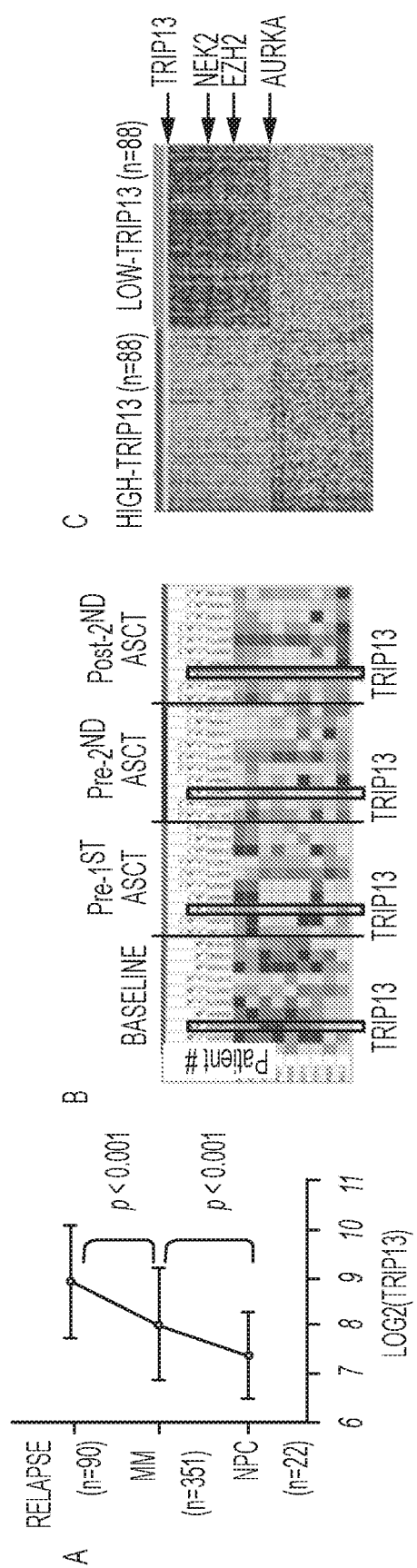
Figures 36A-C

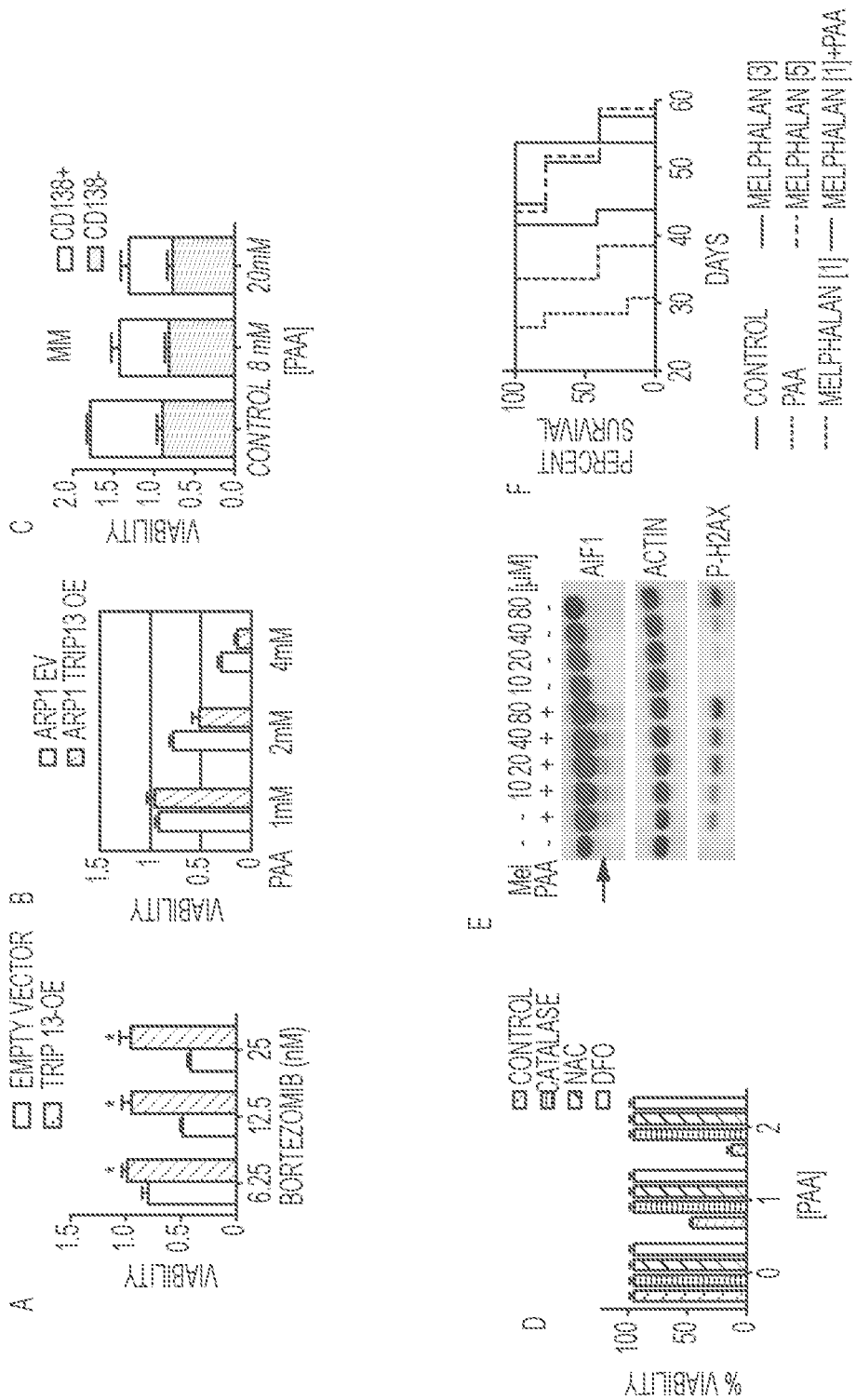
Figures 37A-F

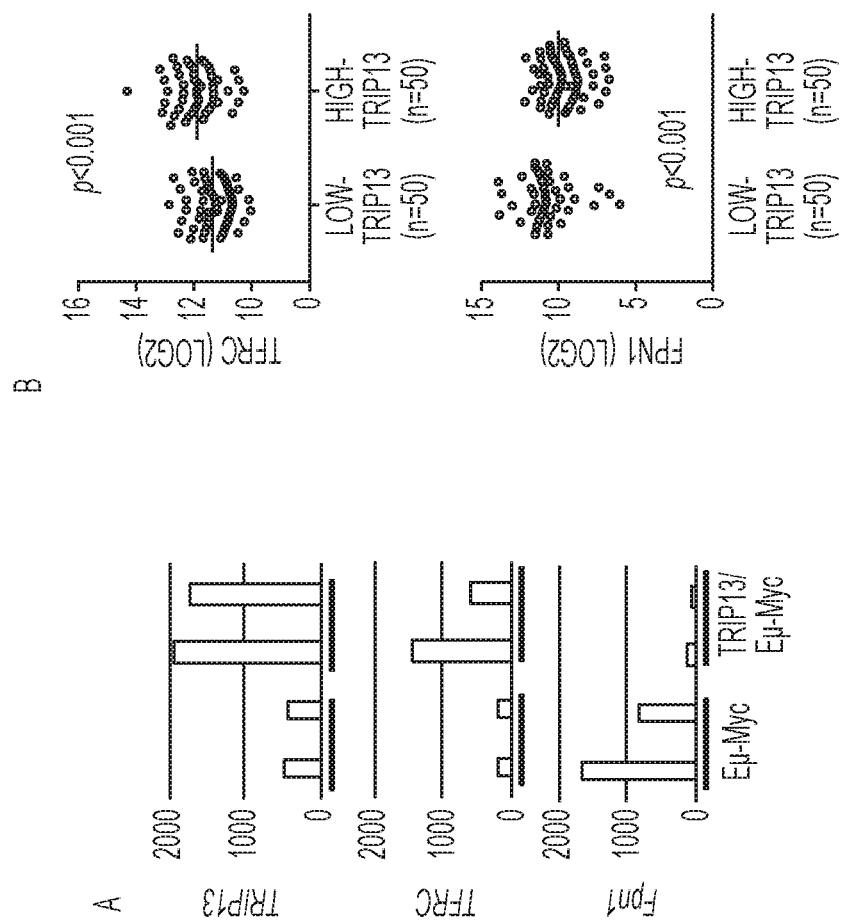
Figures 38A-B
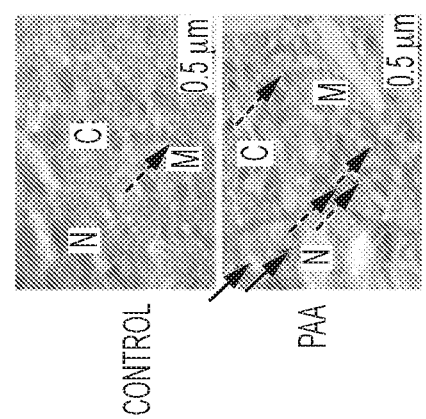
Figure 37G

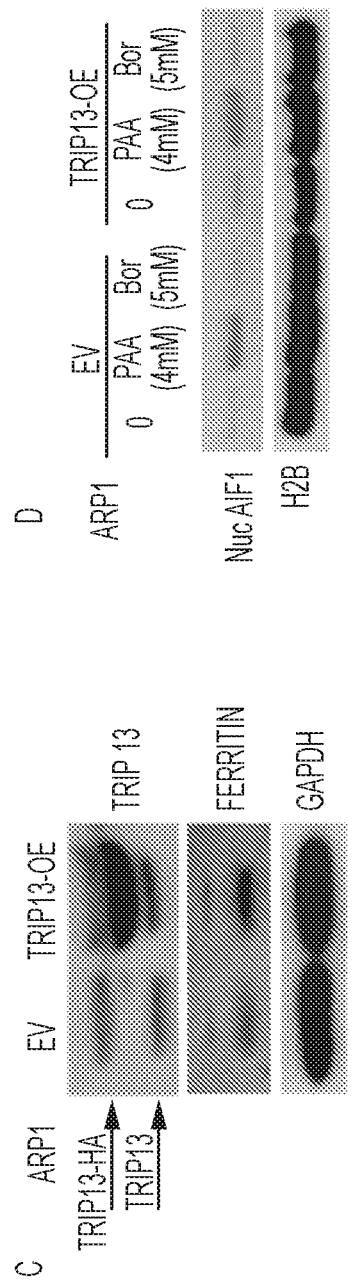
Figures 38C-D

COMPOSITIONS AND METHODS FOR CANCER THERAPY

RELATED APPLICATION

This application claims priority to U.S. Provisional Application No. 62/346,271 that was filed on Jun. 6, 2016, and U.S. Provisional Application No. 62/447,293 that was filed on Jan. 17, 2017. The entire content of the applications referenced above are hereby incorporated by reference.

BACKGROUND

Most treatment plans for patients with cancer include surgery, radiation therapy, and/or chemotherapy. Early clinical trials were performed for the use of vitamin C (ascorbic acid) to treat cancer. But epidemiological studies evaluating the association between the intake of vitamin C and cancer risk produced inconsistent results. (Luo, et al., Association between vitamin C intake and lung cancer: a dose-response meta-analysis, Sci Rep. 2014 Aug. 22; 4:6161). Other studies determined that no significant differences were noted between the ascorbate-treated and placebo-treated groups for symptoms, performance status, or survival (Moertel C G, Fleming T R, Creagan E T, Rubin J, O'Connell M J, Ames M M. High-dose vitamin C versus placebo in the treatment of patients with advanced cancer who have had no prior chemotherapy. A randomized double-blind comparison. N Engl J Med. 1985; 312(3):137-41; Creagan E T, Moertel C G, O'Fallon J R, Schutt A J, O'Connell M J, Rubin J, Frytak S. Failure of high-dose vitamin C (ascorbic acid) therapy to benefit patients with advanced cancer. A controlled trial. N Engl J Med. 1979; 301(13):687-90). There is a need for more efficacious cancer treatments with minimal side effects.

SUMMARY

The present invention provides in certain embodiments a method of treating a hyperproliferative disorder associated with high intracellular iron comprising administering pharmacological ascorbic acid (PAA) or a pharmaceutically acceptable salt thereof. As used herein the term "high iron" means that the intracellular free iron concentration is greater than the in a corresponding non-tumor cell.

The present invention provides in certain embodiments a method of reducing toxic effects of melphalan in a patient in need thereof comprising administering pharmacological ascorbic acid (PAA) or a pharmaceutically acceptable salt thereof.

The present invention provides in certain embodiments a method of treating multiple myeloma, including smoldering multiple myeloma, comprising administering pharmacological ascorbic acid (PAA) or a pharmaceutically acceptable salt thereof.

The present invention provides in certain embodiments a use of the combination of pharmacological ascorbic acid (PAA) or a pharmaceutically acceptable salt thereof and melphalan in the preparation of a medicament for the treatment of a hyperproliferative disorder in a mammal.

The present invention provides in certain embodiments a kit comprising pharmacological ascorbic acid (PAA) or a pharmaceutically acceptable salt thereof and melphalan, a container, and a package insert or label indicating the administration of the PAA and with melphalan for treating a hyperproliferative disorder.

The present invention provides in certain embodiments a product comprising pharmacological ascorbic acid (PAA) and melphalan as a combined preparation for separate, simultaneous or sequential use in the treatment of a hyperproliferative disorder.

The present invention provides in certain embodiments a therapeutic composition comprising a combination of (a) pharmacological ascorbic acid (PAA) or a pharmaceutically acceptable salt thereof; and (b) an alkylating agent. In certain embodiments, the therapeutic composition lacks a chelator, such as ethylene diamine tetraacetic acid (EDTA).

The present invention provides in certain embodiments, a method of administering to a mammalian cell having down-regulated expression of Ferroportin 1 (Fpn1) as compared with its normal counterpart cell an expression-modulating agent, comprising contacting the mammalian cell with pharmacological ascorbic acid (PAA) or a pharmaceutically acceptable salt thereof.

The present invention provides in certain embodiments, a method of administering to a mammalian cell having upregulated expression of enhancer of zeste 2 (EZH2) as compared with its normal counterpart cell an expression-modulating agent, comprising contacting the mammalian cell with an inhibitor of EZH2.

The present invention provides in certain embodiments, a method of administering to a mammalian cell having upregulated expression of Thyroid Hormone Receptor Interactor Protein 13 (TRIP13) as compared with its normal counterpart cell an expression-modulating agent, comprising contacting the mammalian cell with pharmacological ascorbic acid (PAA) or a pharmaceutically acceptable salt thereof and/or with an inhibitor of TRIP13.

BRIEF DESCRIPTION OF THE DRAWINGS

(FIG. 1A) CD138+ tumor cells and CD138− non-tumor cells were treated with either PAA (1, 2, 4, 8, 20 mM) or PBS (control) from MM patients and (FIG. 1B) and (FIG. 1C) respectively from SMM and MGUS patients. (FIG. 1D) Xenografted NOD.Cγ-Rag1 mice were treated with PAA and in combination or not with melphalan, carfizomib and bortezomib. After one-week injection of ARP1 cells, mice were treated with either PAA (4 mg/kg) injected intraperitoneal once a day, 5 days every week for 3 weeks. Melphalan (3 mg/kg) was injected intraperitoneal once a day, 2 days a week for 3 weeks. Carfizomib (3 mg/kg) was injected by in vein once a day, 2 days every week for 3 weeks. Total flux indicates quantification of luciferase intensity (tumor burden) of mice pre- and post-PAA treatment at different time points. (FIGS. 1E & FIG. 1F) Tumor burden was analyzed in ARP1 NOD.Cγ-Rag1 mice treated with PAA and with or without different doses of melphalan (1, 3, 5 mg/kg). (FIG. 1G) Treatment-related survival curve of mice. The log-rank test was performed and indicated that mouse survivals among these groups are significantly different ($p<0.001$) and PAA when combined with low dose of melphalan extends MM mouse survival.

(FIG. 2A) OCI-MY5 WT cells were incubated with or without catalase (100 U/ml), NAC (15 mM) or DFO (200 µM) for 3 hrs following treatment with PAA. PAA was washed away after 1 hr treatment and cell viability was determined 24 hrs later. (FIG. 2B) OCI-MY5 EV and OCI-MY5 OE-Fpn1 were treated with or without PAA (0-20 mM). PAA was washed away after 1 hr and cell viability was measured 24 hrs later. OCI-MY5 EV (FIG. 2C) and OCI-MY5 OE-Fpn1 (FIG. 2D) were incubated with or without iron (Fe-NTA (FE), 100 μM). After 18 hrs cells were treated with or without DFO (200 μM) for 3 hrs followed by PAA treatment for 1 hr and cell viability was measured as described in FIG. 2A.

(FIG. 3A) Transmission electron microscopy of OCI-MY5 WT cells treated with or without PAA (4 mM). After 1 hr incubation, PAA was washed away and cells were fixed for TEM after 60 min and 120 min. Red boxes represent zooming image of mitochondria in OCI-MY5 WT cells (left) and OCI-MY5 WT cells treated with PA (right). (FIG. 3B) OCI-MY5 WT cells were treated with or without PAA. After 1 hr, PAA was washed away and cells were lysed at the specified times and RIP1, RIP3, Caspase 3, Caspase 8, Caspase 9, and β-actin levels were examined by western blots.

(FIG. 4A) Top bar graph represents OCI-MY5 shRNA-Scramble and shRNA-AIF1 cells incubated with doxycycline to knockdown AIF1 for 2 days. Bottom bar graph represents OCI-MY5 EV and OCI-MY5 OE-AIF1 cells. All cells were treated without or with PAA at the specified concentrations. After 1 hr treatment, PAA was washed away and cells viability was measured after 24 hrs. Knockdown and overexpression of AIF1 was confirmed by western blots. (FIG. 4B) Schematic representation of PAA inducing AIF1 cleavage, release and nuclear translocation in MM tumor cells. (FIG. 4C) OCI-MY5 WT cells with or without PAA. After 1 hr PAA was washed away and cells were incubated with melphalan (Mel, 0-80 μM) for 4 hrs then lysed. AIF1, β-actin and γ-H2AX levels were analyzed by western blots. (FIG. 4D) OCI-MY5 WT cells were incubated with or without DFO (200 μM) for 3 hrs followed PAA (2 mM) treatment. After 1 hr PAA was washed away and cells were lysed. AIF1 and β-actin levels were analyzed by western blots. (FIG. 4E) Electron microscope shows AIF1 immunolabeling staining of OCI-MY5 WT cells treated without (left) or with (right) PAA (2 mM). N, M, C respectively represent nucleus, mitochondria and cytoplasm. Blue arrows indicate the nuclear membrane and red arrowheads indicate AIF1 gold beads in cytoplasm or mitochondria. Black arrowheads indicate AIF1 gold beads in nuclei.

(FIG. 9A) OCI-MY5 EV and OE cells were incubated with or without BCS (10 μM) for 3 hrs following PAA treatment (4 mM). PAA was washed away after 1 hr and cell viability was determined 24 hrs later. (FIG. 9B) Total RNA was extracted from OCI-MY5 EV and OE cells and Fpn1 mRNA was analyzed by Real time RT-PCR.

(FIGS. 12A-B) Survival analysis were performed based on Fpn1 expression in different cohorts. The EFS (FIG. 12A) and OS (FIG. 12B) were performed in the TT2 cohort.

(FIG. 14A) Kaplan-Meier showed the survival curves, and pvalue was analyzed by the logrank test. (FIG. 14B) tumor burden was measured by the ELISA assay, and the significance ($p<0.0001$) was determined by one-way ANOVA.

FIG. 19A. Affymetrix signal of Fpn1 and EZH2 in normal plasma cells (NPCs), newly diagnosed multiple myeloma (MM; TT2 cohort) and low and high risk. $p<0.0001$ among these four groups. FIG. 19B.

Putative binding site of EZH2 on Fpn1 promoter. Promoter was analyzed using whole genome association study (GWAS).

Figure 20:
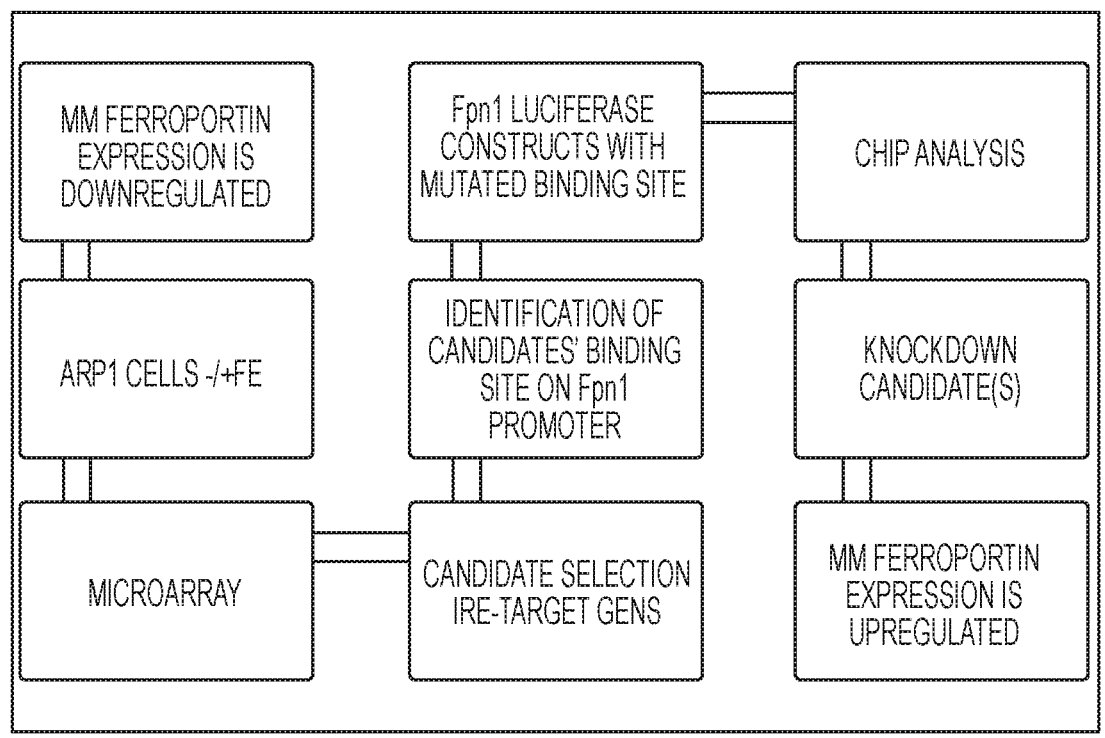

FIG. 20. Schematic flow for the identification of candidates Fpn1 repressor in MM.

Figure 21:
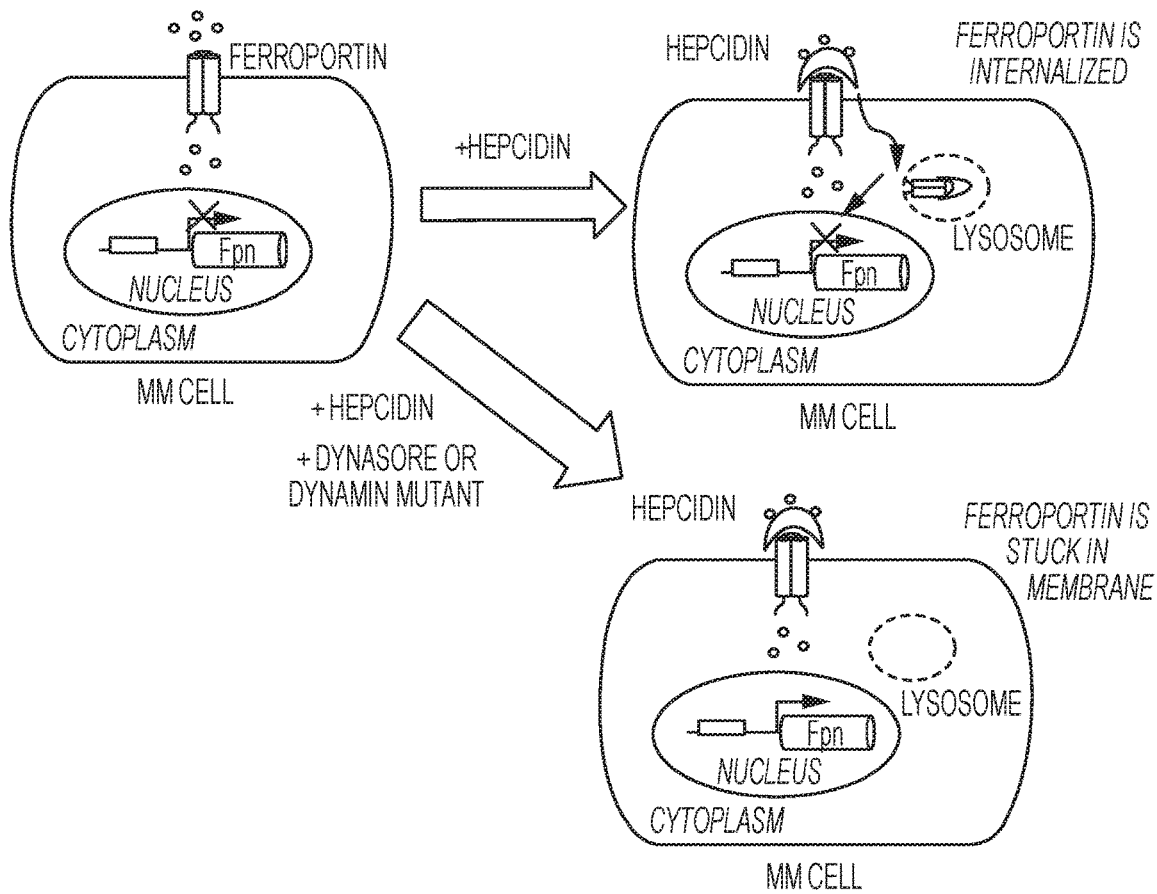

FIG. 21. Model for Hepcidin-Mediated Ferroportin 1 Internalization, Degradation and Transcriptional Repression.

Figure 22:
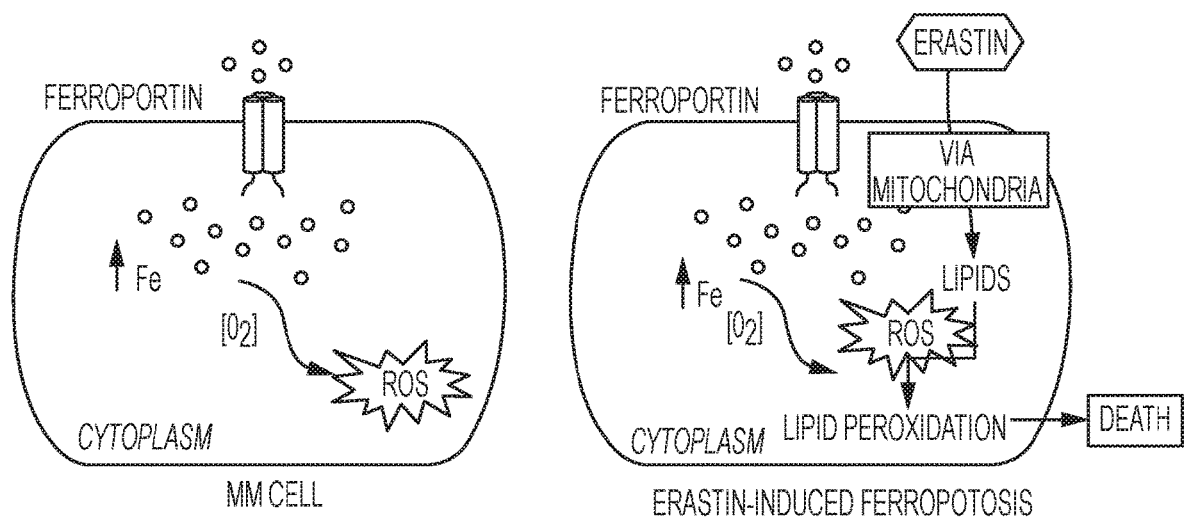

FIG. 22. Induction of Ferroptosis in MM Cells by Erastin. Erastin blocks, via mitochondria, the cell's antioxidative defenses and ultimately leads to an irondependent, oxidative cell death.

Figure 23:
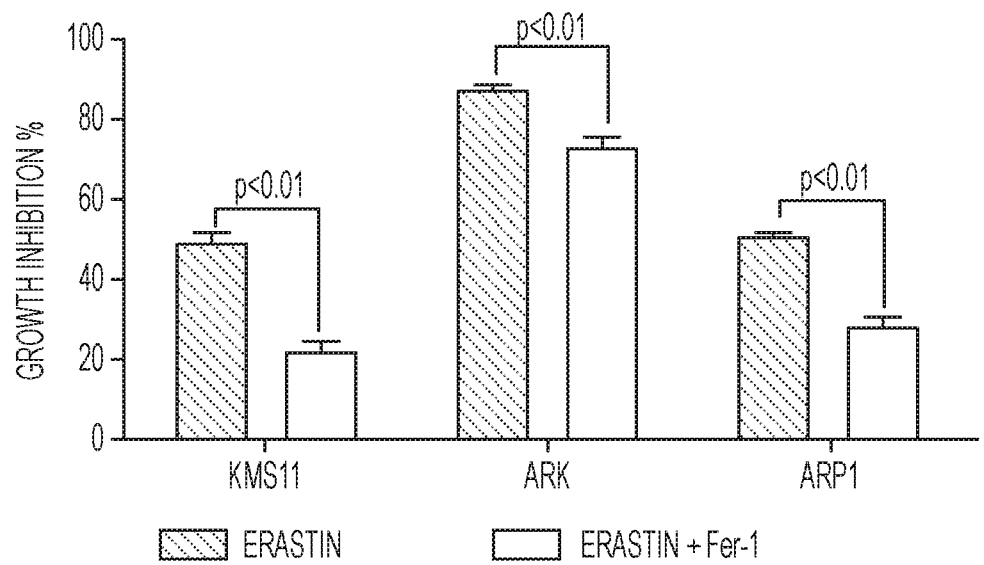

FIG. 23. Erastin Inhibits MM Cells Growth. KMS11, ARK and ARP1 cells were treated with 10 µM Erastin with or without ferrostatin (Fer-1) at 1 µM for 48 hours. Cell proliferation was measured by PrestoBlue assay and normalized to control cells to calculated growth inhibition.

Figure 24:
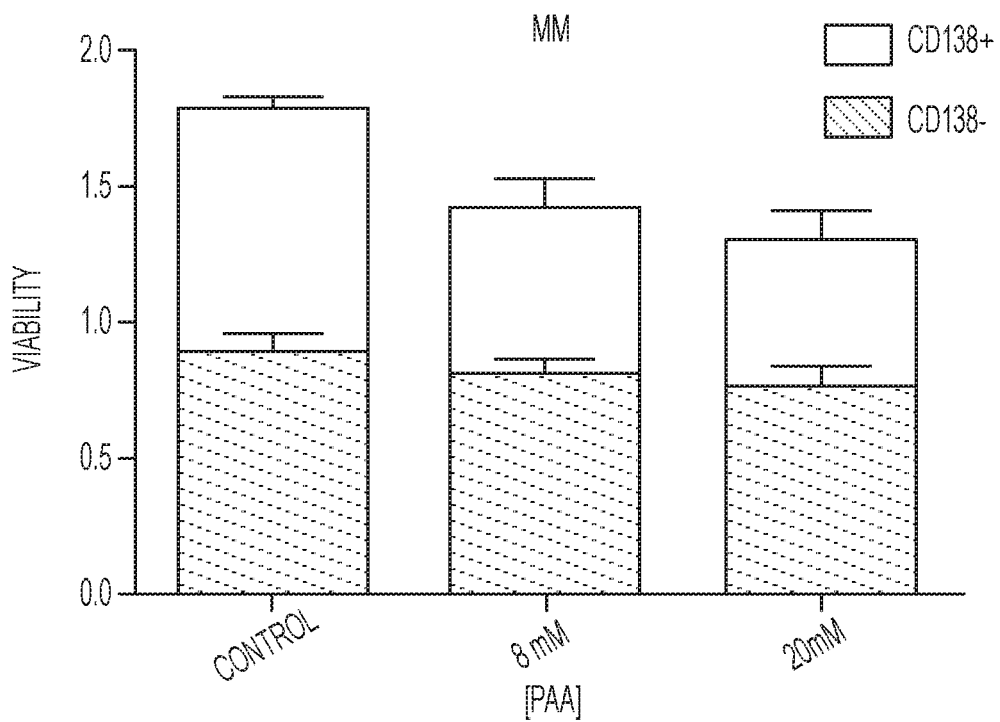

FIG. 24: Pharmacological Ascorbic Acid Selectively Kills MM Tumor Cells. CD138+ tumor cells and CD138− non-tumor cells from MM patients were treated with either PAA (8, 20 mM) or PBS (control) and cell viability was analyzed after 24 hours.

Figure 25:
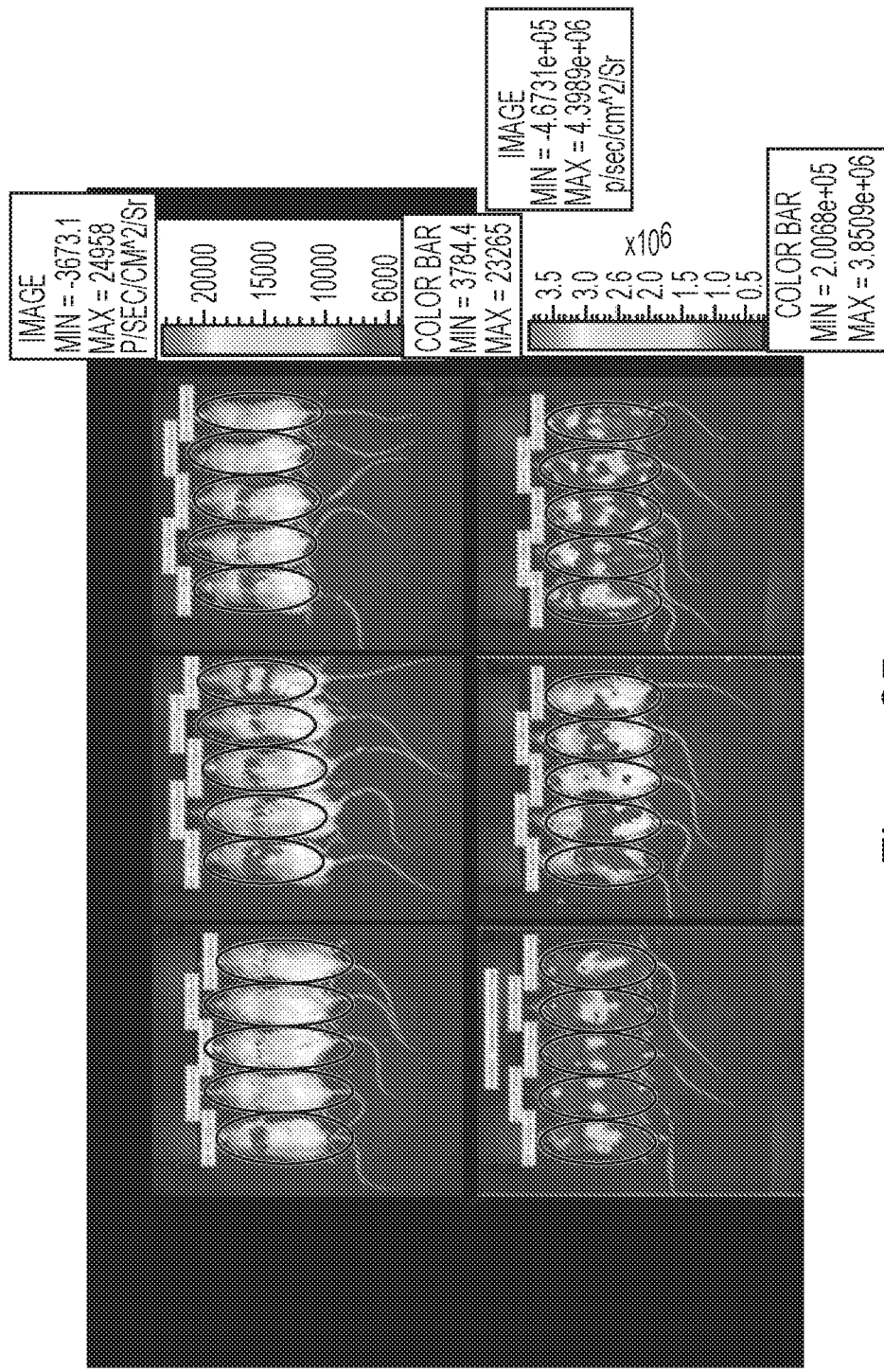

FIG. 25. Pharmacological Ascorbic Acid Anti-Cancer Activity is Iron-Dependent. Xenografted NOD.Cγ-Rag1 mice were injected with ARP1 cells. After one-week, mice were treated with either PAA (4 mg/kg) injected intraperitoneal once a day, PAA and in combination or not with DFO (100 mg/Kg, twice a week, intraperitoneal) and DFO alone. Total flux indicates quantification of luciferase intensity (tumor burden) of mice before (top panel) and after treatment (bottom panel).

FIGS. 26A-26C. TRIP13 expression is increased in a subset of newly diagnosed MM samples which link to a poor prognosis by GEP. (A) The heatmap presents the expression of TRIP13 and other 9 CIN genes related to MM drug resistance in 22 healthy subjects (NPC), 44 subjects with MGUS, 351 patients with newly diagnosed MM and 9 human MM cells lines (MMCL). Note: blue and pink (red) colors represent lower or higher median expression across all samples respectively. (B & C) High TRIP13 expression is linked to a poor prognosis in myeloma. Kaplan-Meier analyses of event-free survival (B) and overall survival (C) revealed inferior outcomes from 351 cases in the TT2 trial.

FIGS. 27A-27F. Increased TRIP13 induces MM cell proliferation and drug resistance. (A) The expression of TRIP13 mRNA and proteins is increased in MM cell lines ARP1, H929 and OCI-MY5 with TRIP13 overexpression (OE) compared to the control cells (EV). (B) Cell proliferation of ARP1, OCI-MY5 and H929 with TRIP13-OE as well as their counterparts transfected with empty vectors (EV) were counted for 3 consecutive days (p<0.05). (C & D) Knockdown of TRIP13 (shRNA) inhibits MM cell growth compared to the control (Scramble) in a xenograft mouse model using ARP1 MM cells (C) and quantified (D). (E & F) Cell viabilities of ARP1 cells with TRIP13-OE or EV were counted with indicated concentrations of Bortezomib (E) or Etoposide (F) after 24 h.

FIGS. 28A-28C. TRIP13 is an oncogene. (A) NIH3T3 cells transfected with empty vector (EV) or mouse TRIP13 (mTRIP13) were assessed by anchorage-independent colony formations in soft agar. (B) Images of NIH3T3 cells transfected with EV or mTRIP13 were shown in soft agar under microscope with bright field and green fluorescence (×4). (C) NIH3T3 cells transfected with EV or mTRIP13 were subcutaneously injected into NOD Rag1$^{null}$ mice and assessed for tumor formation at day 15.

FIGS. 29A-29F. Overview of the principal experimental model system used for the studies in Aim 1A. (A) Schematic illustration of adoptive B cell transfer from young, tumor-free CD45.2$^+$ C.IL6iMyc mice. B cells are isolated (left), and genetically modified in vitro (center), and transferred to sub-lethally irradiated (4Gy) C.CD45.1$^+$ congenic mice. (B) Flow cytometry contour plots 138 days post B-cell transfer, indicating the presence of CD45.2$^+$CD138$^+$ plasma cell tumors (PCT) in the bone marrow of a CD45.1$^+$ Balb/c (designated 'C') mouse. (C) Histopathology of a representative CD45.2$^+$ tumor (from a lymph node in this case) from a CD45.1$^+$ C mouse (H & E; 63×). (D) Tumor propagation in vivo. Shown is a serum electropherogram containing the M-spike of a mouse harboring a primary (G0) CD45.2$^+$ PCT (lane 2) and the same M-spike (red box) from a 'C' mouse 5 weeks after transfer of one million tumor cells (lane 3). A serum sample from a normal 'C' mouse was included as control (lane 1). (E) µCT analysis of the femur of a tumor-bearing mouse. Many osteolytic lesions generating a moth-eaten pattern are striking. (F) Kaplan-Meier curve indicating the survival advantage (p<0.001, log-rank test) of IL-6 knockout mice (IL-6$^{-/-}$; 210 days median tumor onset) compared to normal 'C' mice (122 days), both reconstituted with Myc-transgenic CD45.2$^+$ B cells.

FIGS. 30A-30B. TRIP13 enhances tumor development. (A) The construct of p1026× vector including a LCK promoter and Eµ enhancer (red * are stop codons of TRIP13 and human growth hormone gene (HGx). (B) The double transgenic TRIP13/Eµ-Myc mice show a short survival compared to Eµ-Myc mice. (C) An example of enlarged spleen (yellow arrow) and lymph nodes (red arrows) from a representative Tg TRIP13/Eµ-Myc mouse. (D & E) Histopathology of a representative tumor (from a lymph node in this case) from a Tg TRIP13/Eµ-Myc mouse (H & E).

FIGS. 31A-31C Preliminary analysis of the TRIP13 network in pre-malignant B cells from Tg TRIP13/Eµ-Myc mice and Eµ-Myc mice. (A) Volcano plot indicating the magnitude (abscissa) and statistical significance (ordinate) of the expression changes seen in 1,900 genes from RNA-seq of B cells from two types of transgenic mice (p<0.001). (B) GSEA of B cells using RNA-seq that distinguishes Tg TRIP13/Eµ-Myc mice from Tg Eµ-Myc mice as input. The 10 most significant pathways are presented rank ordered in accordance with the corresponding pathway scores. The inhibitors or activators listed in the right side are corresponding to the pathways with the references from #1~#10. * means the inhibitor is used in clinical trials. #9 (p53) and #10 (PTEN) pathways are negatively correlated with TRIP13 expression (see FIG. 32). (C) Strategy for identifying TRIP13 oncogenic signaling pathways.

FIGS. 32A-32B. Multiple pathways are enriched in transgenic TRIP13 pre-malignant B cells. (A) Bar views show TRIP13 expression in B cells collected at 6 weeks Tg TRIP13/Eµ-Myc mice and Eµ-Myc mice. (B) GSEAs show the c-Myc, EZH2, p53 and PTEN pathways are dysregulated by TRIP13.

FIGS. 33A-33E. TRIP13 binds and interacts with AIF1. (A) HEK293 cells is used to construct with stable expression of TRIP13 tagged with HA and 3×FLAG; TRIP13 binding proteins are pulled down by HA antibodies and then by FLAG antibodies for mass spectrometry analysis. (B) Co-immunoprecipitation using HA antibodies to pull-down TRIP13 binding proteins is performed, and western blots show the binding of AIF1 and TRIP13 proteins in 293T and MM cell line ARP1. (C) Fractionation and western blots show TRIP13 expresses in both cytoplasm and mitochondria; AIF1 expresses in mitochondrial. (D) Western blots show expression of AIF1 in TRIP13-OE ARP1 cells. (E) Quantification of AIF1 protein expression from (D) in cytoplasm and nucleus of TRIP13-OE ARP1 cells.

Figure 34:
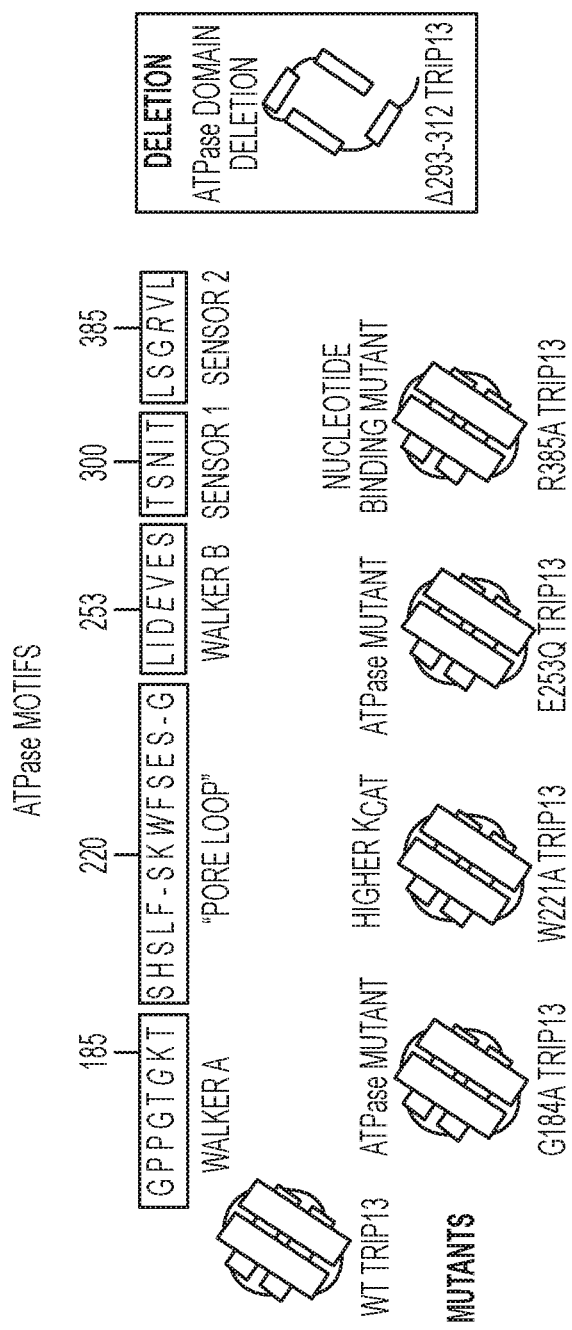

FIG. 34. TRIP13 contains conserved AAA⁻ sequence motifs. Schematic representation of ATPase motifs in TRIP13 and their mutants. ATPase mutants will be generated by single amino acid change in Walker A (G184A) and B (E253Q). Nucleotide binding (R385A) and catalytic (W221A) mutants will be generated by single amino acid substitution in the Pore Loop and Sensor 2 motifs. A deletion lacking of the ATPase domain including Sensor 1 motif will be generated.

Figure 35:

FIG. 35. MM treatment schema at the U of Iowa. D-PACE: Dexamethasone with infusion of cisplatin, doxorubicin, cyclophosphamide, and etoposide. Arrows indicate time points for laboratory investigations. Tx: transplantation.

FIGS. 36A-36C. Increased TRIP13 links to drug resistance in primary MM samples. (A) TRIP13 expression is upregulated in MM cells derived at diagnosis and relapse compared to normal plasma cells (NPC). GEP was performed in plasma cells from 22 normal donors, 351 newly diagnosed MMs and 90 relapsed MMs. (B) TRIP13 increases in sequential primary MM samples from 9 MM patients (36 samples). Red color for a gene indicates expression above the median and blue color indicates expression below the median. (C) Top 100 genes highly correlated with TRIP13 expression in newly diagnosed MM samples. The Heatmap shows 50-positive and 50-negative genes between TRIP13-high (n=88) and TRIP-13-low (n=88) MM samples.

FIGS. 37A-37G. PAA overcomes TRIP13-induced drug resistance in MM cells. (A) TRIP13-OE ARP1 cells are resistant to bortezomib. Cell viability showed that ARP1 MM cells with or without TRIP13-OE were treated with different doses of botezomib in ARP1-OE and the control cells ARP1-EV. (B) TRIP13-OE ARP1 cells are sensitive to pharmacological ascorbic acid (PAA). Cell viability showed ARP1-OE and ARP1-EV cells treated with different doses of PAA. (C) PAA selectively kills primary MM cells. Bar-view presents cell viability between CD138⁺ tumor cells and CD138⁻ non-tumor cells treated with either PAA (8, 20 mM) or PBS (control) from 9 MM patients (p<0.01). (D) PAA targets reactive oxidative species and labile iron pool: OCI-MY5 WT cells were incubated with or without catalase (100 U/mL), N-acetyl cysteine (NAC, 15 mM) or deferoxamine (DFO, 200 μM) for 3 h following treatment with PAA. PAA was washed away after 1 h treatment and cell viability was determined 24 h later. (E) PAA induces AIF1 cleavage: OCI-MY5 WT cells were incubated with or without PAA. After 1 h PAA was washed away and cells were incubated with melphalan (Mel, 0-80 μM) for 4 h. AIF1, β-actin and γ-H2AX levels were analyzed by western blots. (F) PAA acts synergistically with melphalan in vivo. Xenografted ARP1 MM cells injected in NOD.Cγ-Rag1 mice were treated with PAA and melphalan alone or in combination. Kaplan-Meier curves show that mouse survivals among these groups are significantly different (p<0.001) and that PAA, when combined with low dose of melphalan, extends MM mouse survival. (G) Electron microscopy shows AIF1 immunolabeling stain of OCI-MY5 WT cells treated without (up) or with (bottom) PAA (2 mM). N, M, C respectively represent nucleus, mitochondria and cytoplasm. Blue arrows indicate the nuclear membrane and red arrowheads indicate AIF1 gold beads in cytoplasm or mitochondria. Black arrowheads indicate AIF1 gold beads in nuclei.

FIGS. 38A-38D. TRIP13 regulates iron genes' expression and increases cellular iron. (A) Bar-views show the expression of TRIP13, Tfrc, and Fpn1 in pre-malignant B cells derived from Tg TRIP13/Eμ-Myc and Tg Eμ-Myc mice. (B) Dot-plots show the expression of TFRC and FPN1 between primary MM samples with low-TRIP13 expression (n=50) and High-TRIP13 expression (n=50). (C) Western blots show increased Ferritin in TRIP13-OE ARP1 MM cells. (D) Western blots show nuclear AIF1 expression with or without PAA or Bortezomib (Bor) treatment in ARP1 MM cell line.

Figure 39:
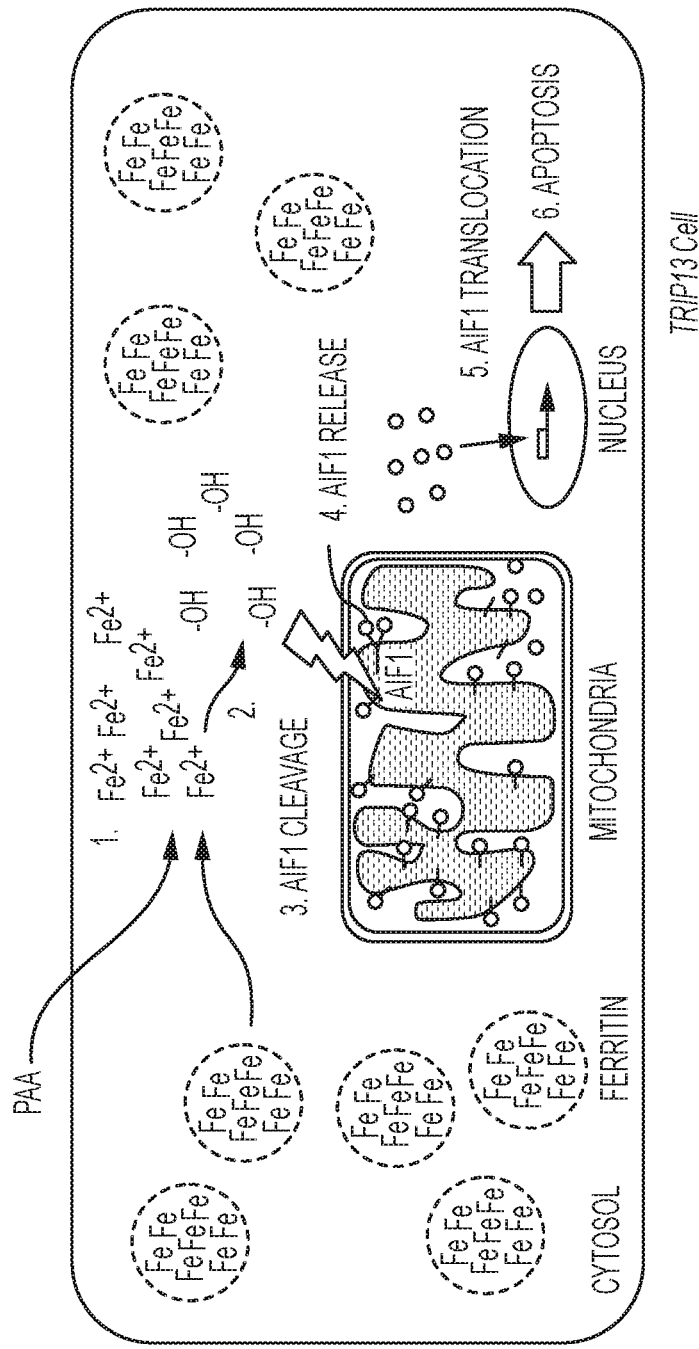

FIG. 39. Schematic representation of PAA action in TRIP13 cells. In brief, TRIP13 cells show increased levels of redox-active iron (1.) due to increased ferritin level. Once cells are treated with PAA, it reacts with $Fe^{2-}$ and by its oxidation will generated —OH (2.). PAA-mediated cellular oxidative damage leads to AIF1 cleavage (3.) from mitochondria. AIF1 cleavage form gets released in the cytoplasm (4.) and subsequently (5.) translocate to the nucleus inducing apoptosis (6.) and cell death.

DETAILED DESCRIPTION

The present invention provides in certain embodiments a therapeutic composition comprising a combination of (a) pharmacological ascorbic acid (PAA) or a pharmaceutically acceptable salt thereof; and (b) an alkylating agent.

In certain embodiments, the alkylating agent is melphalan or bendamustine.

In certain embodiments, the alkylating agent is melphalan.

The present invention provides in certain embodiments a method of treating a hyperproliferative disorder associated with high intracellular iron comprising administering pharmacological ascorbic acid (PAA) or a pharmaceutically acceptable salt thereof.

In certain embodiments, the PAA is administered at a dosage of about 15 g-100 g. In certain embodiments, the PAA is administered at a dosage of about 45 g-90 g. In certain embodiments, the PAA is administered at a dosage of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 grams.

In certain embodiments, the PAA is administered by infusion two times per week.

In certain embodiments, the method further comprises administering an alkylating agent.

In certain embodiments, the alkylating agent is melphalan or bendamustine.

In certain embodiments, the alkylating agent is melphalan.

In certain embodiments, the melphalan is administered at a dosage of about 2 mg/m² and 200 mg/m².

In certain embodiments, the melphalan is administered at a dosage of about 50 mg/m² and 100 mg/m².

In certain embodiments the melphalan is administered at a dosage of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/m².

In certain embodiments, the PAA and the alkylating agent are administered simultaneously.

In certain embodiments, the PAA and the alkylating agent are administered sequentially.

In certain embodiments, the administration of the PAA begins about 1 to about 10 days before administration of the alkylating agent.

In certain embodiments, the administration of the alkylating agent begins about 1 to about 10 days before administration of the PAA.

In certain embodiments, the administration of the PAA and alkylating agent begin on the same day.

In certain embodiments, the PAA is administered about less than four hours prior to the administration of the alkylating agent.

The present invention provides in certain embodiments a method of treating a hyperproliferative disorder associated with high intracellular iron comprising administering pharmacological ascorbic acid (PAA) or a pharmaceutically acceptable salt thereof and a proteasome inhibitor.

In certain embodiments, the proteasome inhibitor is carfizomib.

In certain embodiments, the carfizomib is administered at a dosage of about 2 mg/m$^2$ to 200 mg/m$^2$.

In certain embodiments, the carfizomib is administered at a dosage of about 50 mg/m$^2$ to 100 mg/m$^2$.

In certain embodiments, the proteasome inhibitor (e.g., carfizomib) is administered at a dose of 56 mg/m$^2$ on days 1, 8, 15 and 22 of each 4-week cycle.

In certain embodiments, the PAA and the proteasome inhibitor are administered simultaneously.

In certain embodiments, the PAA and the proteasome inhibitor are administered sequentially.

In certain embodiments, the administration of the PAA begins about 1 to about 10 days before administration of the proteasome inhibitor.

In certain embodiments, the administration of the proteasome inhibitor begins about 1 to about 10 days before administration of the PAA.

In certain embodiments, the administration of the PAA and proteasome inhibitor begin on the same day.

In certain embodiments, the PAA is administered about less than four hours prior to the administration of the proteasome inhibitor.

In certain embodiments, the method further comprises administering an anti-cancer therapy.

In certain embodiments, the anti-cancer therapy is immunotherapy or biologic therapy.

In certain embodiments, the hyperproliferative disorder associated with high iron is multiple myeloma, smoldering multiple myeloma, ovarian cancer, pancreatic cancer, neuroblastoma, rhabdomyosarcoma, or breast cancer.

In certain embodiments, the hyperproliferative disorder associated with high iron is multiple myeloma, including smoldering multiple myeloma.

The present invention provides in certain embodiments a method of reducing toxic effects of melphalan in a patient in need thereof comprising administering pharmacological ascorbic acid (PAA) or a pharmaceutically acceptable salt thereof.

The present invention provides in certain embodiments a method of treating multiple myeloma, including smoldering multiple myeloma, comprising administering pharmacological ascorbic acid (PAA) or a pharmaceutically acceptable salt thereof.

In certain embodiments, the PAA is administered at a dosage of about 15-100 g.

In certain embodiments, the PAA is administered at a dosage of about 45 g-90 g infusion.

In certain embodiment's, the PAA is administered by infusion two times per week.

The present invention provides in certain embodiments a use of the combination of pharmacological ascorbic acid (PAA) or a pharmaceutically acceptable salt thereof and melphalan in the preparation of a medicament for the treatment of a hyperproliferative disorder in a mammal.

In certain embodiments, the present invention provides the use of the combination of pharmacological ascorbic acid (PAA) or a pharmaceutically acceptable salt thereof and carfizomib in the preparation of a medicament for the treatment of a hyperproliferative disorder in a mammal.

The present invention provides in certain embodiments a kit comprising pharmacological ascorbic acid (PAA) or a pharmaceutically acceptable salt thereof and melphalan, a container, and a package insert or label indicating the administration of the PAA and with melphalan for treating a hyperproliferative disorder.

In certain embodiments, the present invention provides a kit comprising pharmacological ascorbic acid (PAA) or a pharmaceutically acceptable salt thereof and carfizomib, a container, and a package insert or label indicating the administration of the PAA and with carfizomib for treating a hyperproliferative disorder.

The present invention provides in certain embodiments a product comprising pharmacological ascorbic acid (PAA) and melphalan as a combined preparation for separate, simultaneous or sequential use in the treatment of a hyperproliferative disorder.

In certain embodiments, the PAA is administered for more than a month. In certain embodiments, the PAA is administered for more than a year.

In certain embodiments, the PAA is administered at a dosage of at least 75 g/day and the alkylating agent is administered at a dosage of at least 35 mg/day.

In certain embodiments, the PAA is administered intravenously.

In certain embodiments, the PAA is administered at a dosage of at least 50 g/infusion.

The present invention provides in certain embodiments a therapeutic composition comprising a combination of (a) pharmacological ascorbic acid (PAA) or a pharmaceutically acceptable salt thereof; and (b) an alkylating agent.

In certain embodiments, the alkylating agent is melphalan or bendamustine.

In certain embodiments, the alkylating agent is melphalan.

The present invention provides in certain embodiments a therapeutic composition comprising a combination of (a) pharmacological ascorbic acid (PAA) or a pharmaceutically acceptable salt thereof; and (b) a proteasome inhibitor.

In certain embodiments, the proteasome inhibitor is carfizomib.

The present invention provides in certain embodiments, a method of administering to a mammalian cell having down-regulated expression of Ferroportin 1 (Fpn1) as compared with its normal counterpart cell an expression-modulating agent, comprising contacting the mammalian cell with pharmacological ascorbic acid (PAA) or a pharmaceutically acceptable salt thereof.

The present invention provides in certain embodiments, a method of administering to a mammalian cell having upregulated expression of enhancer of zeste 2 (EZH2) as compared with its normal counterpart cell an expression-modulating agent, comprising contacting the mammalian cell with an inhibitor of EZH2.

In certain embodiments, the inhibitor of EZH2 is DZNep or GSK343.

In certain embodiments, the method further comprises contacting the mammalian cell pharmacological ascorbic acid (PAA) or a pharmaceutically acceptable salt thereof.

The present invention provides in certain embodiments, a method of administering to a mammalian cell having upregulated expression of Thyroid Hormone Receptor Interactor Protein 13 (TRIP13) as compared with its normal counterpart cell an expression-modulating agent, comprising contacting the mammalian cell with pharmacological ascorbic acid (PAA) or a pharmaceutically acceptable salt thereof and/or with an inhibitor of TRIP13.

Pharmaceutical Ascorbic Acid (PAA)

Vitamin C is a highly effective and non-toxic anti-oxidant that can be used to protect the body against oxidative stress including free radicals. As used herein, a reference to ascorbic acid includes the anionic component, ascorbate whether as an acid or one of the pharmaceutically acceptable salts thereof, such as sodium ascorbate and calcium ascorbate, all of which are included in a reference to CGMP "ascorbic acid" or "ascorbate."

Injectable pharmacological ascorbic acid (PAA), or vitamin C, has recently re-emerged as a promising anti-cancer therapy. Studies in a variety of cancer cell types, both in cell culture and animal models, have demonstrated selective (relative to normal cells) cancer cell killing as well as selective sensitization of cancer cells to standard of care therapies when combined with injectable pharmacological ascorbate. PAA's selective toxicity to cancer cells appears to be dependent upon the presence of redox active metal ions (such as iron), which are capable of receiving and donating electrons during the oxidation of ascorbate to form hydrogen peroxide.

Patients with a variety of cancer types are currently receiving intravenous pharmacological ascorbate in combination with standard cancer therapies in clinical trials to determine pharmacological ascorbate's clinical safety and efficacy. Pharmacological ascorbate has recently been shown in tissue culture models and animal modes to increase the sensitivity of tumor cells to chemotherapy and radiation therapy. In addition, phase I clinical trials assessing the tolerability of pharmacological ascorbate in a variety of cancer types have been well tolerated.

Pharmacological doses of ascorbate (resulting in plasma concentrations ≥10 mM) can be achieved by intravenous (IV) administration and have been shown to be safe and well tolerated in both animals and humans. (Welsh et al., Pharmacological ascorbate with gemcitabine for the control of metastatic and node-positive pancreatic cancer (PACMAN): results from a phase I clinical trial. Cancer Chemother Pharmacol. 2013 March; 71(3):765-775; Ma et al., High-Dose Parenteral Ascorbate Enhanced Chemosensitivity of Ovarian Cancer and Reduced Toxicity of Chemotherapy. Sci Transl Med. 2014 Feb. 5; 6(222):222ra18-222ra18). Recent in vitro experiments demonstrate that pharmacological ascorbate is selectively toxic to cancer cells, whereas normal cells are unaffected (preliminary results). (Du et al., Mechanisms of ascorbate-induced cytotoxicity in pancreatic cancer Clin Cancer Res. 2010 Jan. 15; 16(2):509-20 PMID: 20068072). High ascorbate concentrations in cancer cells appear to selectively induce the formation of $H_2O_2$ via the catalytic oxidation of ascorbate in the presence of redox active metals such as iron (Fe). (Chen et al., Pharmacologic ascorbic acid concentrations selectively kill cancer cells: action as a pro-drug to deliver hydrogen peroxide to tissues. Proc Natl Acad Sci USA. 2005 Sep. 20; 1 02(38):13604-13609.) Because cancer cells are believed to have higher concentrations of labile redox active metal ions due to increased steady-state levels of superoxide, pharmacological ascorbate will selectively increase $H_2O_2$ in lung cancer cells, relative to normal lung cells, thereby increasing the sensitivity of NSCLC to chemo-radiation therapy by increasing oxidative stress (preliminary results).

The method of the present invention comprises the treatment of cancer by administering sufficient amounts of ascorbic acid to raise the concentration of ascorbic acid in the patient's plasma above a level that is cytotoxic to the cancer tumor cells. In certain embodiments, ascorbate is administered so as to reach a blood level of at least about 20 mM. Doses of 75 g/infusion or greater are typically able to achieve this concentration.

Inhibitors of EZH2

In certain embodiments, the inhibitor of EZH2 is DZNep or GSK343.

Inhibitors of TRIP13

In certain embodiments, the inhibitor of TRIP13 is P5091.

Anti-Cancer Therapy

As used herein, the term "anti-cancer therapy" includes therapeutic agents that kill cancer cells; slow tumor growth and cancer cell proliferation; and ameliorate or prevent one or more of the symptoms of cancer. For example, the term "anti-cancer therapy" includes an anti-cancer therapy that enhances DNA damage in cancer cells. In certain embodiments, the anti-cancer therapy is standard immunotherapy or biologic therapy.

Alkylating Agents. Alkylating agents are a class of chemotherapy drugs that bind to DNA and prevent proper DNA replication. They have chemical groups that can form permanent covalent bonds with nucleophilic substances in the DNA. In certain embodiments, the alkylating agent is melphalan or bendamustine.

Additive Agents

In certain embodiments, the combination further comprises an inhibition agent that inhibits glucose and/or hydroperoxide metabolism. In certain embodiments, the inhibition agent is Buthionine sulfoximine, Auranofin, 2-deoxyglucose, other inhibitors of glutathione and/or thioredoxin metabolism, inhibitors of catalase, sulfasalazine, other inhibitors of cysteine transport, inhibitors of glucose transport, diets that limit glucose and other simple sugars such as ketogenic diets.

Hyperproliferative Diseases

In certain embodiments of the methods described above, the cancer is breast cancer, prostate cancer, lung cancer, pancreas cancer, head and neck cancer, ovarian cancer, brain cancer, colon cancer, hepatic cancer, skin cancer, leukemia, melanoma, endometrial cancer, neuroendocrine tumors, carcinoids, neuroblastoma, glioma, tumors arising from the neural crest, lymphoma, myeloma, or other malignancies characterized by aberrant mitochondrial hydroperoxide metabolism. In certain embodiments, the cancer is the above cancers that are not curable or not responsive to other therapies. In certain embodiments, the cancer is multiple myeloma, smoldering multiple myeloma, ovarian cancer, pancreatic cancer, neuroblastoma, rhabdomyosarcoma, or breast cancer.

Compositions and Methods of Administration

The method of the present invention comprises the treatment of cancer by administering sufficient amounts of ascorbic acid to raise the concentration of ascorbic acid in the patient's plasma above a level that is cytotoxic to the cancer tumor cells, in combination with an alkylating agent (such as melphalan), and optionally with an additional anti-cancer therapy.

The present invention provides a method for increasing the anticancer effects of an alkylating agent (such as melphalan), optionally in conjunction with conventional cancer therapy (i.e., radio- and/or chemo-therapy) on cancerous cells in a mammal. In certain embodiments, the method comprises contacting the cancerous cell with an effective amount of pharmaceutical ascorbic acid (PAA) or a pharmaceutically acceptable salt thereof and an alkylating agent (such as melphalan), and optionally administering an additional conventional cancer therapy modality. In certain embodiments, the additional cancer therapy is chemotherapy. In certain embodiments, the PAA and alkylating agent are administered sequentially to a mammal rather than in a single composition. In certain embodiments, the mammal is a human.

In certain embodiments of the methods described above, the composition does not significantly inhibit viability of comparable non-cancerous cells.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Ascorbate, alkylating agents and anti-cancer agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., intravenously, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. The amount of active compound in such therapeutically useful compositions is such that an effective dosage level will be obtained.

Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The dosage of the ascorbate, alkylating agent(s) and the anti-cancer agent will vary depending on age, weight, and condition of the subject. Treatment may be initiated with small dosages containing less than optimal doses, and increased until a desired, or even an optimal effect under the circumstances, is reached. In general, the dosage is about 75-100 g per infusion Higher or lower doses, however, are also contemplated and are, therefore, within the confines of this invention. A medical practitioner may prescribe a small dose and observe the effect on the subject's symptoms. Thereafter, he/she may increase the dose if suitable. In general, the ascorbate, alkylating agent(s) and the anti-cancer agent are administered at a concentration that will afford effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include parenteral, e.g., intravenous, slow infusion, intradermal, subcutaneous, oral (e.g., ingestion or inhalation), transdermal (topical), transmucosal, and rectal administration depending on the location of the tumor. Such compositions typically comprise the PBA or pharmaceutically acceptable salt thereof and the anti-cancer agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; alkylating agents such as melphalan; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Examples.

EXAMPLE 1

Efficacy of Lower-Dose of Melphalan Plus Pharmacological Ascorbic Acid as New Therapy for Multiple Myeloma High-dose chemotherapies to treat multiple myeloma (MM) can be life-threatening due to toxicities to normal cells and there is a need to target only tumor cells and/or lower standard drug dosage without losing efficacy. We show that pharmacologically-dosed ascorbic acid (PAA) in the presence of iron leads to the formation of highly reactive oxygen species (ROS) resulting in cell death. PAA selectively killed $CD138^+$ MM tumor cells derived from MM and smoldering MM (SMM) but not from undetermined significane (MGUS) MGUS patients. PAA alone or combination with carfizomib or melphalan inhibits tumor formation in MM xenograft mice. This is first report on PAA efficacy on primary cancer cells in vitro and in vivo.

Multiple myeloma (MM) is a plasma cell neoplasm. Four active classes of drugs including glucocorticoids, DNA alkylators (melphalan), proteasome inhibitors (bortezomib and carfizomib) and immunomodulatory agents (thalidomide, lenalidomide, and pomalidomide), combined with or without Autologous Stem Cell Transplantation (ASCT) have led to complete remissions (CRs) in the large majority of newly diagnosed patients with MM (Alexanian, R., et al. Value of novel agents and intensive therapy for patients with multiple myeloma. Bone marrow transplantation 49, 422-425 (2014); Fu, C., et al. Therapeutic effects of autologous hematopoietic stem cell transplantation in multiple myeloma patients. Exp Ther Med 6, 977-982 (2013); Terpos, E., et al. VTD consolidation, without bisphosphonates, reduces bone resorption and is associated with a very low incidence of skeletal-related events in myeloma patients post ASCT. Leukemia 28, 928-934 (2014); Wang, L., Xu, Y. L. & Zhang, X. Q. Bortezomib in combination with thalidomide or lenalidomide or doxorubicin regimens for the treatment of multiple myeloma: a metaanalysis of 14 randomized controlled trials. Leukemia & lymphoma 55, 1479-1488 (2014); Sonneveld, P., et al. Bortezomib-based versus nonbortezomib-based induction treatment before autologous stem-cell transplantation in patients with previously untreated multiple myeloma: a meta-analysis of phase III randomized, controlled trials. Journal of clinical oncology: official journal of the American Society of Clinical Oncology 31, 3279-3287 (2013); Gay, F., et al. Bortezomib induction, reduced-intensity transplantation, and lenalidomide consolidation-maintenance for myeloma: updated results. Blood 122, 1376-1383 (2013); Liu, J., et al. Determining the optimal time for bortezomib-based induction chemotherapy followed by autologous hematopoietic stem cell transplant in the treatment of multiple myeloma. Chin J Cancer Res 25, 166-174 (2013); Bergsagel, P. L. Where we were, where we are, where we are going: progress in multiple myeloma. American Society of Clinical Oncology educational book/ASCO. American Society of Clinical Oncology. Meeting, 199-203 (2014)). These treatments have greatly improved patient progression-free and overall survival. However, there are at least three major problems limiting the administration of these agents: 1. All these drugs target both tumor and non-tumor cells; 2. Increased hematologic toxicity has been identified by combining alkylators with either IMIDs; and 3. High doses of the DNA alkalating agent, such as melphalan, have strong cytotoxicity on gut epithelial cells and hematopoietic stem cells. One way to deal with non-selective toxicity of high dose melphalan is to combine it with another agent which very specifically targets tumor cells and therefore allows a decrease in melphalan dose without loss of efficacy.

In the 1970s, Cameron and Pauling reported that high doses of vitamin C increased survival of patients with cancer (Cameron, E. & Pauling, L. Supplemental ascorbate in the supportive treatment of cancer: Prolongation of survival times in terminal human cancer. Proceedings of the National Academy of Sciences of the United States of America 73, 3685-3689 (1976); Cameron, E. & Pauling, L. Supplemental ascorbate in the supportive treatment of cancer: reevaluation of prolongation of survival times in terminal human cancer. Proceedings of the National Academy of Sciences of the United States of America 75, 4538-4542 (1978)). Recently, reports have shown that pharmacologically dosed ascorbic acid (PAA) 20~80 folds higher than physiologically dosed ascorbate, administered intravenously, has potent anti-cancer activity and its role as a novel anti-cancer therapy is being studied at the University of Iowa and in other centers. In the presence of catalytic metal ions like iron, PAA administered intravenously exerts pro-oxidant effects leading to the formation of highly reactive oxygen species (ROS), resulting in cell death (Du, J., Cullen, J. J. & Buettner, G. R. Ascorbic acid: chemistry, biology and the treatment of cancer. Biochimica et biophysica acta 1826, 443-457 (2012); Ma, Y., et al. High-dose parenteral ascorbate enhanced chemosensitivity of ovarian cancer and reduced toxicity of chemotherapy. Science translational medicine 6, 222ra218 (2014); Yun, J., et al. Vitamin C selectively kills KRAS and BRAF mutant colorectal cancer cells by targeting GAPDH. Science 350, 1391-1396 (2015); Chen, Q., et al. Ascorbate in pharmacologic concentrations selectively generates ascorbate radical and hydrogen peroxide in extracellular fluid in vivo. Proceedings of the National Academy of Sciences of the United States of America 104, 8749-8754 (2007); Chen, Q., et al. Pharmacologic ascorbic acid concentrations selectively kill cancer cells: action as a pro-drug to deliver hydrogen peroxide to tissues. Proceedings of the National Academy of Sciences of the United States of America 102, 13604-13609 (2005)). In a previous study, it was reported that the labile iron pool (LIP) is significantly elevated in MM cells, suggesting that PAA treatment should target MM cells quite selectively (Gu, Z., et al. Decreased ferroportin promotes myeloma cell growth and osteoclast differentiation. Cancer research 75, 2211-2221 (2015)). The higher LIP is the direct result of the low expression of the only known mammalian cellular iron exporter, Ferroportin 1 (Fpn1), in MM as demonstrated. These findings led to the current hypothesis that PAA might specifically target MM cells with high iron content and may also act synergistically in combination with commonly used MM therapies.

Methods

Patients and Mice

Peripheral-blood samples or bone marrow aspirates were obtained from patients with monoclonal gammopathy of undetermined significance (MGUS), smoldering multiple myeloma (SMM), and multiple myeloma (MM). Written informed consent was obtained from all the participants. The study was approved by the institutional review board at the University of Iowa. NOD.Cγ-Rag1 mice (Jackson laboratory, Bar Harbor, Me.) were bred and maintained in compliance with the guidelines of the institutional animal care at the University of Iowa.

Gene Expression

Gene expression profiling (GEF) has been described previously (Zhan et al., The molecular classification of multiple myeloma. Blood 108, 2020 (Sep. 15, 2006); Shaughnessy, Jr. et al., A validated gene expression model of high-risk multiple myeloma is defined by deregulated expression of genes mapping to chromosome 1. Blood 109, 2276 (Mar. 15, 2007)). GEP access number of normal plasma cell (NPC), MGUS, and primary myeloma samples is GSE2658.

Pharmacological Ascorbic Acid Viability Assay

Pharmacological Ascorbic Acid (PAA) was kindly provided by Dr. Garry R. Buettner (University of Iowa). CD138$^+$ MM cells and CD138$^-$ non-MM cells were isolated from MGUS, SMM, and MM patient samples using anti-CD138 immunomagnetic beads (Miltenyl Biotec, Auburn, Calif.). Cells were cultured with or without PAA at the described concentration for 1 hr. After incubation, the cells were washed and cultured up to 24 h. Cell counts and viable cell number were determined using Trypan Blue staining.

Human Myeloma Xenografts Mice

NOD.Cγ-Rag1 mice 6-8 weeks old (Jackson laboratory, Bar Harbor, Me.) were injected intravenously with ARP1 MM cells ($1\times10^6$) expressing luciferase. After one-week injection of ARP1 cells, mice were treated with either PAA (4 mg/kg) injected intraperitoneal once a day, 5 days every week for 3 weeks. Melphalan (3 mg/kg) was injected intraperitoneal once a day, 2 days a week for 3 weeks (Sanchez, E., et al. Serum B-cell maturation antigen is elevated in multiple myeloma and correlates with disease status and survival. British journal of haematology 158, 727-738 (2012).) Carfizomin (3 mg/kg) was injected by in vein once a day, 2 days every week for 3 weeks (Eda, H., et al. A novel Bruton's tyrosine kinase inhibitor CC-292 in combination with the proteasome inhibitor carfilzomib impacts the bone microenvironment in a multiple myeloma model with resultant antimyeloma activity. Leukemia 28, 1892-1901 (2014)). Bortezomib (3 mg/kg) was injected intraperitoneal once a day, 2 days a week for 3 weeks. The mice were euthanized when humane endpoint was reached.

In Vivo Imaging System (IVIS)

Xenogen IVIS-200 an in vivo imaging system (IVIS) was used to analyze tumor burden and was indicated by quantification of luciferase intensity of mice pre- and post-treatments.

Cell Culture

Human myeloma cell lines (ARP1, OCI-MY5 and their derivative cell lines) were cultured in RPMI 1640 (Invitrogen, Carlsbad, Calif.), supplemented with 10% heat-inactivated FBS (Invitrogen), penicillin (100 IU/mL), and streptomycin (100 µg/mL) in a humidified incubator at 37° C. and 5% $CO_2$/95% air. To increase cellular iron concentration, ferric nitrilotriacatate (Fe-NTA) was used.

Western Blotting

Cells were harvested and lysed with lysis buffer: 150 mM NaCl, 10 mM EDTA, 10 mM Tris, pH 7.4, 1% X-100 Triton. Cell lysates were subjected to SDS-PAGE, transferred onto a pure nitrocellulose membrane (BioRad), and blocked with 5% fat-free milk. Primary antibodies for immunoblotting included: anti-AIF1 (1:1000, Cell Signaling), anti-RIP (1:1000, Santa Cruz Biotechnology), anti-RIP3 (1:1000, Cell Signaling), anti-Caspase3 (1:1000, Cell Signaling), anti-Caspase 8 (1:1000, Cell Signaling), anti-Caspase 9 (1:1000, Cell Signaling) Phosphorylated γH2AX (1:1000, Enzo Life Sciences), and β-actin (1:1000, Cell Signaling) as loading control. Membranes were incubated with horseradish peroxidase (HRP)-conjugated anti-mouse secondary antibody (1:10,000, Santa Cruz Biotechnology, cat #: sc-2005) or anti-rabbit secondary antibody (1:10,000, AnaSpec Inc., cat #: AS-28177) for 1 h and chemi-luminescence signals were detected by HRP substrate (EMD Millipore).

Statistical Analyses

GEP data were analyzed by One-Way Anova test using log 2 transformed Affymetrix Signals and presented by boxplot. The comparisons of tumor burden were analyzed either by student t-test (2 groups) or by One-Way Anova test (>2 groups). Kaplan-Meier method was performed for survival with the use of SPSS 16.0 software (SPSS, Chicago, Ill.). Two-tailed p value at an alpha level of 0.05 was considered to indicate statistical significance. Graphs were generated using Prism 6 software.

Electron Microscopy

Electron microscopy was performed by the Central Microscopy Research Facility personnel at the University of Iowa. Images were captured on JEOL JEM 1230.

Results

Pharmacological Ascorbic Acid (PAA) Selectively Kills Myeloma Tumor Cells

Figure 5:
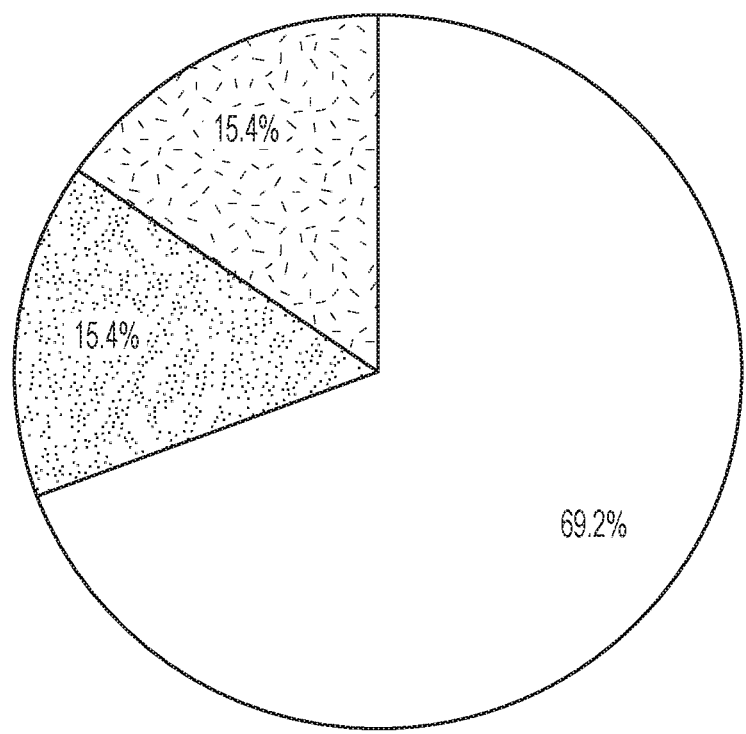
FIG. 5. Pie chart of patients' diagnosis.

The response to PAA of both $CD138^+$ primary MM cells (high cytosolic iron) and $CD138^-$ non-myeloma bone marrow (BM) cells obtained from 13 patients was analyzed. The 13 patients included 2 monoclonal gammopathy of undetermined significance (MGUS), 2 smoldering MM (SMM) and 9 MM patients. Patient demographic, disease characteristics and therapy are listed in Table 1 and FIG. 5.

TABLE 1

| Subject | Disease | Age | Sex | M-component type | Stage (ISS) | Plasma Cells (%) | Cytogenetics | Last treatment |
|---|---|---|---|---|---|---|---|---|
| 1 | MGUS | 58 | F | IgA Kappa | nd | 5.0 | Hyperdiploid karyotype p53 amplification | NT |
| 3 | MM | 65 | M | IgG Kappa | I | 20 | Hyperdiploid karyotype | D-PACE |
| 4 | MM | 38 | M | IgG Kappa | II | 2.0 | Hyperdiploid karyotype | Carfilzomib Dexamethasone Lenalidomide |
| 5 | MM | 62 | F | IgG Lambda | I | 4.0 | 1q amplification t (14;16)(q32;q23) | Melphalan VTD |
| 6 | MM | 62 | M | IgG Lambda | III | 80 | Hypodiploid karyotype 1q amplification | VDT |
| 7 | MM | 79 | F | IgG Kappa | III | 10 | 1q amplification p53 amplification t (4;14) (p16;q32) | Dexamethasone Lenalidomide |
| 8 | MM | 59 | M | IgG Lambda | II | 5.0 | 1q amplification t (4;14) (p16;q32) | Bortezomib Lenalidomide |
| 9 | MM | 56 | F | Lambda Light Chain ONLY | II | <1 | Hypodiploid karyotype | RVD |
| 11 | SMM | 48 | M | IgA Kappa | nd | 6.0 | Hypodiploid karyotype 1q amplification t (4;14) (p16;q32) | NT |
| 12 | SMM | 60 | M | IgG Lambda | nd | 15 | Hypodiploid karyotype 1q amplification | NT |

TABLE 1-continued

| Subject | Disease | Age | Sex | M-component type | Stage (ISS) | Plasma Cells (%) | Cytogenetics | Last treatment |
| --- | --- | --- | --- | --- | --- | --- | --- | --- |
| 13 | MM | 49 | F | IgA Lambda | II | 60 | Hyperdiploid karyotype | Bortezomib Dexamethasone |
| 14 | MGUS | 65 | F | IgG Lambda | nd | 5 | Normal FISH | NT |
| 15 | MM | 61 | F | IgG Kappa | I | 17 | 13q deletion 1q amplification t (11;14)(q13;q32) | Bortezomib Dexamethasone |

Figures 1A, 1B, 1C, 1D:
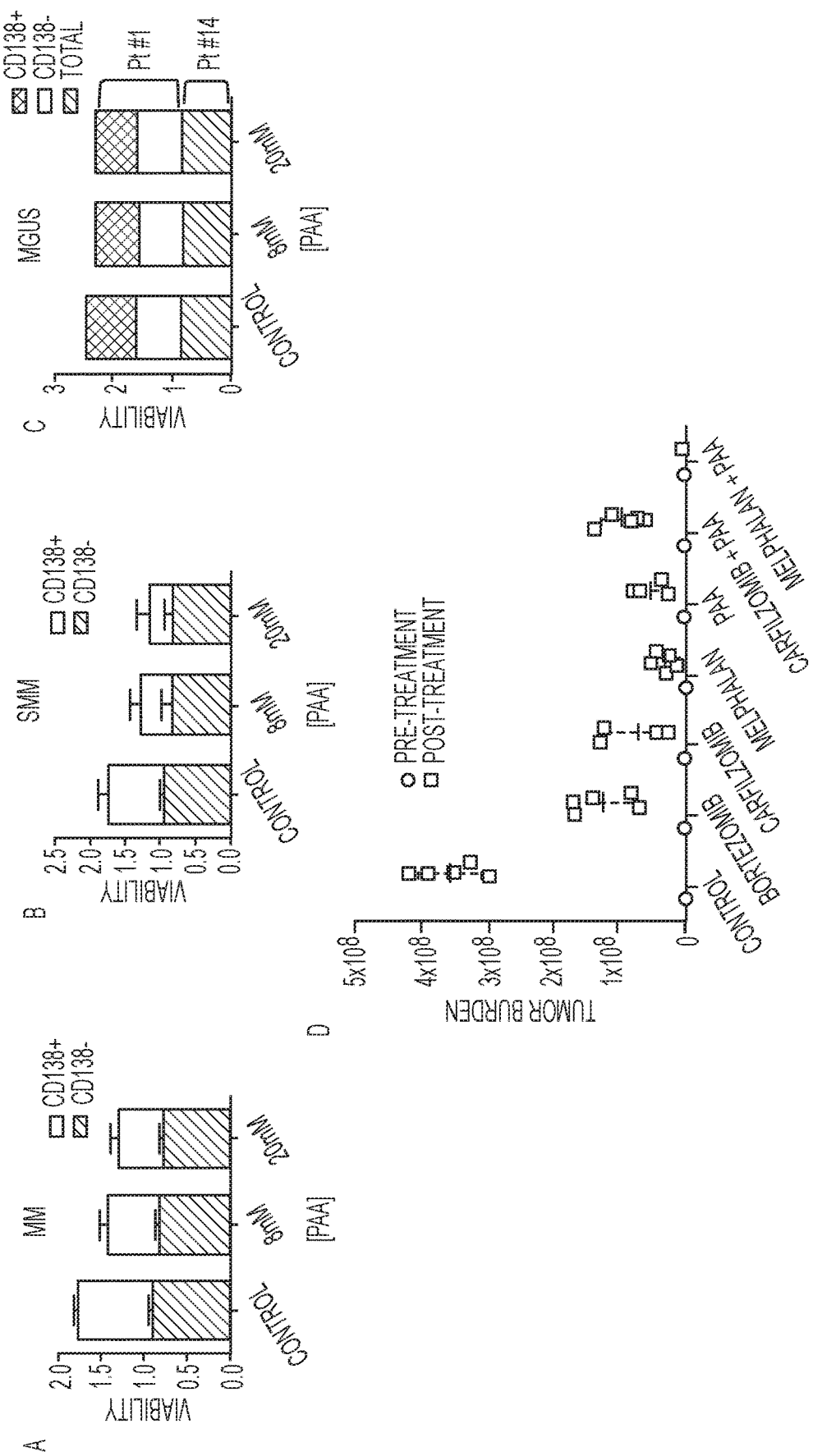
FIGS. 1A-1G. Pharmacologic ascorbic acid selectively kills tumor cells in MM and synergistically acts with melphalan in vivo.
Figures 2A, 2B, 2C, 2D:
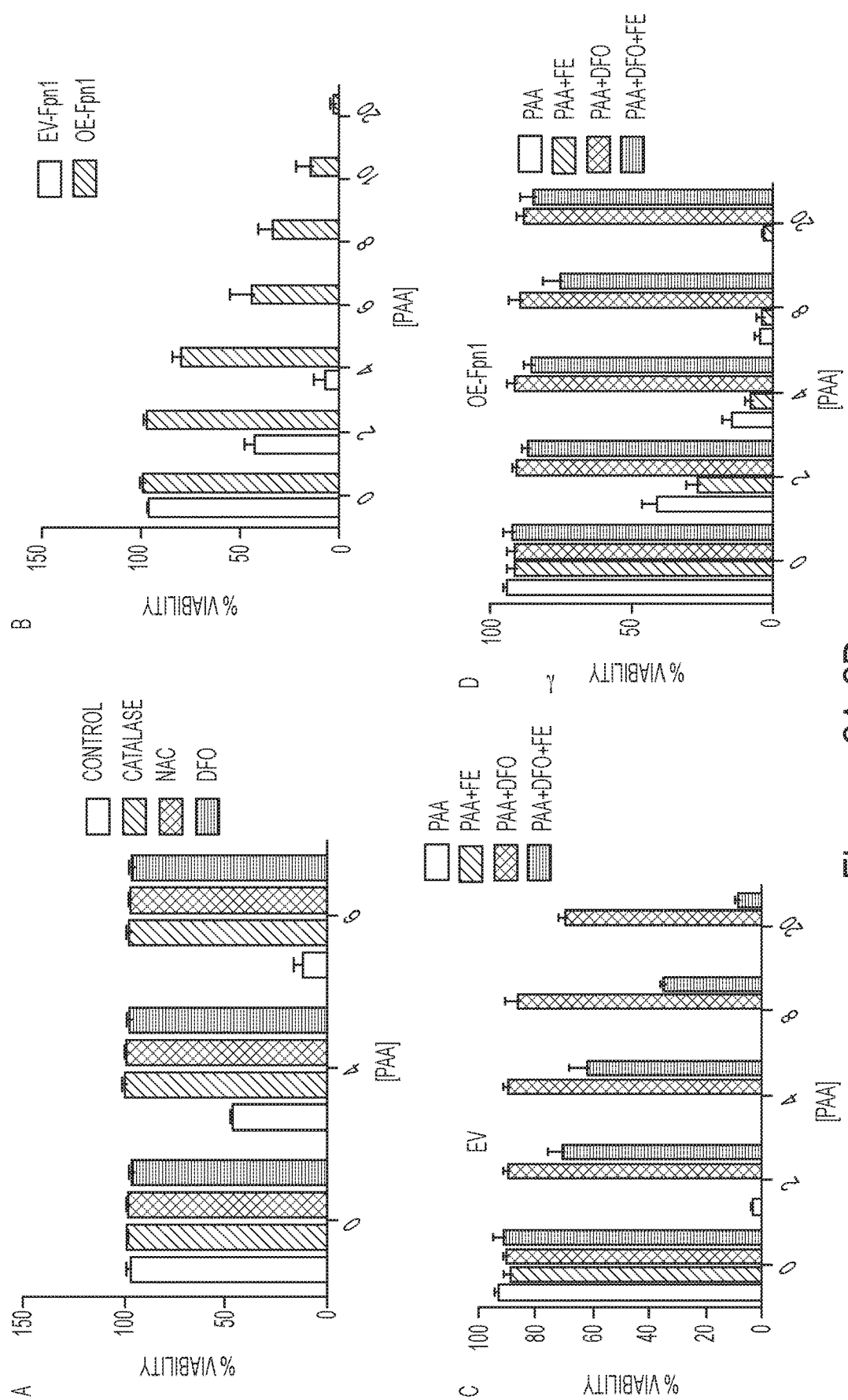
FIGS. 2A-2D. Pharmacologic ascorbic acid targets reactive oxidative species and labile iron pool.
Figures 6A, 6B:
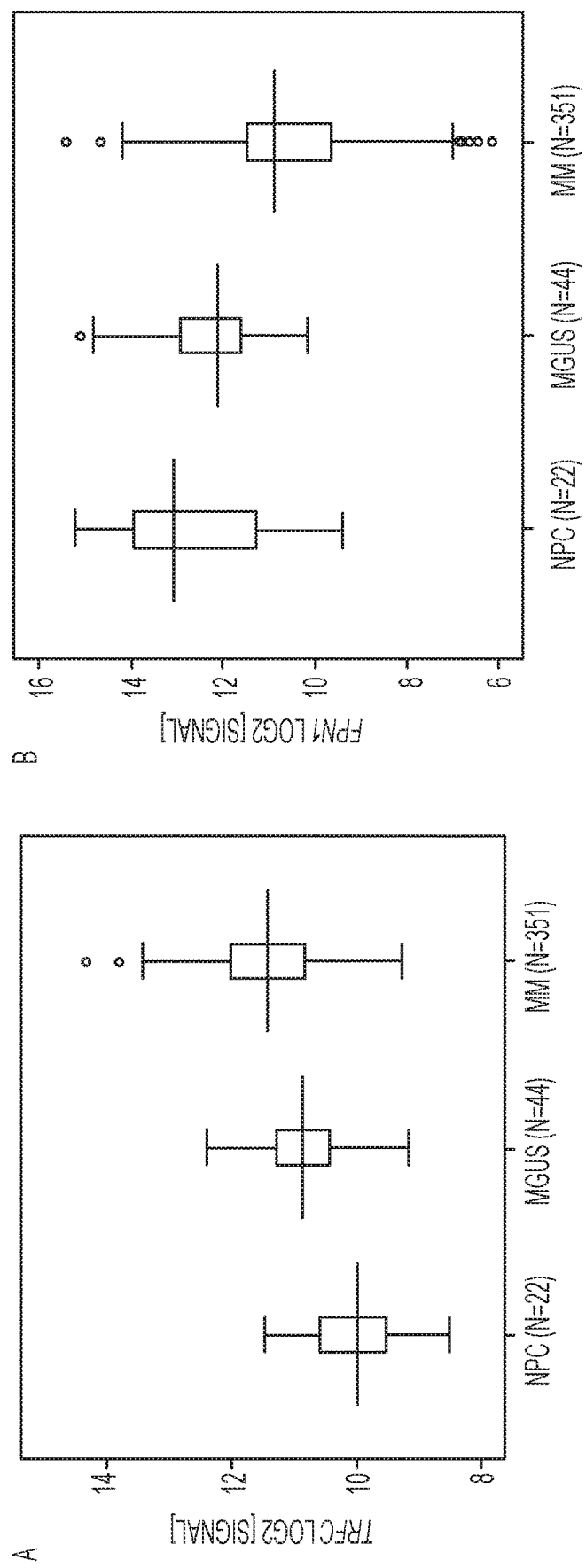
FIGS. 6A-6B. Box charts of iron transporter expression profiles show dysregulation between normal plasma cells and MM cells. The 22 normal plasma cell (NPC), 44 MGUS, and 351 newly diagnosed MM samples are distributed along the x-axis and the log 2-transformed Affymetrix Signal is plotted on the y-axis. The top, bottom, and middle lines of each box correspond to the 75th percentile (top quartile), 25th percentile (bottom quartile), and 50th percentile (median) of the log 2-transformed Affymetrix Signal for each gene, respectively. The whiskers extend from the 10th percentile (bottom decile) and top 90th percentile (top decile). The One-Way ANOVA tests for differences in expression of each gene across the groups are: TfR1, $p<0.001$; FPN1, $p<0.001$.

The survival of CD138$^+$ cells in vitro was significantly decreased following PAA treatment in all 9 MM (FIG. 1A, grey bars). In contrast, no significant change of cell viability was observed in CD138$^-$ BM cells from the same patients (FIG. 1A, black bars). The same effect of PAA was also observed in the SMM patients (FIG. 1B). However, almost no response to PAA was detected in CD138$^+$ cells from the 2 MGUS patients (FIG. 1C). It was predicted that this would be the case because MGUS patients have much lower cytosolic iron compared to MM patients (FIGS. 2A-2B) as the consequence of lower expression of transferrin receptor 1, the cellular iron receptor-mediated importer (FIG. 6A), and higher expression of Ferroportin 1 (Fpn1), the iron exporter (FIG. 2B).

Pharmacological Ascorbic Acid Decreases Melphalan Doses in Myeloma Treatment

To confirm the capacity of PAA to induce MM cell death in vivo, ARP1 MM cells expressing luciferase were injected intravenously into NOD.Cγ-Rag1 (n=6) mice. Three days later, half of the injected mice were treated for 15 days with PAA (4 mg/kg, once per day, IP) and the other half with saline as controls. An in vivo imaging system (IVIS) showed that tumor progression was significantly delayed in mice treated with PAA (data not shown). These data support the concept that PAA also targets MM cells effectively in vivo. To investigate whether PAA may be effective in killing MM cells when combined with currently used MM therapies, we treated mice with melphalan or carfilzomib or bortezomib. Seven combinations (control, PAA, melphalan, carfilzomib, melphalan+PAA, carfilzomib+PAA and bortezomib) were tested in vivo (Sanchez, E., et al. Serum B-cell maturation antigen is elevated in multiple myeloma and correlates with disease status and survival. British journal of haematology 158, 727-738 (2012); Eda, H., et al. A novel Bruton's tyrosine kinase inhibitor CC-292 in combination with the proteasome inhibitor carfilzomib impacts the bone microenvironment in a multiple myeloma model with resultant antimyeloma activity. Leukemia 28, 1892-1901 (2014)). Compared to the control group, all treatments inhibited MM cell growth significantly (p<0.05) (FIG. 1D). Within the single agent treatments, melphalan only showed a higher decrease in tumor burden when compared to PAA treatment and other single agents tested. However, the combination of melphalan plus PAA showed greater tumor burden reduction than either drug alone, suggesting a synergistic activity between the two drugs. Bortezomib was not given in combination with PAA because ascorbic acid directly inactivates bortezomib by forming a tight and reversible complex through its vicinal diol group (Perrone, G., et al. Ascorbic acid inhibits antitumor activity of bortezomib in vivo. Leukemia 23, 1679-1686 (2009); Harvey, R. D., Nettles, J., Wang, B., Sun, S. Y. & Lonial, S. Commentary on Perrone et al.: "Vitamin C: not for breakfast anymore . . . if you have myeloma". Leukemia 23, 1939-1940 (2009)).

Figures 1E, 1F, 1G:
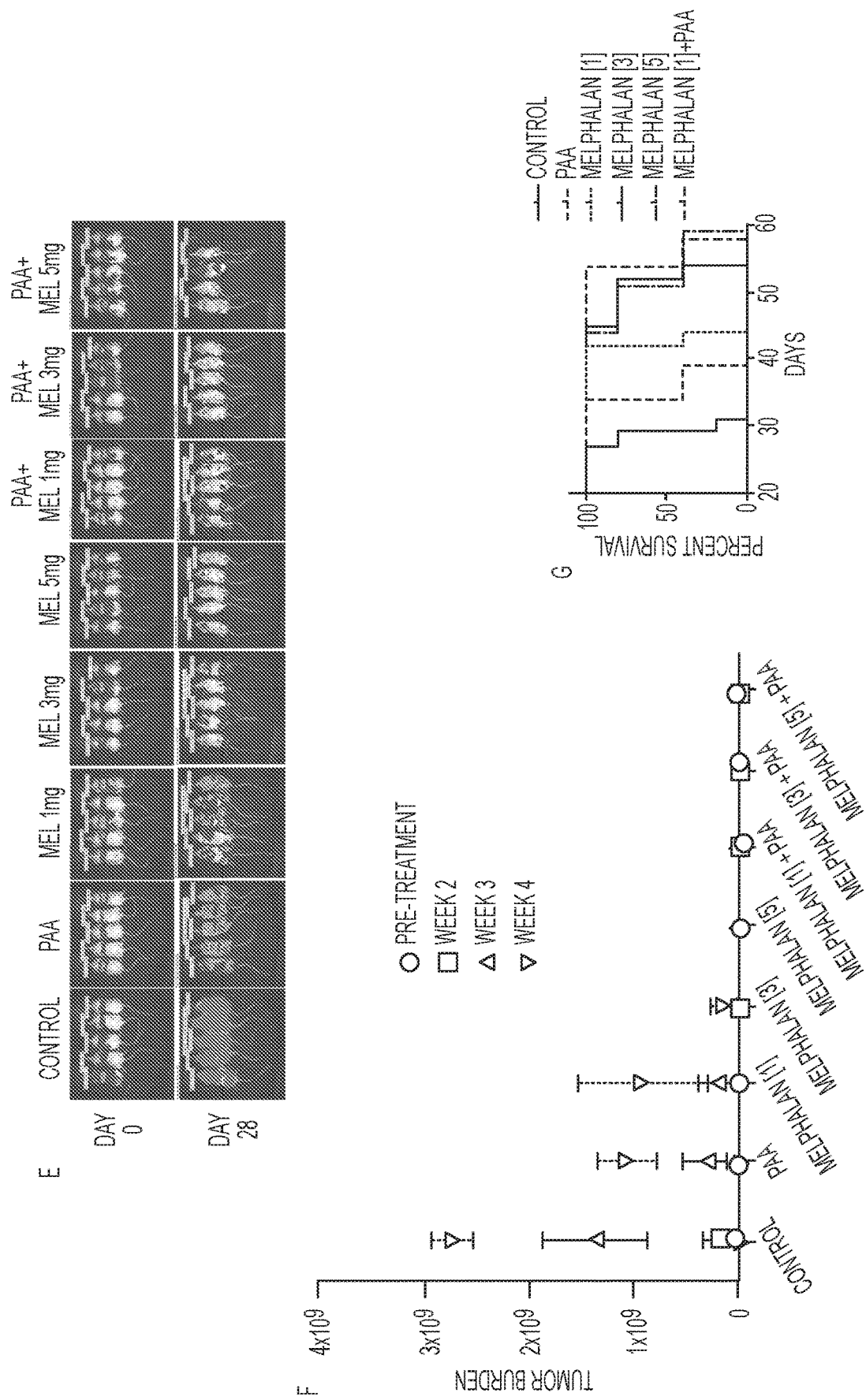
Figure 7:
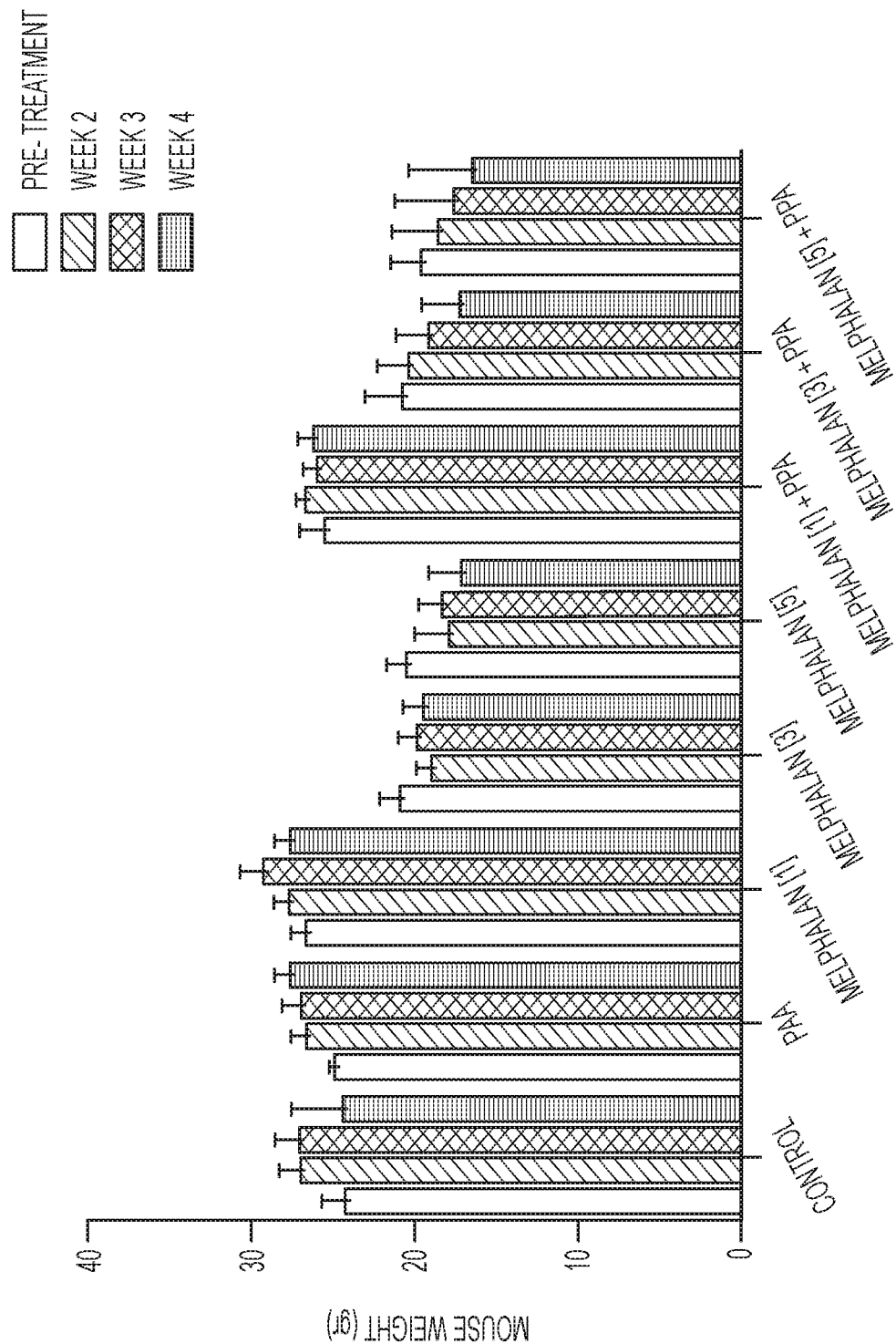
FIG. 7. Combination of PAA with melphalan does not change body weight. Six groups of ARP1 xenografted NOD.Cγ-Rag1 mice were treated with PAA and with or without melphalan (1, 3, and 5 mg/kg) and body weight was determined at the specified time.
Figure 8:
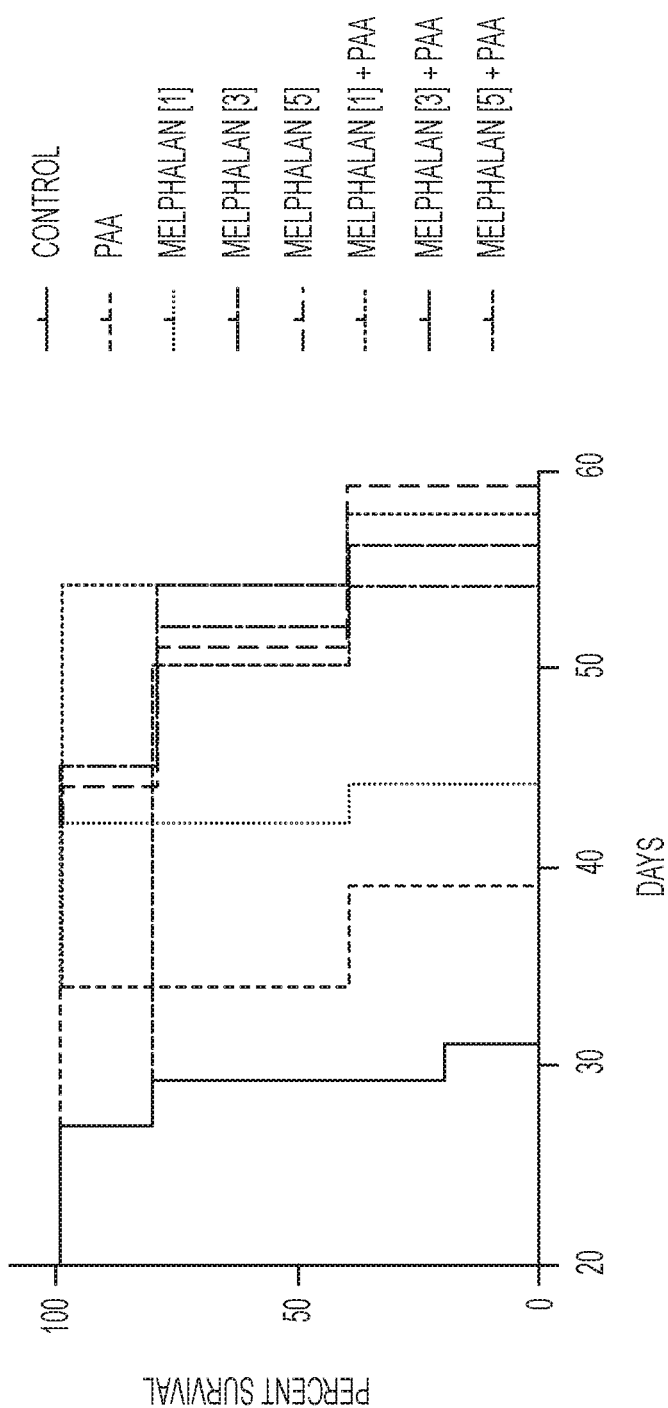
FIG. 8. Combination of PAA with melphalan increases MM mouse survival. An IVIS shows ARP1 cell growth in xenografted NOD.Cγ-Rag1 mice with or without PAA treatment (4 g/kg, i.p. once a day, 5 days a week for 3 weeks). Total flux after PAA treatment was normalized with pre-PAA treatment and indicates quantification of luciferase intensity of mice post-PAA treatment. ARP1 xenografted NOD.Cγ-Rag1 mice were treated with PAA or melphalan alone or in combination (1, 3, and 5 mg/kg). Total flux indicates quantification of luciferase intensity of mice pre- and post-PAA treatment at different time points.

The clinical objective of this study was to determine if PAA addition would allow a decrease in melphalan dose without losing its efficacy. Therefore, mice were treated with 3 different doses of melphalan (1, 3, and 5 mg/kg) plus PAA. Tumor burden at three weeks of treatment showed that single agent melphalan also at the lowest dose was able to inhibit tumor growth better than PAA alone (FIGS. 1E & F). Further, the presence of tumor at the highest dose of melphalan was detected only after four weeks confirming that the high dose had greater antitumor effect. In contrast, no difference in outcome was observed when melphalan was combined with PAA even at the lowest dose. Reduction of mouse weight was not observed suggesting lack of acute inflammation (FIG. 7). Tumor burden was almost undetectable in mice treated with any of the three combinational therapies (FIG. 1F). Survival curves confirmed that high doses of single agent melphalan (3 and 5 mg/kg) extended MM mouse survival (FIG. 1G) better than PAA alone. However, the combination of PAA with lowdose melphalan (1 mg/kg) extended MM mouse survival significantly compared with low-dose melphalan alone (FIG. 1G; p<0.05). Importantly, no survival differences were observed between low and high doses of melphalan when given in combination with PAA (FIG. 1G and FIG. 8).

Figures 9A, 9B:
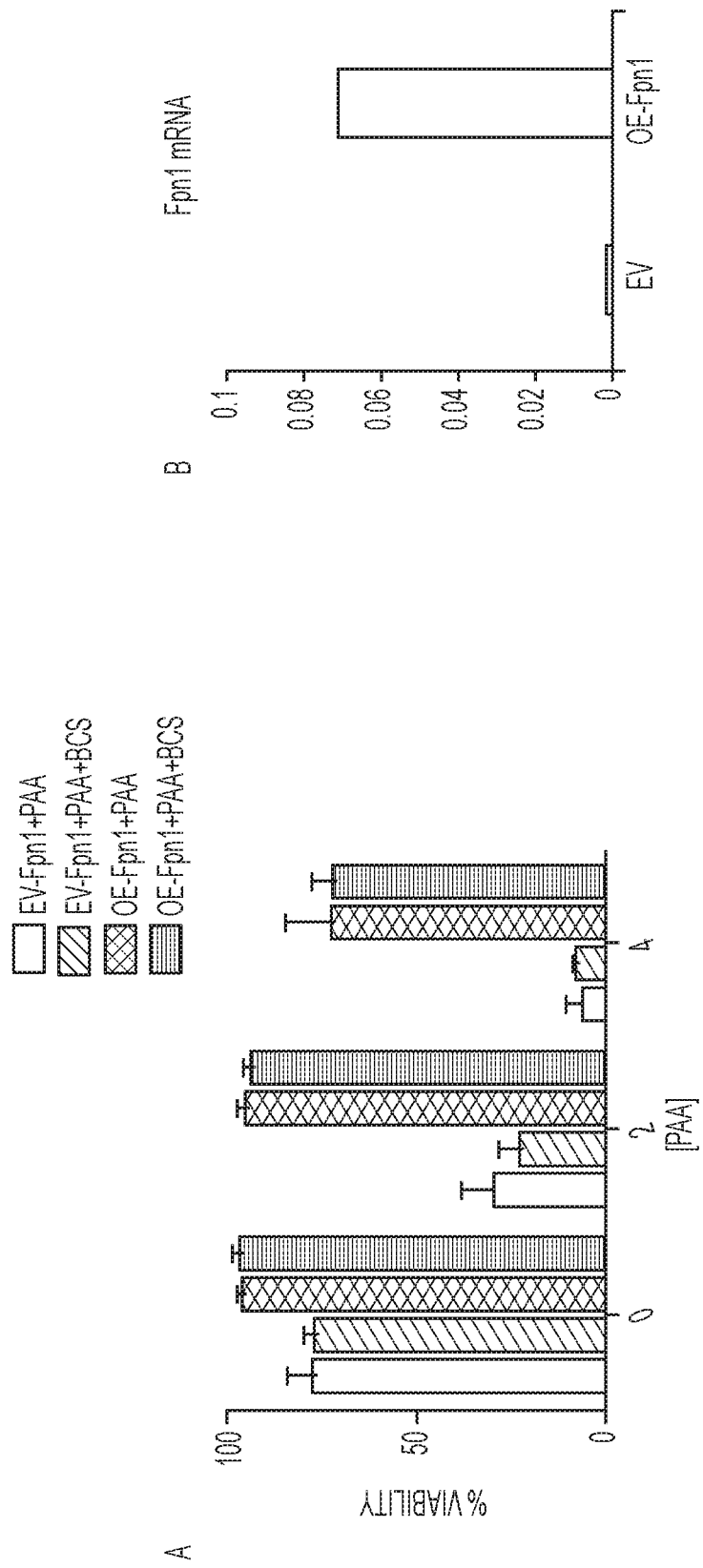
FIGS. 9A-9B. BCS does not block PAA anti-cancer activity.

The Therapeutic Effect of Pharmacological Ascorbic Acid Depends on Cellular Iron and Reactive Oxygen Species We subsequently asked whether PAA was selectively killing MM tumor cells by generating ROS, we treated OCI-MY5 MM wild-type (WT) cells with N-acetyl cystein (NAC) or catalase. Both catalase and NAC are commonly used anti-oxidant agents. OCI-MY5 cells pretreated with NAC and catalase became resistant to PAA even at high doses (FIG. 2A). Importantly, adding deferoxamine (DFO), an iron chelator, to OCI-MY5 cells before PAA treatment was also sufficient to prevent PAA-induced cellular death (FIG. 2A) but bathocuproinedisulfonic acid disodium salt (BCS), a selective copper chelator, was not able to block cellular death (FIG. 9A) suggesting that iron is essential for PAA to achieve its anti-cancer activity. We reasoned that high cytosolic iron would catalyze PAA auto-oxidation leading to cell death. Because MM tumor cells have a higher labile iron pool (LIP) than nontumor cells, we hypothesized that PAA anti-cancer effect is dependent on LIP. We have previously showed that Fpn1, the only known mammalian iron exporter, is down-regulated in MM cells at the expression levels leading to higher LIP. We next sought to determine if higher Fpn1 levels in MM tumor cells could also block cell death mediated by PAA. We overexpressed and confirmed Fpn1 expression by qRT-PCR in OCI-MY5 cells (FIG. 9B). We noticed that 4 mM PAA was able to kill OCI-MY5 EV cells but not to OE-Fpn1 cells (FIG. 2B).

Five-fold greater concentration of PAA (20 mM) was required to successfully kill OE-Fpn1 cells.

Since the overexpression of Fpn1 in OCI-MY5 cells inhibits PAA anti-cancer activity, we next explored whether iron supplementation was able to restore sensitivity to PAA. Iron pre-treatment caused a rapid decrease in cells viability of OCI-MY5 EV cells (FIG. 2C) and the same effect was obtained in OCI-MY5 OE-Fpn1 cells (FIG. 2D). Consistent with our hypothesis, DFO, an iron chelator, (FIGS. 2C & D) abolished the ability of PAA to reduce cells viability in both EV and OE-Fpn1 OCI-MY5 cells pre-treated with iron.

Figures 3A, 3B:
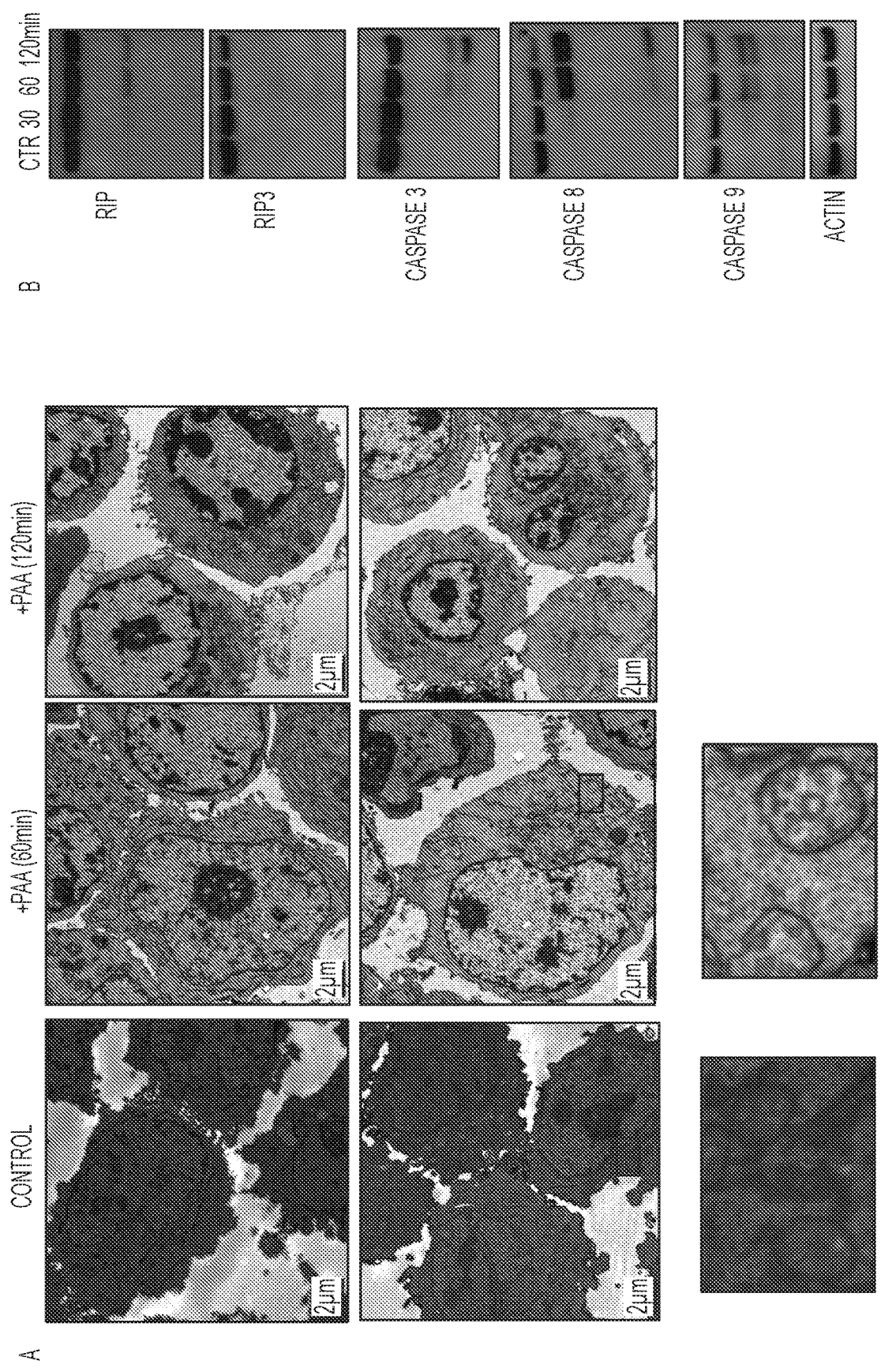
FIGS. 3A-3B. Pharmacologic ascorbic acid induces mitochondria-mediated apoptosis in MM cells.

Pharmacological Ascorbic Acid Induces Both Necrosis and Apoptosis in Myeloma Cells To determine the type of cell death induced by PAA, we performed transmission electron microscopy (TEM) experiments. FIG. 3A showed that in OCI-MY5 WT cells incubated with 4 mM PAA for one hour and then left for another two hours, PAA induced early necrosis (FIG. 3A, 60 mins) followed by late apoptosis (FIG. 3A, 120 mins). OCI-MY5 WT cells untreated appeared healthy and the mitochondria had visible cristae. However, once cells were treated with PAA, mitochondria started to swell and the cristae disappeared, but no remarkable chromatin condensation was identified (FIG. 3A, 60 mins). In a later stage, chromatin condensation was seen in almost all cells, while mitochondrial membranes disappeared and most of cellular organelles were degraded (FIG. 3A, 120 mins), consistent with apoptosis. Apoptosis can be induced by extrinsic stimuli through membrane death receptors or by intrinsic stimuli through mitochondrial signaling pathways (Hengartner, M. O. The biochemistry of apoptosis. Nature 407, 770-776 (2000); Kurokawa, M. & Kornbluth, S. Caspases and kinases in a death grip. Cell 138, 838-854 (2009)). Our results further indicated that PAA induced mitochondria-mediated apoptosis with marked increase in caspases 3, 8, and 9 activity (FIG. 3B). All three caspases were cleaved after 60 mins post-PAA treatment. However, because necrosis was seen at earlier time points after PAA treatment we also hypothesized that extrinsic stimuli might be involved in PAA-mediated cell death and we tested the activation of receptor interacting protein kinase 1 and 3 (RIP1 and RIP3) 24. FIG. 3B indicated that RIP1 and RIP3 were cleaved.

Figure 4A:
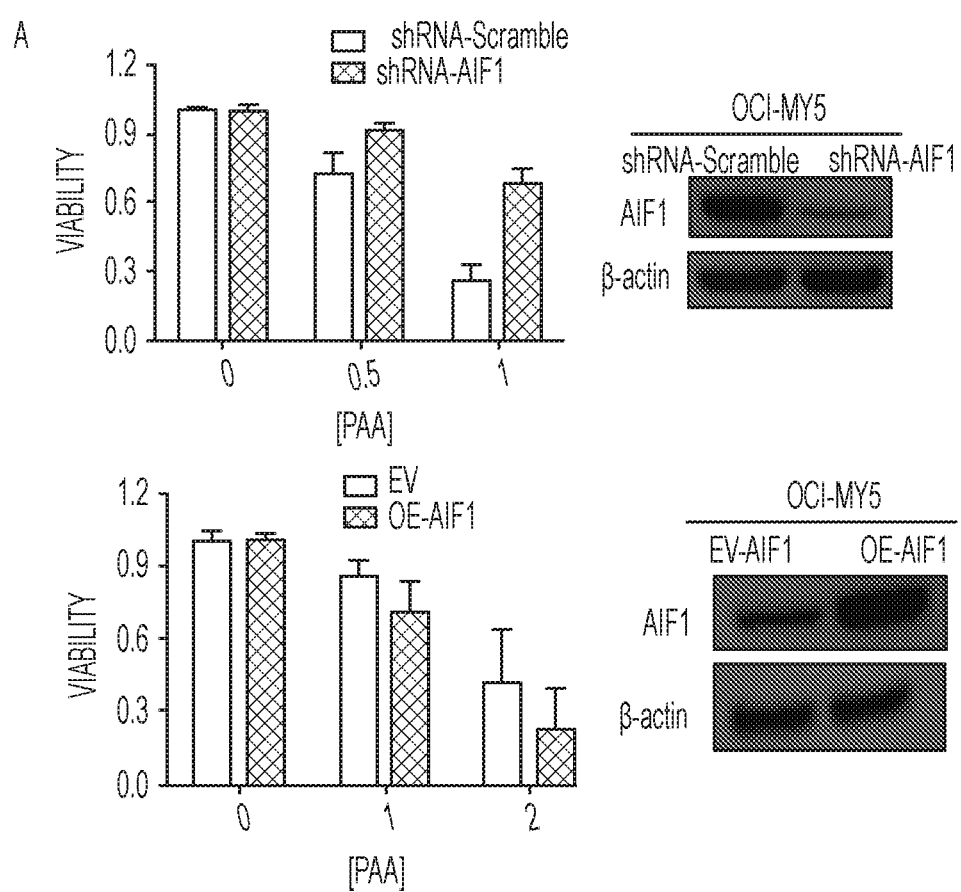
FIGS. 4A-4E. Pharmacologic ascorbic acid induces AIF1 release from mitochondria.
Figure 4B:
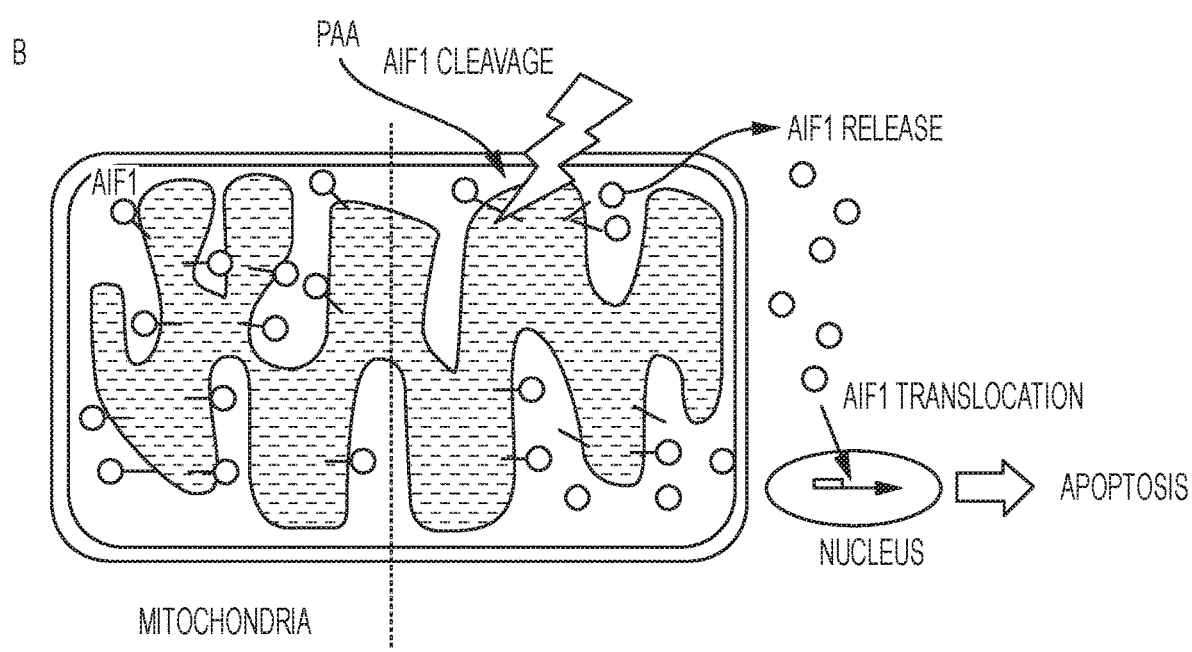
Figure 4C:
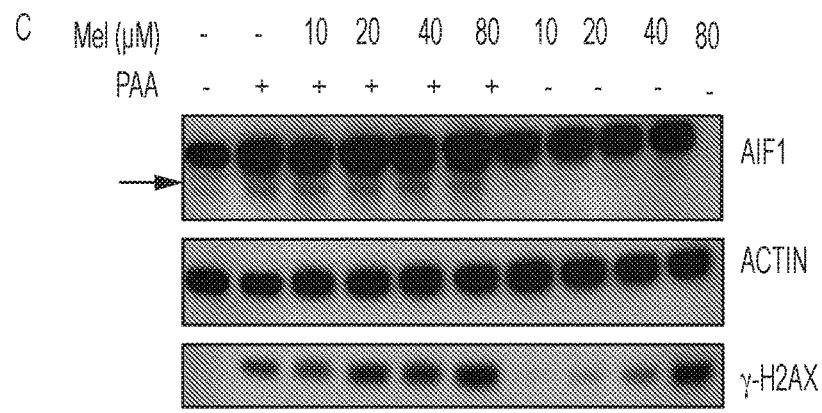
Figures 4D, 4E:
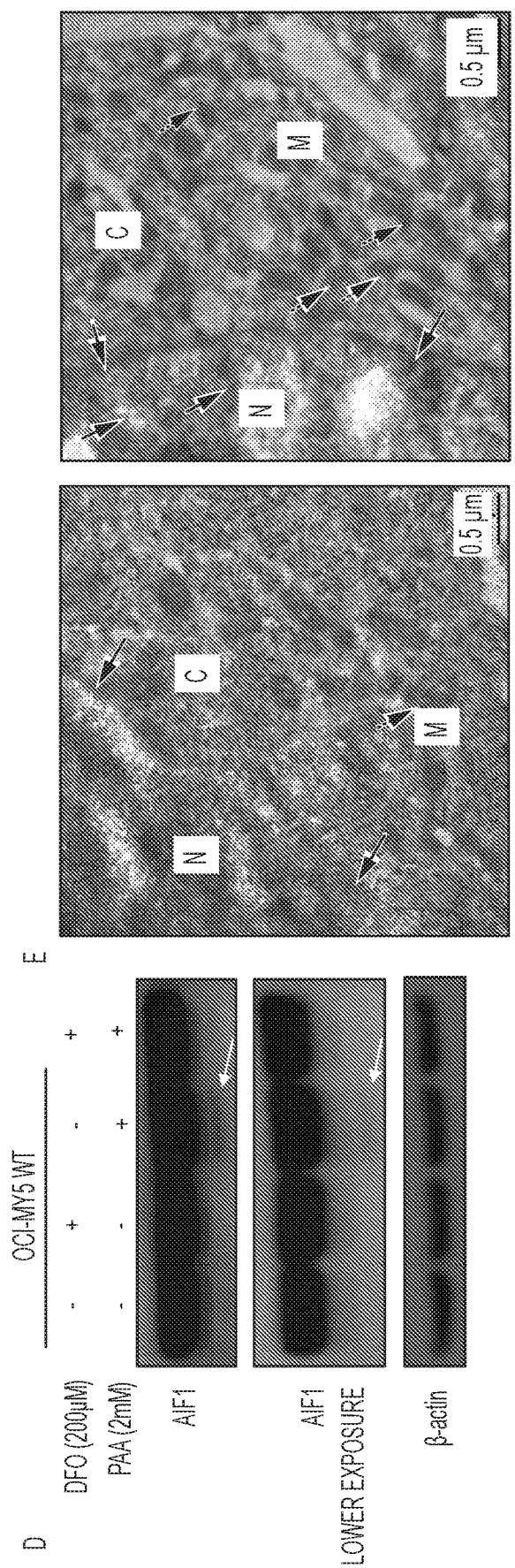

Apoptosis-Inducing Factor 1 Plays a Critical Role in Pharmacological Ascorbic Acid-Induced Myeloma Cell Death We subsequently tried to determine the molecular pathway by which PAA induced mitochondria-mediated apoptosis. Our hypothesis was that increased mitochondrial permeabilization was the trigger for the death signal transduction machinery. We focused our attention on apoptosis-inducing factor 1 (AIF1), because AIF1 induces cell death in a caspase-dependent and caspase-independent manners (Nikoletopoulou, V., Markaki, M., Palikaras, K. & Tavernarakis, N. Crosstalk between apoptosis, necrosis and autophagy. Biochimica et biophysica acta 1833, 3448-3459 (2013)). We firstly evaluate if PAA induced MM cell death depends on AIF1 at least partially. We generated OCI-MY5 cells with AIF1 knockdown (shRNA-AIF1) or overexpression (OE-AIF1). The viability of OCI-MY5 AIF1-shRNA cells (FIG. 4A, top bar graph) was significantly higher than those cells expressing scrambled sequence after PAA treatment (FIG. 4A, top bar graph), while OCI-MY5 OE-AIF1showed significantly less viability (FIG. 4A, bottom bar graph) than cells transfected with empty vector (EV) when treated with PAA (FIG. 4A, bottom bar graph). It is widely accepted that AIF1 must be cleaved and released from the mitochondria to the cytoplasm and then translocate to the nucleus to induce chromatolysis leading to cell death (FIG. 4B) (Sevrioukova, I. F. Apoptosis-inducing factor: structure, function, and redox regulation. Antioxidants & redox signaling 14, 2545-2579 (2011)). We thus examined if PAA induced AIF1 cleavage. OCI-MY5 cells treated with PAA showed an increase in the AIF1 cleaved form by western blotting (FIG. 4C). Interestingly, melphalan was not able to induce AIF1 cleavage in OCI-MY5 cells (FIG. 4C). We hypothesized that the AIF1 cleavage was mediated by PAA reacting with LIP to form ROS. Thus, we incubated OCI-MY5 cells with or without DFO followed by PAA treatment. AIF1 was not cleaved after PAA incubation in OCI-MY5 cells pretreated with DFO confirming the crucial role of LIP in this process (FIG. 4D, white arrow). We also tested the level of phosphorylated γ-H2AX, a biomarker for DNA double-stand breaks, after PAA and melphalan treatment, and determined that PAA and high dose of melphalan induced γ-H2AX. However, a lower dose of melphalan with PAA was also able to induce γ-H2AX (FIG. 4C). These data support our earlier in vivo data (FIG. 1F) that combination of PAA and melphalan at lower dose inhibits tumor formation as the same level or greater than melphalan alone. Cellular localization of AIF1 was examined by immunolabeling electron microscope with and without PAA treatment in OCI-MY5 cells. This staining revealed that AIF1 localizes not only in the mitochondria, as seen in untreated cells (FIG. 4E, left panel), but also in cytoplasm and nuclei in PAA-treated OCI-MY5 cells (FIG. 4E, right panel). These results indicate that PAA by reacting with LIP and generating ROS induces mitochondria-mediated apoptosis in which AIF1 cleavage is important for cell death.

Discussion

High-dose vitamin C has been studies in multiple cancers and has shown controversial clinical effects (Cameron, E. & Pauling, L. Supplemental ascorbate in the supportive treatment of cancer: Prolongation of survival times in terminal human cancer. Proceedings of the National Academy of Sciences of the United States of America 73, 3685-3689 (1976); Cameron, E. & Pauling, L. Supplemental ascorbate in the supportive treatment of cancer: reevaluation of prolongation of survival times in terminal human cancer. Proceedings of the National Academy of Sciences of the United States of America 75, 4538-4542 (1978); Creagan, E. T., et al. Failure of high-dose vitamin C (ascorbic acid) therapy to benefit patients with advanced cancer. A controlled trial. The New England journal of medicine 301, 687-690 (1979); Moertel, C. G., et al. High-dose vitamin C versus placebo in the treatment of patients with advanced cancer who have had no prior chemotherapy. A randomized double-blind comparison. The New England journal of medicine 312, 137-141 (1985)). The contradictory clinical results can be at least partially explained by different routes of vitamin C administration applied, i.e., either orally or intravenously. Recent reports indicate that a certain ROS concentration is required for high-dose vitamin C to induce cytotoxicity in cancer cells. The generation of ascorbyl- and $H_2O_2$ radicals by PAA increases ROS stress in cancer cells. These studies including preclinical and clinical were performed in solid tumors, such as glioblastoma, pancreatic cancer, ovarian cancer, prostate cancer, hepatoma, colon cancer, mesothelioma, breast cancer, bladder cancer, and neuroblastoma. Reports are lacking to show that PAA can be used as a pro-oxidant drug in the treatment of "liquid" tumors, where tumor cells are surrounded by blood. This environmental difference between solid tumor and blood cancer has the potential to influence the PAA efficacy on cancer cell death even when given at high doses, because ascorbic acid generated ROS are much easier permeabilized in liquid tumor than in solid tumor. In this study, we now report for the first time that PAA is very efficacious in killing MM cells in vitro and in vivo models, which generated levels of 20-40 mM ascorbate and 500 nM ascorbyl radicals after intraperitoneal administration of 4 g ascorbate per kilogram of body weight 38, in xenograft MM mice. These data suggest that PAA may be a better therapeutic applied to blood cancers than solid tumors because of the communication advantage between tumor cells and blood plasma.

We have shown that FPN1 regulates iron export in MM cells and LIP in vitro and in vivo. In addition, ferritin also regulates LIP by sequestering free iron in an oxidized form to prevent formation of free radicals. Our preliminary data show that overexpression of FPN1 in MM cell line OCI-MY5 results in increased viability compared to wild type cells after PAA treatment. We hypothesize that Fpn1 expressing MM cells are less sensitive to PAA because their cytosolic iron content is reduced by Fpn1. To test if resistance to PAA is indeed due to low cytosolic iron content, we depleted cytosolic iron by pre-incubating cells with an iron chelator, deferoxamine (DFO). ARP1 MM cells pre-treated with DFO (200 µM, 3 hrs) followed by PAA treatment showed a higher viability than cells not pre-treated with DFO. These results strongly suggest that the mechanism of PAA killing of MM cells is indeed iron-dependent. In addition, Fpn1 is significantly down-regulated in CD138+ primary MM cells, while the iron importer, transferrin receptor 1, is significantly upregulated in CD138+ MM cells compared to normal plasma cells, further supporting that MM cells have higher iron content than non-tumor cells. PAA showed increased killing of MM cells derived from almost all primary MM patients and smoldering MM, but not from MGUS patients. These results suggest that PAA administration in SMM may be able to prevent progression to symptomatic MM.

Though ROS and $H_2O_2$ are well known factors mediating PAA-induced cancer cell death, a single molecular mechanism cannot explain these observations, because multiple pathways are involved in the downstream effects of ROS and $H_2O_2$. Necrosis, casepase-dependent and caspase-independent apoptosis, and autophagy were reported in ascorbate induced cell death in different types of cancer. A recent study by Yun and colleagues demonstrated that vitamin C selectively kills KRAS and BRAF mutant colorectal cancer cells by targeting GAPDH, but spares normal cells (Yun, J., et al. Vitamin C selectively kills KRAS and BRAF mutant colorectal cancer cells by targeting GAPDH. Science 350, 1391-1396 (2015)). Other molecular mechanisms including ATP depletion and ATM-AMPK signaling have been reported to explain PAA-induced cell death. In this study, TEM data indicate that mitochondrial morphology and structure are significantly altered after PAA treatment. Furthermore, AIF1 was originally discovered as an intermembrane space (IMS) component of mitochondria and characterized as a proapoptotic gene. Therefore, we focused on AIF1 to explain PAA-induced MM cell death. The proapoptotic AIF1 or truncated AIF1 (tAIF) is cleaved from the full-length AIF1 by calpains and/or cathepsins after a caspase-independent cell death insult. tAIF moves from the mitochondria to the cytosol and nucleus, where it initiates chromatolysis and caspase-dependent and caspase-independent cell death. Our data show that PAA increases AIF1 cleavage and translocation from mitochondria to cytoplasm and nucleus. Overexpression of AIF1 in MM cells increases while knock-down of AIF1 prevents PAA-induced MM cell death, indicating that AIF1 plays a critical role in mediating PAA-induced MM cell death. Because the mitochondrial apoptogenic factors such as cytochrome c and Bcl-2 family proteins are also important for the activation of caspases, future work will have to determine if AIF1 is the major pathway related to PAA activity in cancer cells as well as the exact relationship with other mitochondrial apotogenetic factors. In addition, the necrosis and apoptosis markers, such as RIP1/3 and caspases 3/8/9, are cleaved after PAA administration. It is therefore possible that PAA activates caspase 8 resulting in RIP1 cleavage and necrosis evidenced by strong caspase 8 cleavage after a short-term treatment with PAA.

High oxidative stress and DNA damage activity are increased, while the anti-oxidant enzyme levels are decreased in MM patients. Several free radical drugs, such as $As_2O_3$ and ascorbic acid, have been used to treat MM, in which $As_2O_3$ generates ROS while ascorbic acid serves as an anti-oxidant agent. In MM preclinical and clinical studies, ascorbate was used as an adjunct drug and showed controversial results (Perrone, G., et al. Ascorbic acid inhibits antitumor activity of bortezomib in vivo. Leukemia 23, 1679-1686 (2009); Harvey, R. D., Nettles, J., Wang, B., Sun, S. Y. & Lonial, S. Commentary on Perrone et al.: "Vitamin C: not for breakfast anymore . . . if you have myeloma". Leukemia 23, 1939-1940 (2009); Held, L. A., et al. A Phase I study of arsenic trioxide (Trisenox), ascorbic acid, and bortezomib (Velcade) combination therapy in patients with relapsed/refractory multiple myeloma. Cancer investigation 31, 172-176 (2013); Sharma, M., et al. A randomized phase 2 trial of a preparative regimen of bortezomib, high-dose melphalan, arsenic trioxide, and ascorbic acid. Cancer 118, 2507-2515 (2012); Nakano, A., et al. Delayed treatment with vitamin C and N-acetyl-L-cysteine protects Schwann cells without compromising the anti-myeloma activity of bortezomib. International journal of hematology 93, 727-735 (2011); Takahashi, S. Combination therapy with arsenic trioxide for hematological malignancies. Anti-cancer agents in medicinal chemistry 10, 504-510 (2010); Sharma, A., Tripathi, M., Satyam, A. & Kumar, L. Study of antioxidant levels in patients with multiple myeloma. Leukemia & lymphoma 50, 809-815 (2009); Qazilbash, M. H., et al. Arsenic trioxide with ascorbic acid and high-dose melphalan: results of a phase II randomized trial. Biology of blood and marrow transplantation. Journal of the American Society for Blood and Marrow Transplantation 14, 1401-1407 (2008)). However, none of these tests used pharmacological doses of ascorbate and intravenous administration. It has been reported that ascorbate directly inactivates proteasome inhibitor by forming a tight but reversible complex through its vicinal diol group (Perrone, G., et al. Ascorbic acid inhibits antitumor activity of bortezomib in vivo. Leukemia 23, 1679-1686 (2009); Harvey, R. D., Nettles, J., Wang, B., Sun, S. Y. & Lonial, S. Commentary on Perrone et al.: "Vitamin C: not for breakfast anymore . . . if you have myeloma". Leukemia 23, 1939-1940 (2009)). This dose of ascorbate in the combination with bortezomib is at a physiological level which has anti-oxidant effect. It will be interesting to test if high dose ascorbate, which functions as a pro-oxidant agent, can increase bortezomib efficacy in MM treatment.

Our findings complement reported studies and further address the mechanism of action using clinical samples in which we observed that PAA only kill tumor cells with high iron content, suggesting that iron is the initiator of PAA cytotoxicity. In addition, combination of PAA with standard therapeutic drugs, such as melphalan, may significantly reduce the dose of melphalan needed, because high dose melphalan is very toxic not only to tumor cells but also to normal tissues, such as hematopoietic stem cell and epithelial cells in the gut. The efficacy of high dose melphalan by itself is clearly dose-dependent. Combined treatment of reduced dose melphalan with PAA achieved a significantly longer progression-free survival than the same dose of melphalan alone. These data also suggest that the bone marrow suppression induced by high-dose melphalan can be ameliorated by the combination of PAA with lower dose of melphalan because of the lack of toxicity of PAA on normal cells with low iron content.

EXAMPLE 2

Implication of Iron in Multiple Myeloma Tumor Biology and Progression

Multiple myeloma (MM) is a plasma cell neoplasm. Novel drugs, such as proteasome inhibitors and immunomodulatory agents, combined with Autologous Stem Cell Transplantation have led to complete remissions in a majority of newly diagnosed patients with MM. These treatments are not aimed at specific molecular targets and often result in increased toxicity and decreased therapeutic efficacy, therefore, development of novel target therapies is urgent. Recent reports have shown that iron induces cancer development and is associated with progression and poor prognosis in several malignancies. It has recently been discovered that iron plays an important role in MM tumor development and progression. In particular, it was observed that alterations of iron homeostasis are key metabolic changes in MM patients. Ferroportin 1 (Fpn1) expression, the only known iron efflux pump in mammalian cells, is significantly downregulated in MM cells compared with their normal counterparts. In normal cells, Fpn1 is mainly regulated post-translationally by hepcidin resulting in its degradation. Low expression of Fpn1 results in an increased labile iron pool in tumor cells. Importantly, low expression of Fpn1 has been linked to poor prognosis in primary MM samples using gene expression profiles. Similar outcomes have been reported in breast cancer studies.

The present Example characterizes iron homeostasis in MM cells and its role in tumor cell development and progression. Five novel discoveries have laid the groundwork for these studies: (1) Multiple signature genes related to iron homeostasis are dysregulated in MM. (2) The expression of Fpn1 is downregulated in MM cells and its downregulation is negatively correlated with patient outcome. (3) Fpn1 regulates intracellular iron in MM cells using in vitro and in vivo models. (4) Restoring expression of Fpn1 suppresses MM cell growth both in vitro and in vivo. And (5) Pharmacological modulation of MM cellular iron prevents tumor progression in vivo. The results suggest that iron is not only a hallmark for disease progression but also could serve as a target for therapy in MM.

Introduction

Multiple Myeloma (MM) is a plasma cell tumor and the second most common blood-derived malignancy in the US. Clinical outcomes of patients with MM are extremely heterogeneous, with survival ranging from only several months to more than 15 years. In addition to genetic heterogeneity, increasing evidence suggests that iron metabolism in cancer cells accounts for the divergent clinical outcomes. The expression of proteins involved in maintaining cellular iron balance was analyzed and it was discovered that iron homeostatic mechanisms are altered in MM. Particularly, in different MM stages, Fpn1 is less expressed leading to high intracellular labile iron pool (LIP). Fpn1 is the receptor for the hormone hepcidin (Hamp). Increased hepcidin expression induces impaired iron utilization and results in normochromic/normocytic anemia in many diseases, including MM. Fpn1 expression also is negatively correlated with patient outcomes. Fpn1 encodes a multiple transmembrane domain protein that transfers cellular iron to the plasma, which regulates the exit of iron from cell. It has been reported that Fpn1 is downregulated in breast cancer cells when compared to their normal counterparts (Pinnix Z K, Miller L D, Wang W, D'Agostino R, Jr., Kute T, Willingham M C, et al. Ferroportin and iron regulation in breast cancer progression and prognosis. Science translational medicine 2010 Aug. 4; 2(43): 43ra56). Consistent with the low levels of Fpn1 expression, the breast cancer cells showed a markedly higher LIP than the non-malignant breast epithelial cells. Iron metabolism is emerging as a key metabolic hallmark of cancer. In normal cells, Fpn1 is mainly regulated post-translationally by hepcidin resulting in its degradation. Studies suggest that iron dysregulated is not only a biomarker for prognosis but also could serve as a target for treatment in MM. Cancer cells tend to enhance cellular iron availability, resulting in increased cellular proliferation. MM cells exhibit different iron needs when compared to normal differentiated plasma cells. The studies described in this application focus on how iron distribution is regulated and how its changes affect MM tumor cells biology. Further, because of these metabolic alterations, targeting the specific iron needs of MM cells can be of therapeutic value.

The studies in this Example investigate the molecular basis of iron regulation in MM cells and its therapeutic implication. The importance of iron in MM cells is critical because subtle changes in iron balance influence tumor development, progression and treatment in multiple ways. Finally, information gained from this study is relevant to dysregulated iron metabolism in other forms of cancer.

Figures 10, 11:
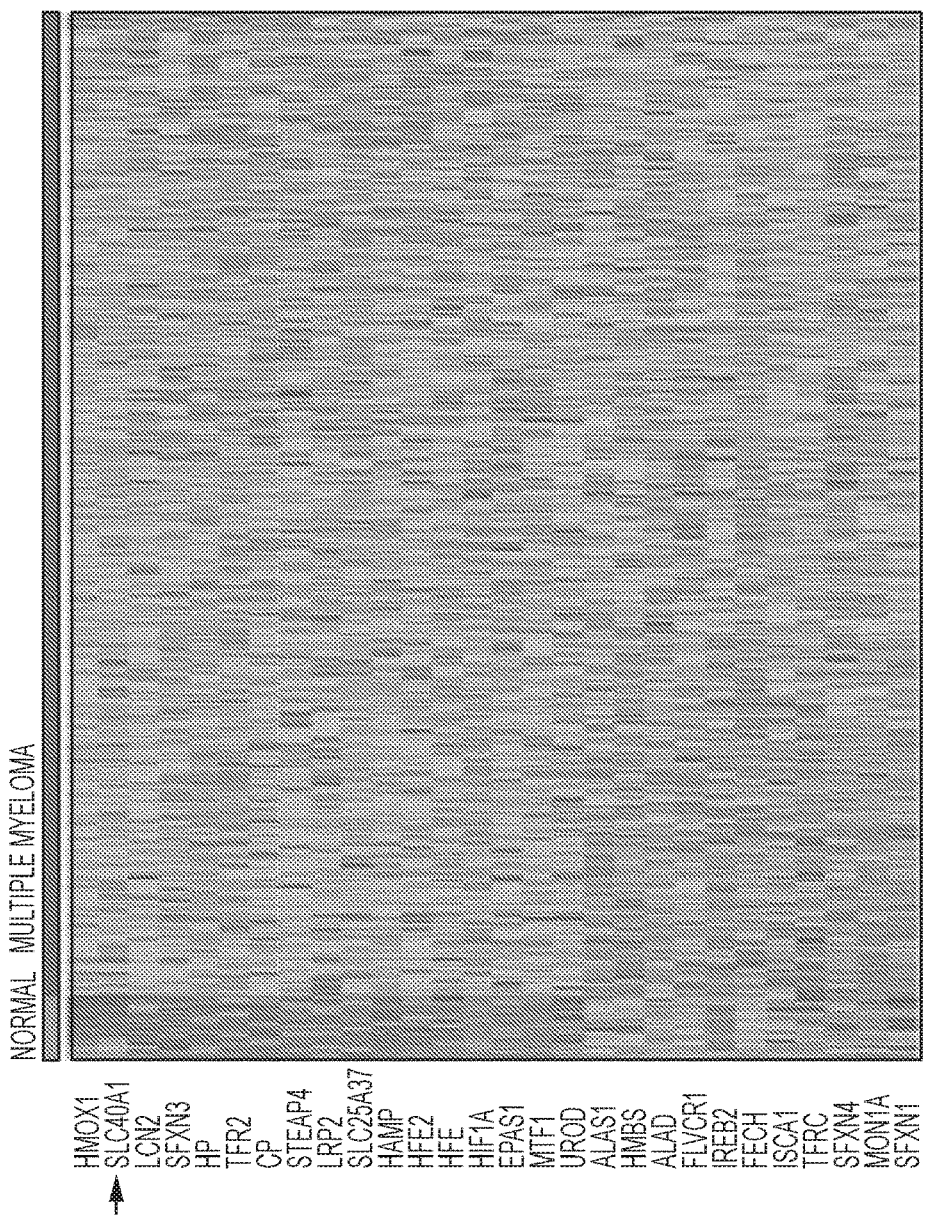
FIG. 10. Iron Homeostasis is altered in Myeloma Patients. Supervised cluster analysis of iron signature genes in normal plasma (Normal) and Multiple myeloma cells. Arrow indicates SLC40A1, the Fpn1 gene.
FIG. 11: Ferroportin 1 is Downregulated in MM Tumor Cells. Scatter plots depict the Affymetrix signal of Fpn1 in normal plasma cells (NPCs), MGUS, newly diagnosed multiple myeloma (MM; TT2 cohort), and multiple myeloma cell lines (MMCL). One-way ANOVA was performed and identified the $p<0.0001$ among these four groups. The p value presented in the figure was obtained by comparison between NPC and indicated group, respectively.

Specific treatment for the dysregulated iron metabolism in cancer cells is lacking, because the critical regulation mechanisms of iron homeostasis remain largely unknown. Iron homeostasis is altered in multiple myeloma cells. Gene expression analysis of iron-regulatory genes in the MM malignant cells from 351 newly diagnosed patients (Total Therapy 2, TT2) shows a deregulation in cellular iron homeostasis signaling when compared to 22 normal plasma cells. Of the 61 signature genes related to iron metabolism (131 probe sets), 29 genes were significantly deregulated by comparison of normal plasma cells to MM samples (FIG. 10). The expression of these 29 genes was then correlated with patient outcome in the TT2 cohort and Fpn1 was found to be the gene mostly associated with an inferior outcome in MM. Fpn1 expression was significantly lower in plasma cells derived from MM patients compared to those derived from patients with monoclonal gammopathy of undetermined significance (MGUS, benign monoclonal gammmopathy) and healthy donors (p<0.0001, FIG. 11).

Figures 12A, 12B:
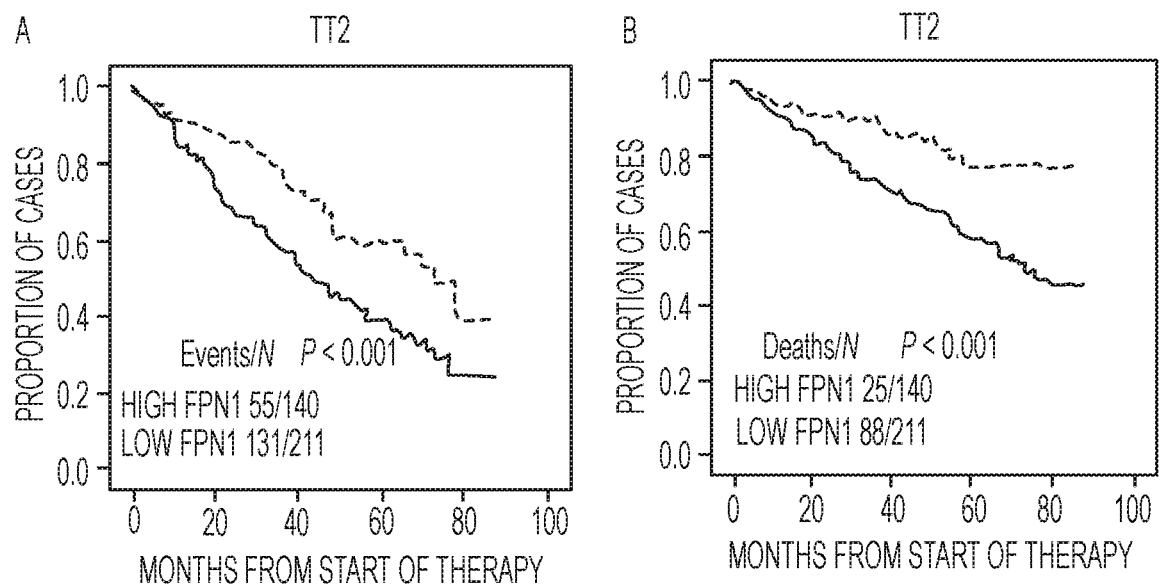
FIGS. 12A and 12B. Low Expression of Ferroportin 1 is Linked to Poor Patients Outcome in MM.

Low-expression of Fpn1 is linked to poor outcome in MM. Survival analysis was performed using Kaplan-Meier test in three different data sets. Consistent with the low Fpn1 expression in the aggressive MM subgroups, decreased Fpn1 in the 351 TT2 cohort showed that about 60% of such cases showed a short event-free survival (EFS) (FIG. 12A, p<0.001) and also an inferior overall survival (OS) (p<0.001, FIG. 12B). Similar results were observed from HOVON65 49 and APEX50 cohorts including 288 newly diagnosed MM samples and 264 relapsed MM samples respectively (Gu Z, Wang H, Xia J, Yang Y, Jin Z, Xu H, et al. Decreased ferroportin promotes myeloma cell growth and osteoclast differentiation. Cancer research 2015 Jun. 1; 75(11): 2211-2221).

Figure 13:
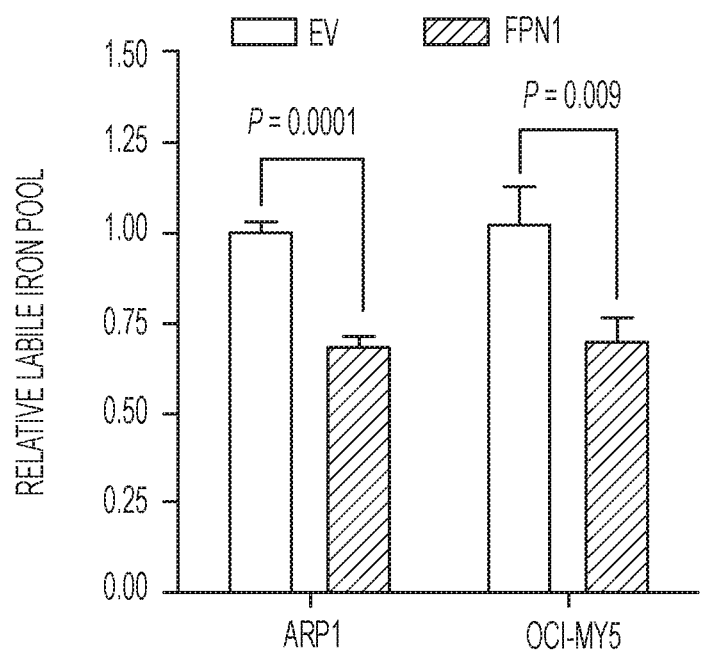
FIG. 13. Ferroportin 1 Regulates MM Intracellular Iron. Cells overexpressing Fpn1 (FPN1) have lower intracellular LIP than wild type cells (EV).

Fpn1 regulates intracellular iron in vitro and in vivo in MM cells. To test whether Fpn1 regulates iron efflux in MM cells, the labile iron pool (LIP) was measured with fluorescent metallosensor calcein. ARP1 and OCI-MY5 cells overexpressing Fpn1 had significantly lower LIP compared to their EV counterparts (FIG. 13).

Figures 14A, 14B:
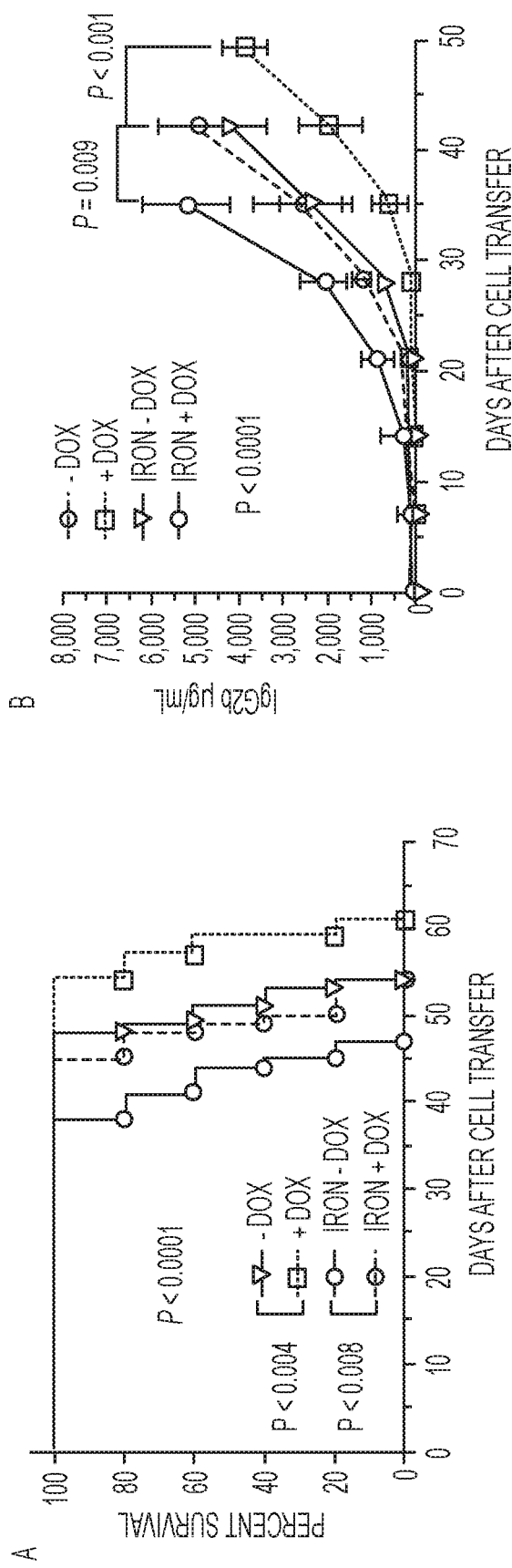
FIGS. 14A and 14B. Iron Retention Promotes Tumor Development and Progression. 5TGM1-Fpn1 KaLwRij mice were administrated with or without doxycycline and dextran-iron as indicated 1 week after cell injection.
Figure 15:
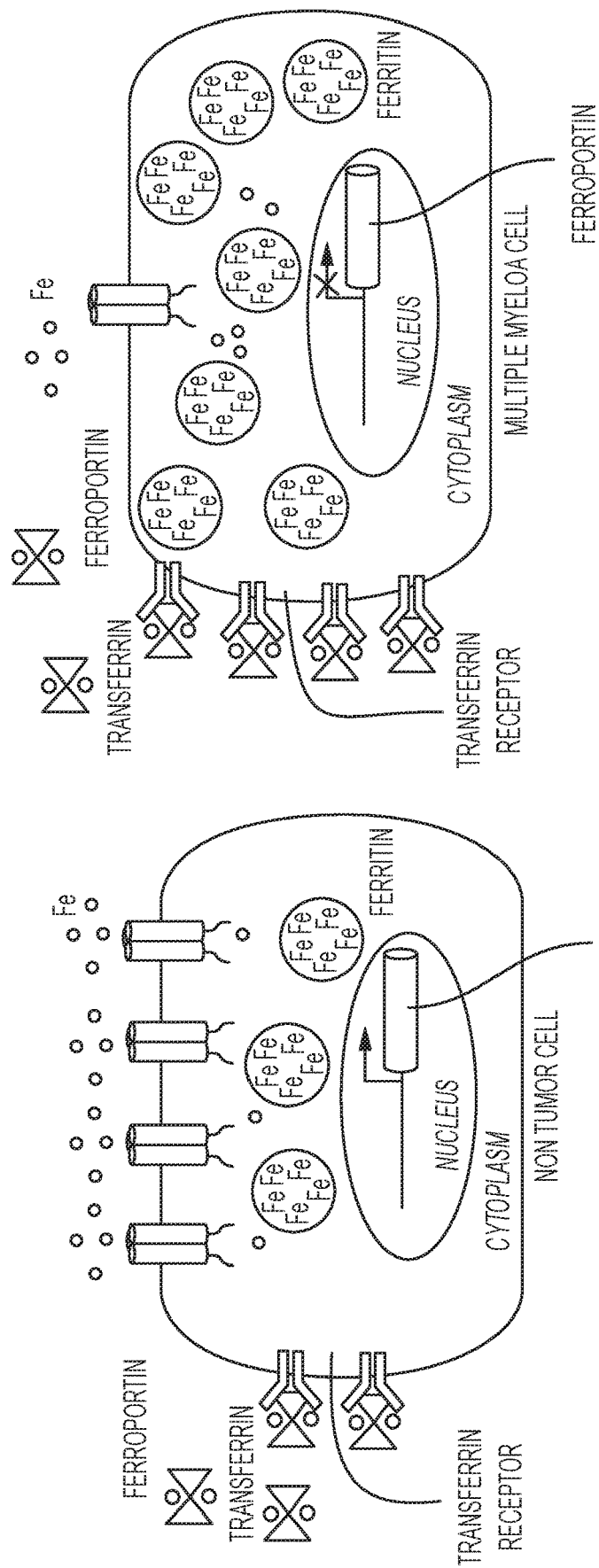
FIG. 15. Iron Uptake and Efflux in non-Tumor and Multiple Myeloma Tumor Cell. Left: Non-tumor cells show low levels of transferrin receptor (iron uptake) and high levels of ferroportin (iron efflux) to maintain low levels of cytosolic iron (ferritin, iron storage). Right: Multiple Myeloma cells show higher level of transferrin receptor and lower level of Ferroportin 1 leading to higher cytosolic iron (ferritin) and free iron.

Iron retention promotes tumor development and progression in vivo. The 5TGM1-KaLwRij model was further analyzed to test the role of Fpn1-inducing iron retention on MM progression in vivo. Real-time PCR confirmed that 5TGM1 MM cells had much lower expression of Fpn1 than normal bone marrow plasma cells in KaLwRij mice. The coding region of Fpn1 cDNA in a doxycycline inducible lentiviral construct was stably transduced with lentivirus into the 5TGM1 cells, in which the expression of Fpn1 was conditionally induced upon addition of doxycycline. One week after transduced 5TGM1 cell injection, mice were administrated doxycycline and dextran-iron to increase systemic iron content in the mouse body. Overexpression of Fpn1 (induced by administration of doxycycline, Dox) significantly extended mouse survival (FIG. 14A, +DOX open square) compared to non-induced (−Dox triangle) group. Tumor burden in this group was also reduced, assessed by mouse serum IgG2b level (FIG. 14B, compare open circle with triangle). To confirm whether inhibition of tumor formation by Fpn1 is because it enhances iron efflux, iron was given in the drinking water to the above mice to reverse the effect. 5TGM1 mice that received iron accelerated tumor progression resulting in a shorter survival and higher tumor burden than those without iron in their drinking water (FIG. 14A, compare closed circle with triangle). Importantly, the effect of iron administration on MM progression could be blocked if Fpn1 is overexpressed in MM cells (FIG. 14A, compare square with open circle). All findings, to date, show that MM cells exhibit different iron needs when compared to normal differentiated plasma cells, as schematized in FIG. 15.

Determination of How Myeloma Tumor Cells Uptake Iron From the Bone Marrow Microenvironment.

Previous studies conducted in MM and in different blood and solid tumors show that cancer cells differ from their non-malignant counterparts in the levels and activity of multiple proteins involved in iron homeostasis. These changes result in increased intracellular iron levels facilitating to tumor proliferation. Despite the mechanisms that tumor cells retain intracellular iron, particularly in MM, remain unclear, the possible changes in iron uptake may allow MM cells to accumulate iron from the microenvironment. To depict these crucial changes in iron uptake the following three possibilities are investigated: (1) if the transferrin pathway is critical to increase intracellular iron in MM cells; (2) if a transferrin-independent iron transport mechanism, such as lipocalin-2, is involved in iron accumulation in MM cells; and (3) if macrophages are the predominant iron reservoir.

Figure 16:
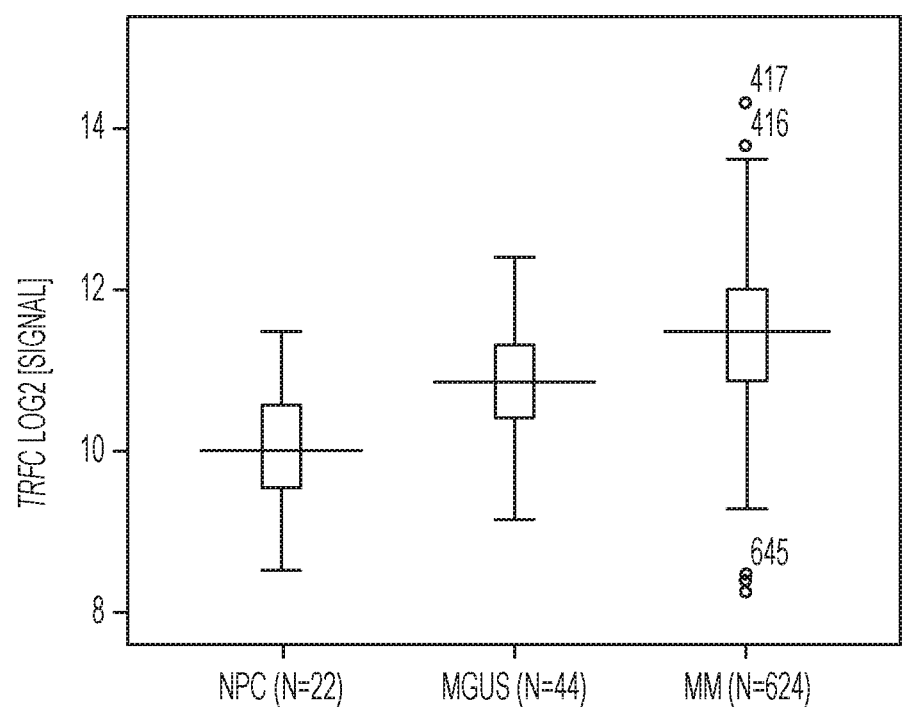
FIG. 16. Transferrin Receptor is Upregulated in MM Tumor Cells. Affymetrix signal of TFRC in normal plasma cells (NPC), MGUS and multiple myeloma (MM).

Determine if transferrin pathway is critical for iron uptake in Multiple Myeloma tumor cells. The transferrin pathway plays a critical role for iron acquisition by most cells. In the body, iron circulates bound to transferrin (TF) which binds two atoms of ferric iron. Once the TF-iron complex is formed, it binds to the transferrin receptor 1 (TFRC) present at the plasma membrane in many cells, then the new complex TF-iron-TFRC is internalized by endocytosis. After iron is released in the cytoplasm, the TF-TFRC complex recycles back to the plasma membrane. The levels of TF and TFRC in normal cells are relatively low to maintain a small pool of labile iron, however some findings have reported that tumor cells have increased expression of TFRC and this increase could be associated with patients' poor prognosis. It was recently reported that upregulation of TFRC may not only enhance the iron uptake but also promote cell survival by activating other cellular signaling pathways in breast cancer. Gene expression profiles show that MM cells have higher expression of TFRC (FIG. 16) when compared with normal plasma cells (NPC). TFRC also appears unregulated in MGUS samples, a pre-MM disease, when compared to normal plasma cells. Thus, it is hypothesized that TFRC is upregulated in MM tumor cells to maintain higher pool of labile iron for MM development and progression.

To ascertain the role of TFRC in iron uptake by MM tumor cells, a lentiviral vector expressing TFRC shRNA is used to knockdown TFRC expression. Two shRNA targeting different regions of the TFRC transcript are designed and one scramble shRNA is used as a control. RT-PCR and western blotting confirms the shRNA-mediated efficiency suppression of TFRC. Using real-time PCR and western blotting, any changes in the expression of components related to iron metabolism such as iron storage factor ferritin and Fpn1 after TFRC knockdown are detected. These changes are examined in the presence or absence of an external iron source such as diferric transferrin and/or ferric ammonium sulfate. Diferric transferrin and ferric ammonium sulfate are commercially available and widely used. Labile iron pool are measured using fluorescent metallosensor calcein. It is anticipated that labile iron pool is constant or decreased in the knockdown cells for TFRC if TFRC is a crucial for iron uptake; if TFRC is not the only protein responsible for iron uptake, an LIP increase in the TFRC shRNA cells when iron is added in the cell culture media is also expected. If this is the case, other(s) protein(s) could be responsible for the increase of cellular iron pool. The cell survival effect of TFRC suppression by colony formation assay is also analyzed. ARP1 and OCI-MY5 transduced with scramble or TFRC shRNA lentiviruses are mixed with RPMI1640 media containing 10% FBS and 0.33% agar and layered on the top of the base layer of 0.5% agar in each well of 6-well plate. Half wells are treated with diferric transferrin and ferric ammonium sulfate. Colony numbers are counted after approximately 2-3 weeks. All plates are pictured under a microscope and overall numbers of colonies counted and quantified by Image J software.

Figure 17:
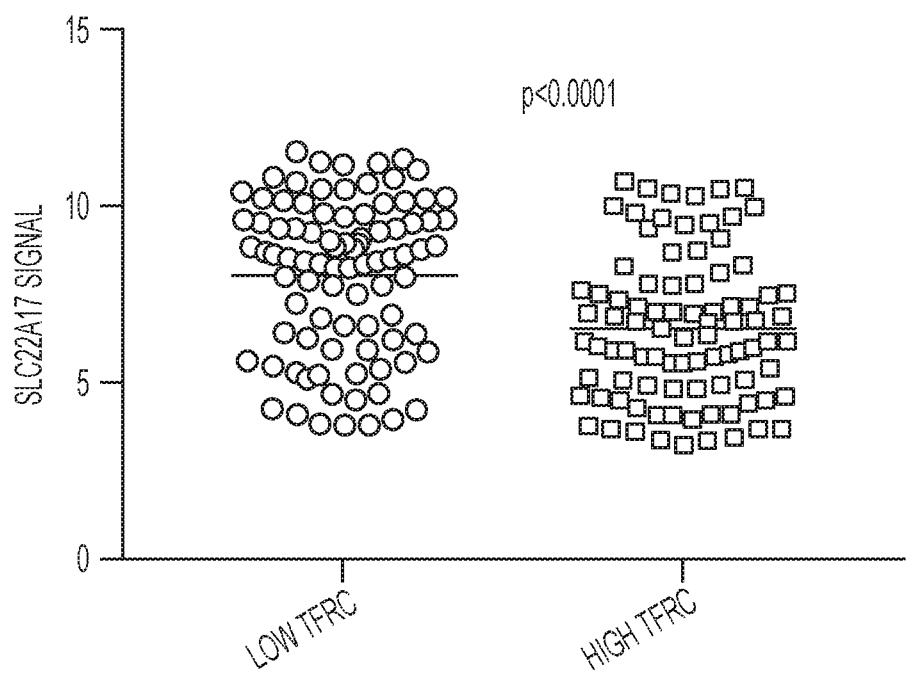
FIG. 17. Repression of Transferrin Receptor Leads to SLC22A17 Upregulation in MM. Affymetrix signal of SLC22A17, lipocalin-2 receptor, in MM patients' tumor cells either with high or low TFRC expression.

Determine if a transferrin-independent mechanism is involved in iron uptake in Multiple Myeloma cells. Recent studies pointed to a role of lipocalin-2 in facilitating tumorigenesis in various solid cancers and trafficking iron into cells in a transferrin receptor-independent manner. To properly traffic iron, lipocalin-2 forms a complex with iron-enriched mammalian siderophores (holo-lipocalin-2) and binds to its cell surface receptor, SLC22A17. Once internalized lipocalin-2 releases iron leading to a higher labile iron pool. It is important to point out that SLC22A17 also binds apo-lipocalin-2 (a form not bound to siderophore) and in this case lipocalin-2 in the cytoplasm acts as an iron chelator by transferring intracellular iron to the extracellular compartment with consequent reduction of labile iron pool in the cytoplasm. Interestingly, the gene expression profile data from primary MM samples showed that TFRC expression was not upregulated in all MM samples as might be expected to maintain higher cytosolic iron (FIG. 10). This observation suggests that MM tumor cells are also able to uptake iron in a transferrin-independent manner. To test if this is true, the SLC22A17 expression level in the two populations respectively with high and low TFRC was analyzed. The results indicated that SLC22A17 was upregulated in the MM tumor cells with low TFRC, while SLC22A17 was downregulated in those highly expressing TFRC (FIG. 17).

To determine the role of SLC22A17 and lipocalin-2 in MM iron uptake, the following experiment is performed. First, the expression of SLC22A17 is measured in ARP1 and OCI-MY5 cells with or without knockdown of TFRC by RT-PCR and western blotting. It is expected that MM cells silenced TFRC will upregulate SLC22A17 expression if lipocalin-2 is involved in iron uptake. It is then determined if MM cells silenced TFRC are able to increase their cellular iron concentration after incubation with lipocalin-2-iron-siderophore complex. Recombinant mouse lipocalin-2 is synthetized as a glutathione S-transferase fusion protein in the BL21 strain of Escherichia coli (Stratagene, La Jolla, Calif.). Briefly, ferric sulfate is added to the culture medium at 50 µM. The protein is isolated using glutathione-Sepharose 4B beads (Amersham Biosciences), eluted with thrombin (Sigma-Aldrich), and purified with gel filtration (Superdex 75; Amersham Biosciences). Recombinant protein is mixed with iron-loaded and iron-unloaded forms of a bacterial siderophore enterochelin (EMC Microcollections, Tubingen, Germany) in phosphate-buffered saline at room temperature for 60 min. Unbound siderophore is removed with Microcon YM-10 (Millipore). The recombinant protein is added to the culture media of MM cells silenced TFRC. Cellular iron concentration will be measured by fluorescent metallosensor calcein. It is expected that MM cells with low expression of TFRC increases their iron content when incubated with the recombinant protein and conclude that TFRC is not the only responsible protein for iron uptake. An important control for these cells is the incubation with transferrin-iron because under these conditions only the control MM cells transduced with scramble lentiviruses are able to increase their labile iron pool but not the TFRC silenced MM cells.

Determine if bone marrow macrophages are the iron reservoir for Multiple Myeloma cells. MM cells are always in need of an iron reservoir in order to fulfill their higher metabolic demand and support their growth and progression. Under normal conditions, macrophages are considered the "specialized iron cells" because they are able to acquire, recycle, process, store and transport iron. Further, macrophages, including those in a malignant setting, exhibit a remarkable heterogeneity and functional plasticity by assuming an M1, iron sequestration and tumor repression, or M2, iron release and tumor promotion, phenotype. It is hypothesized that macrophages within MM bone marrow microenvironment are the strong candidate as an iron source for MM tumor cells. Interestingly, to support our hypothesis, several studies have reported that M2 macrophages are increased in MM patients. The following studies investigate whether macrophages can be co-cultured with the mouse cell line 5TGM1 and the iron trafficking under these conditions analyzed. For these experiments, bone marrow macrophages are isolated from C57BL/Kalwrij mice, which spontaneously develop myeloma in aging. These bone marrow macrophages, isolated from mouse femurs, are grown in RPMI 1640 media supplemented with 20% equine serum for 6 days and adherent cells are further cultured in RPMI 1640 with 20% fetal bovine serum and 30% L-cell conditioned medium. L-cell conditioned medium is used as source of colony stimulating factor required for macrophage differentiation. Later, macrophages are iron loaded with ferric ammonium citrate (FAC, 10 µM iron) for 18 hours and after that iron is washed away for 18 hours to allow them to export the iron via Fpn1. It is known that during iron loading in macrophages Fpn1 is synthetized and goes to the cell surface, and once iron is washed away from the medium Fpn1 exports iron out from cells. In the co-culture experiments, this phenomenon is taken advantage of to determine if the iron exported by Fpn1 from macrophages is taken by MM tumor cells. As a control that macrophages uptake and later release iron, ferritin levels, the cytosolic iron storage, are analyzed by western blotting and also intracellular iron pool will be measured by fluorescent calcein as described above. The anticipated result is that ferritin/iron pool is higher when macrophages are incubated with iron but rapidly decrease once iron is removed and Fpn1 starts exporting intracellular iron into the extracellular compartment.

Figure 18:
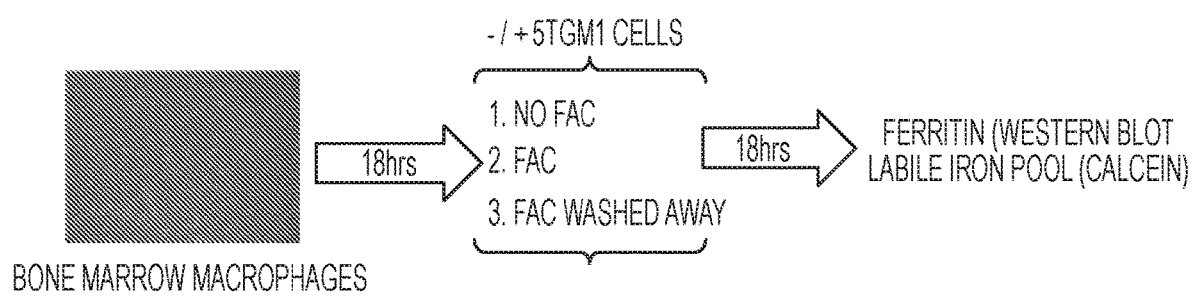
FIG. 18. Schematic Representation of Co-Culture Between Macrophages and MM Tumor Cell.

Once the experiments are completed that show that macrophages are able to increase and release their cytosolic iron; co-culture experiments with MM cells are performed. Briefly, three conditions are evaluated: (1) macrophages without iron; (2) macrophages incubated with iron; and (3) macrophages incubated with iron for 18 hours and later iron washed away for another 18 hours. This condition is run in duplicate with or without co-culture with 5TGM1 MM cells (FIG. 18). Cells are lysed and total RNA and proteins are extracted from each condition. It is expected that 5TGM1 cells uptake iron from macrophages, cytosolic ferritin and labile iron pool decreases in macrophages in which iron is washed away and co-cultured with 5TGM1 cells.

Determine the Mechanisms that Lead to Transcriptional Repression of Fpn1 in Multiple Myeloma Cells.

Figure 19A:
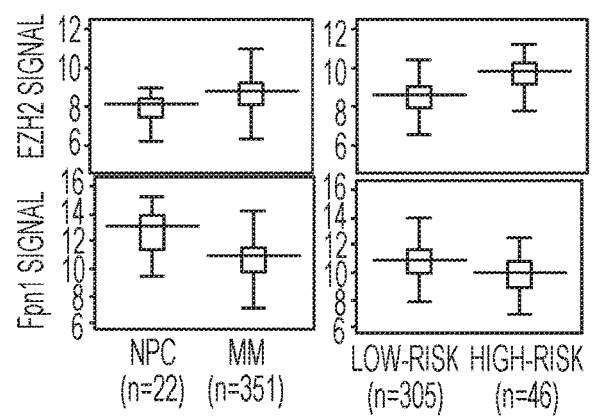
FIGS. 19A and 19B. Iron Retention Promotes Tumor Development and Progression.

Data described herein show that Fpn1 expression in MM cells is sharply downregulated and cytosolic iron is high. Regulation of Fpn1 at the translational and posttranslational level is well described but little is known about transcriptional regulation. Through a systemic analysis of microarray data, it was identified that the epigenetic modulator histone methyltransferase enhancer of zeste 2 (EZH2) was negatively correlated with the Fpn1 expression between normal with malignant plasma cells and low-risk and high-risk MM samples (FIG. 19A). Since Fpn1 functions are tightly related to iron and oxidative reaction, it also is hypothesized that cellular iron and oxidants might regulate Fpn1 transcription. To identify how Fpn1 is downregulated in MM cells, the following three possibilities are investigated: (1) if low Fpn1 is a consequence of epigenetic modification; (2) if high intracellular iron content is involved in regulation of Fpn1 expression; and (3) if high oxidants suppress Fpn1 transcription. These experiments determine how transcription of Fpn1 is regulated in MM cells and to offer insights for a potential clinical utility.

Figure 19B:
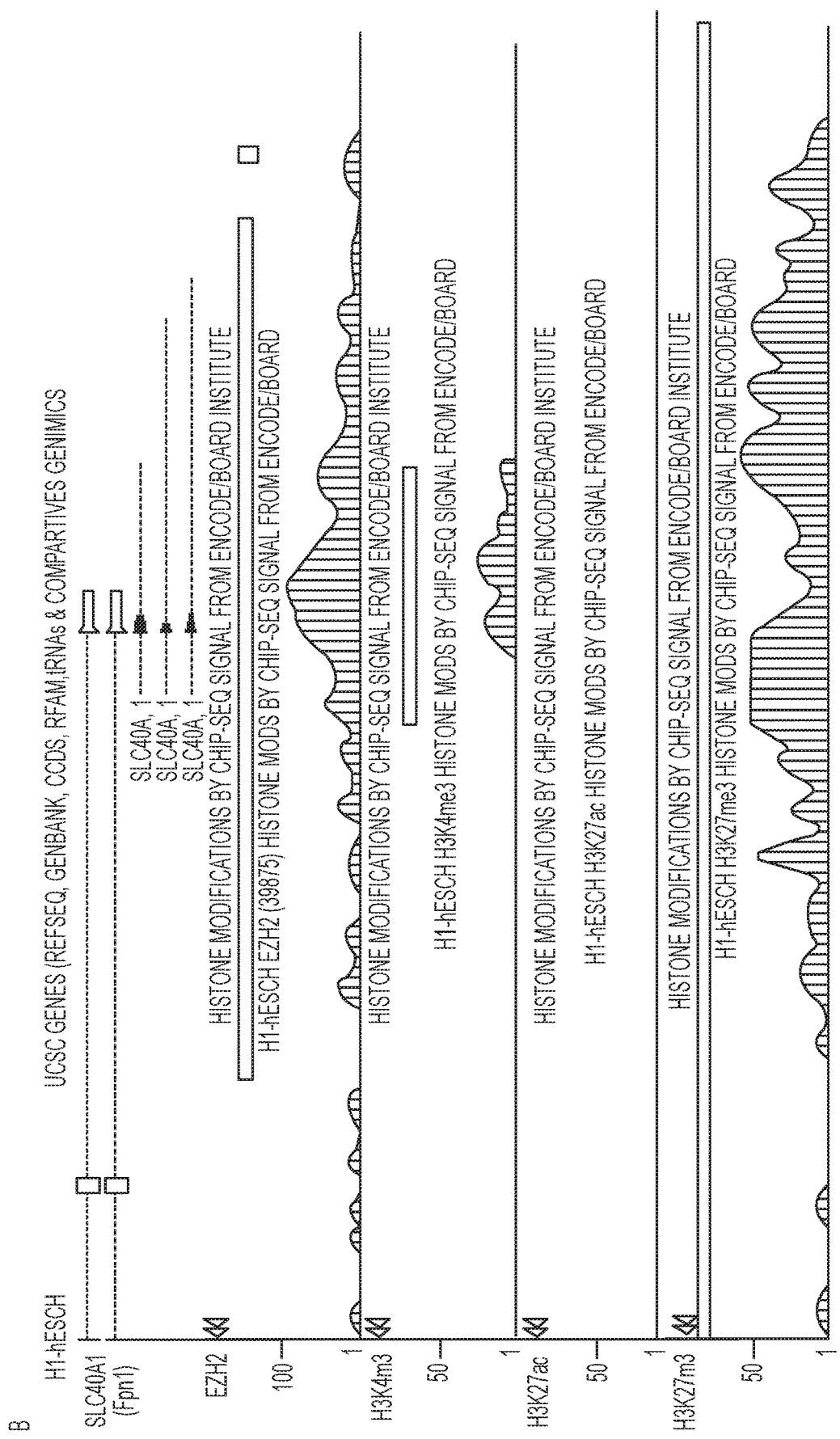

Determine if the histone methyltransferase enhancer of zeste 2 suppresses Fpn1 transcription. Several studies have shown that epigenetic modifications affecting specific pathways are important in the development and treatment of MM. In MM, some of the epigenetic effects result in repression of gene expression such as EZH2. EZH2 is a component of the Polycomb Repressive Complex 2 (PRC2) which includes EZH2, Suz12, and EED. It was found that EZH2 is dramatically upregulated and shows an inverse correlation with Fpn1 expression using gene expression profiles in primary MM samples (FIG. 19A). A putative EZH2 binding site at the Fpn1 promoter was further discovered, which overlaps with the mark of transcription start sites of active genes (H3K4m3) and the mark of transcriptional silencer H3K27me3, but not with the mark of transcriptional activator H3K27ac from the UCSC-ENCODE (FIG. 19B). This suggested that EZH2 may repress Fpn1 expression. To prove the involvement of EZH2 in Fpn1 regulation, MM cell lines ARP1 and OCI-MY5 are treated with commercially available EZH2 inhibitors and Fpn1 levels are analyzed by Real Time-PCR (RT-PCR).

The EZH2 inhibitors are an emerging class of therapeutics with anticancer properties and several studies show that they can decrease EZH2 protein levels. For these studies, the efficacy of DZNep and GSK343 are tested. DZNep has been shown to inhibit EZH2 protein expression and subsequently reduce the trimethylation of H3K27me3. GSK343 is a potent inhibitor of the histone H3K27 resulting in inhibition of EZH2 enzymatic activity. The above MM samples are treated with EZH2 inhibitors at two doses 5 and 10 µM for 24, 48 and 72 hours. For each dose and time of incubation, total RNA is isolated and Fpn1 is analyzed by RT-PCR. A critical control for this experiment is to monitor apoptosis because it has been shown that EZH2 inhibitors induce cell death via apoptosis. To eliminate the off-target issue, shRNA or CRISPR-Cas9 is used to silence EZH2 in MM cells and the expression of Fpn1 is analyzed by RT-PCR. It is expected that if EZH2 is involved in regulation of Fpn1 transcription, Fpn1 mRNA should be higher in cells treated with the inhibitors or knockdown of EZH2 when compared to the control cells. If this is the case, it is examined if EZH2 directly binds to the promoter region of Fpn1 by chromatin immunoprecipitation-qPCR (ChIP-qPCR) analysis. Cell extracts from the above described cells are crosslinked and sonicated to obtain DNA fragments with an average size of 0.3-0.5 kb. Protein-DNA complexes are immunoprecipitated using EZH2 antibody or IgG as a control, followed by the addition of Dynabeads protein. The relative amount of Fpn1 promoter fragments containing the EZH2 element is measured by real-time PCR with appropriate primers for human Fpn1. These data may provide a strong evidence that EZH2 is an epigenetic repressor of mFpn1in MM cells.

Determine if iron mediates Fpn1 mRNA decrease in MM cells. Iron impacts the expression profile in all eukaryotic cells. These effects can occur at the transcriptional and post transcriptional levels. Iron-mediated transcriptional regulation has been less studied. These experiments focus on determining if iron is involved in the downregulation of Fpn1 in MM cells. Fpn mRNA contains a 5' iron-response element (5'IRE) suggesting the Fpn1 is regulated post-transcriptionally. Others have shown that Fpn1 is transcriptionally upregulated in wild type macrophages when treated with iron. The gene expression profile is initially analyzed by microarray of iron-fed wild type ARP1 MM cells compared to untreated cells.

The following experimental procedures also are schematized in FIG. 20. First, those genes are examine that show evidence of 3' iron-responsive element (IRE) and an informatic approach is used to determine if sites are available on Fpn1 promoter. A few candidates are selected, these sites are mutated in a Fpn1 luciferase promoter construct. The iron-sensitive elements within the promoter are identified by making specific deletion(s). Second, it is explored as to which sites affect Fpn1 transcription. It is determined if, in an iron-dependent or iron-independent manner, the candidate repressor sites on a Fpn1 promoter by ChIP-qPCR analysis. Third, it is determined if knockdown of these possible repressors leads to increased expression of Fpn1.

Determine if Fpn1 expression in MM cells is suppressed by oxidants. It was determined that cytosolic iron in MM cells is higher (see FIG. 13). It is hypothesized that iron affects Fpn1 transcription through its effect on oxidation. An increase in oxidants can trigger alterations in transcription through a number of distinct mechanisms. Among the different possibilities, oxidation and reduction regulate transcription factors. First, it is determine if Fpn1 transcription in MM cells is altered by anti-oxidants. MM cell lines ARP1 and OCI-MY5 are incubated with iron and N-acetyl cysteine (NAC) or ascorbate and transcription of target genes assayed by RT-PCR or by reporter constructs.

Levels of $O_2.^-$ and $H_2O_2$ are measured using SOD-inhibitable and catalase-inhibitable dihydroethidium (DHE) and 2',7'-dichlorodihydrofluorescein diacetate (H2DCF-DA) oxidation. Mitochondrial localization of $O_2.^-$ signals are determined using MitoSOX Red oxidation and MitoTracker Green staining followed by confocal microscopy. Further confirmation that the dye oxidation is mediated by mitochondrial reactive oxygen species (ROS) utilizes adenoviruses overexpressing the mitochondrial form of manganese superoxide dismutase (Ad-MnSOD) or catalase (Ad-Mito-CAT); these recombinant adenoviruses are available through the Vector Core, University of Iowa. Adenovirus-mediated increases in enzymatic activity of SOD/catalase are assayed (Radiation and Free Radical Research Core, RFRRC, University of Iowa). If the anti-oxidants increase Fpn1, then it can be concluded that iron is acting through modification of redox status.

Determine if hepcidin is responsible for Fpn1 transcriptional repression. It is known that hepcidin binds to Fpn1 and induces its internalization and degradation and it has also been reported that serologic hepcidin levels are higher in MM patients than healthy controls. It is important to take into account that gene expression profile showed that hepcidin expression (HAMP, see FIG. 10) is decreased; however, this result does not preclude that hepcidin does not regulate Fpn1 but only suggests that hepcidin seen in patients' sera does not come from tumor cells. Therefore, it is hypothesized that hepcidin by inducing Fpn1 internalization lead also to transcription repression. The present studies determine if decreased transcription of Fpn1 results from the loss of cell surface Fpn1 by hepcidin. Previously it has been shown that cells treated with dynasore, an inhibitor of dynamin-mediated internalization or expression of a dominant negative K44A dynamin mutant lacking of the GTPase activity prevents Fpn1 internalization after hepcidin binding.

The first set of experiments are done to verify that in ARP1 and OCI-MY5 MM cell lines expressing Fpn1-GFP (GFP is integrated in the Fpn gene) and dynamin mutant K44A, Fpn1 is not internalized after incubation of hepcidin by immunofluorescence and western blotting. It is predicted that the results will confirm that dynamin is necessary for hepcidin-mediated Fpn1 internalization in MM cells. Hepcidin is add to MM cells expressing Fpn1-GFP and dynamin K44A or treated with dynasore, and it is determined if endogenous Fpn1 transcription increases at different time courses (FIG. 21). If Fpn1 levels do not change, it can be concluded that hepcidin does not control Fpn1 transcription in MM cells. If Fpn1 levels decrease further, it can be concluded that hepcidin is involved in the transcriptional repression of Fpn1 in MM cells. An important control is required to prove that hepcidin is involved in Fpn1 downregulation. Fpn1 is measured in cells treated with dynasore or expressing dynamin K44A in the absence of hepcidin to rule out blocking cellular dynamin-mediated internalization does not interfere with Fpn1 transcription.

Determine if Pharmacological Cellular Iron Modulations Serve as New Therapeutic Approaches in Multiple Myeloma.

Data show that Fpn1 overexpression inhibits tumor growth in a xenografted MM mouse model. These results suggest that modulating intracellular iron may be used as a therapeutic approach for MM. In the present experiments, both MM cell lines and primary MM samples are used to develop novel treatment strategies by pharmacological regulating iron homeostasis or "utilizing" high cytosolic iron content.

Determine if direct iron chelation inhibits tumor growth in a xenografted MM mouse model. One way to regulate cytosolic iron in MM cells is the direct chelation of iron. Previous studies have shown that desferrioxamine (DFO) has anti-cancer activity. However, these studies suggest that the utility of DFO is limited due to its poor cell membrane permeability and short half-life. Based on this information, it is proposed to use two relatively new iron chelators for our experiments, deferiprone (Ferriprox; ApoPharma, Toronto, Canada) and deferasirox (Exjade; Novartis, Basel, Switzerland). These iron chelators show more permeability and longer half-life when compared to DFO. Recently deferasirox was reported to inhibit the growth of myeloid leukemia cells in vitro and in vivo. It has also been determined that deferasirox inhibits the growth of human lung carcinoma xenographed mice.

The following experiments investigate the in vivo anti-cancer activity of deferasirox and deferiprone in xenografted MM mice. Human myeloma cell lines (ARP1 and OCI-MY5) with luciferase expression are injected subcutaneously into each flank of NOD-Rag/null gamma mice, tumor burdens will be monitored by bioluminescence assay and tumor volumes as described previously. Also, mice receive a single intraperitoneal injection with dextran-iron (250 μg per gram of body weight) to increase systemic iron content in the mouse body. Iron accumulation is monitored in these mice by measuring transferrin saturation using a commercially available kit. Increased transferrin saturation demonstrates that mice are absorbing iron. Subsequently, a group of mice will be treated with an iron chelator (40 mg/kg by oral gavage for 3 weeks). In this study, each group (control, iron, chelator 1, chelator 1+iron, chelator 2, chelator 2+iron) include 3 mice with 6 tumors, thus a total of 36 mice are required (6 groups×3 mice/group×2 cells lines). It is expected that direct iron chelation therapy delays tumor progression significantly in mice and that longer MM mouse survival occurs when compared to the group that was not treated with the chelators.

Determine if induction of ferroptosis inhibits tumor growth in a xenografted MM mouse model. Ferroptosis is a non-apoptotic form of cell death resulting from an iron-dependent accumulation of lipid ROS and it has been shown that ferroptosis facilitates the selective elimination of some tumor cells. It has been discovered that erastin, a cell permeable piperazinyl-quinazolinone compound, can induce ferroptosis by binding the mitochondrial voltage-dependent anion channels and altering its gating. Others have shown that ferroptosis can be inhibited by iron chelation. The following experiment investigate the anti-cancer activity of ferroptosis in a xenograft MM mouse model. It has been shown that MM cells have high cytosolic iron. Thus, it is hypothesized that injection of erastin induces MM cells ferroptosis with consequent delay in tumor progression and longer survival of MM mice. This proposed mechanism is summarized in FIG. 22. Data support this hypothesis: erastin treatment in MM cells (KMS11, ARK and ARP1) inhibits cellular growth and this effect can be reversed when cells are treated with a ferroptosis inhibitor ferrostatin (FIG. 23). Human MM cell lines with low mFpn1 (ARP1 and OCI-MY5) are injected subcutaneously into each flank of NOD-Rag/null gamma mice and tumor burden is monitored by bioluminescence assay and tumor volumes as described previously. Subsequently, the piperazine erastin (PE) water-soluble analog as previously described is used for in vivo injections 72. The PE is administrated subcutaneously at 60 mg/kg mouse weight twice per week for 2 weeks according to published studies and 12 mice (2 groups×3 mice/group×2 MM cell lines) are required for this study. The ferroptosis activity is monitored in mice by analyzing expression of ferropotosis marker PTGS2 by RT-PCR and the up- or downstream regulators, such as GPX4, p21, and p53 activation.

Determine if high cytosolic iron in MM patients is targetable by pharmacological ascorbic acid. Recent studies have shown that pharmacological ascorbic acid (PAA) selectively kills cancer cells while sparing the non-malignant cells (FIG. 24) in primary tumor samples. Further, it has been observed that PAA anticancer activity is iron-dependent. In fact, PAA was not able to decrease tumor burden in mice receiving injection at the same time with the iron chelator DFO (FIG. 25). Therefore, it is hypothesized that high iron in MM patients' tumor cells can be targetable by PAA anti-cancer activity. The present studies assess the efficacy of PAA in treating human primary MM cells collected at diagnosis and at relapse using the NOD-Rag1$^{null}$–hu mouse model. The NOD-Rag1$^{null}$–hu mouse model uniquely enables the study of human primary MM cells in a human bone marrow microenvironment. Briefly, human fetal long bones (tibias and femurs) from 18- to 21-week gestational fetuses are cut into two 10-mm pieces and implanted subcutaneously, on either the left or right side of the dorsum of NOD-Rag1$^{null}$ mice (one bone/mouse). Eight to 10 weeks after implantation of the bones, $1.5 \times 10^6$ CD138$^+$ MM cells sorted from newly diagnosed and relapsed patients (9 for each set) are injected directly into the human fetal bone. Each sample of myeloma cells are transferred to 3 NOD-Rag1$^{null}$–hu mice. Before injection of MM cells, qRT-PCR is performed to quantify the expression of Fpn1 in sorted CD138$^+$ MM cells and CD138$^-$ cells (non-malignant group). The efficacy of PAA alone and in combination with 2 common drugs currently used for MM treatment are studied: melphalan (Mel) and carfilzomib (Cfz). Six combinations for each clinical sample (untreated, PAA, Mel, Cfz, PAA+Mel and PAA+Cfz) are used. It is possible to purify $10 \times 10^6$ MM cells from a newly diagnosed MM sample or from a relapsed MM patient, respectively. Therefore, one sample is sufficient to cover the six combinations outlined above. Drug concentrations are PAA (4 mg/kg, twice a week, intraperitoneal, for 4 weeks), Mel (3 mg/kg, twice a week, intraperitoneal, on the same days as PAA administration for 4 weeks) and Cfz (3 mg/kg, twice a week, intraperitoneal, on the same days as PAA administration for 4 weeks). This study utilizes nine paired MM samples obtained at diagnosis and in relapse. A total of 108 mice with equal representation of mouse gender within each treatment group at each time point are required. Tumor growth is monitored by measuring human serum free light chains and M protein. Mice survival and time to tumor recurrence time are compared among the above outlined groups. Experiments are terminated when drug-treated mice reach complete remission for three months or when control mice become sick due to high tumor burden. The implanted femoral bone is be processed for histology and histomorphometry.

Statistical Analysis: Statistical analysis is performed to compare treatment groups within each experiment with respect to the proportion of mice. Power is estimated based on pairwise treatment group comparisons performed with a simpler one-sided Fisher's exact test at a single time point. Without treatment, the rate of tumor development or relapse is conservatively estimated to be 95%. Accordingly, the use of nine mice per group achieves 80% power to detect a difference of at least 60% (95% vs 35%) between the untreated and an active treatment group at the 5% significance level. In addition, time to relapse or time to B lymphoma is explored in a full analysis comparing treatment groups. Survival curves are constructed using the Kaplan-Meier method and compared between treatment groups using the log-rank test.

EXAMPLE 3

TRIP13: A Novel Gene in Multiple Myeloma Tumorigenesis and Progression

Multiple myeloma (MM) is a prototypical clonal B-cell malignancy with a terminally differentiated plasma-cell (PC) phenotype. Both genetics and exposure to carcinogens have been considered etiologic in MM. The monoclonal gammopathy of undetermined significance (MGUS) is a pre-MM disease and 1% of patients with MGUS progresses to MM annually. Smoldering multiple myeloma (SMM) is another asymptomatic plasma cell disorder that carries a higher risk of progression to MM compared to MGUS. MM is a difficult-to treat malignancy. High-dose chemotherapy, including tandem autotransplants, in recently diagnosed MM patients has led to complete remissions (CRs) in the large majority of newly diagnosed patients with MM. However, many patients achieving CR subsequently relapse, indicating that clinically significant minimal residual disease (MRD) persists in CR. Elucidating the mechanisms governing relapse is critical. Since little is known about these molecular mechanism, further research to identify the underlying driver genes is justified with the aim to develop novel targeted therapies. Thyroid Hormone Receptor Interactor Protein 13 (TRIP13), one of the CIN genes, has been implicated in oncogenic functions and drug resistance. TRIP13 is an AAA$^+$-ATPase that alters the conformation of client macromolecules and affects cellular signaling.

Five novel discoveries have laid the groundwork for the following studies. (1) TRIP13 transforms NIH3T3 fibroblasts to tumor cells and enhances tumor progression in transgenic mice. (2) Compared to normal and MGUS plasma cells, TRIP13 is highly expressed in MM cells, surviving in complete remission, and is also significantly increased in patients relapsing early after transplantation. (3) High TRIP13 expression in MM samples at diagnosis is associated with a poor prognosis in MM. (4) TRIP13 interacts with the apoptosis-inducing factor 1 (AIF1), which is related to cell apoptosis and forms a promising pharmacological tool 24. And (5) Treatment with pharmacological ascorbic acid (PAA) overcomes TRIP13-induced MM cell drug resistance and selectively kills MM cells in vitro and in vivo.

Introduction

Multiple myeloma (MM), originating from its precursors MGUS and SMM, is the second most common hematological malignancy in the United States. MM accounts for 10% of all hematological malignancy and causes over 12,000 deaths in the United States annually. MM is a cancer of plasma cells in the bone marrow associated with an overproduction in most cases of a complete or partial monoclonal (M)-protein. Monoclonal gammopathy of undetermined significance (MGUS), a MM precursor, is an asymptomatic plasma cell dyscrasia that is present in more than 3% of the general population older than age. Smoldering multiple myeloma (SMM) is another asymptomatic plasma cell disorder that carries a higher risk of progression to MM compared to MGU. The MM literature supports a role for both genetic and environmental factors in the progression of MM from its precursor states, which are present in virtually all MM patients. However, little is known about the mechanisms governing the transition of MGUS/SMM to symptomatic MM.

Dysregulation of chromosomal stability genes causes drug resistance and myeloma relapse. Drug resistance is a universal problem with current MM therapies. Although the large majority of MM patients achieve a complete remission, many patients suffer a relapse die of their disease. Drug-resistance can be categorized as de novo resistance and acquired resistance. De novo resistance is likely genetic in nature while acquired resistance likely results from a combination of cumulative mutations as a result of inadequate treatment of a genetically unstable clone, and cross-talk between MM cells and the bone marrow environment, resulting in survival and proliferation. Previous work revealed that high expression of chromosomal instability (CIN) genes (AURKA, KIF4A, CEP55, RRM2, CCNB1, CDC20, TRIP13, TOP2A, PBK and NEK2) increases cell survival and drug resistance with consequent poor outcome in MM and other cancers.

TRIP13 acts as an oncogene and is linked to sensitivity to chemotherapy and disease relapse in myeloma. TRIP13 is an AAA$^+$-ATPase protein and is upregulated in multiple types of human cancers. This enzyme contains a specific N-terminal domain (NTD) responsible for localization and substrate recognition, and one or two AAA$^+$-ATPase modules that typically assemble into a hexametric ring. It was found that TRIP13 transforms NIH3T3 fibroblasts to tumor cells and enhances tumor progression in transgenic mice. High levels of TRIP13 activates the non-homologous end joining (NHEJ) signaling pathway to repair doublestrand breaks (DSBs), thereby leading to chromosomal instability (CIN), cancer cell survival, metastasis, and enhanced drug resistance. Data indicate that compared to MGUS and SMM plasma cells TRIP13 is significantly increased in MM cells, during CR and in MM samples at relapse early after treatment. Therefore, therapeutic targeting of the TRIP13 pathway in patients with MM is very likely to be effective in preventing progression from MGUS/SMM to MM and relapse.

The experiments below were developed to determine novel therapies to sensitize high-TRIP13 myeloma cells. Firs, a genetic mouse model is used to further understand the role of TRIP13 and its signaling pathways in MM disease development and progression, and determine if TRIP13 is critical for tumorigenesis. Using a systematic TAP-MS analysis, it was identified that TRIP13 binds to AIF1. This interaction may explain why high TRIP13 increases cell survival and drug resistance in MM. Second, it is investigated whether TRIP13 sequesters AIF1 in mitochondria and/or cytosol and prevents cell apoptosis induced by AIF1 nuclear translocation. Third, the hypothesis is tested that modulation of reactive oxygen species (ROS) by utilizing PAA eliminates MM tumor cells with high levels of TRIP13. Previous work has shown that PAA has potent clinical anti-cancer pro-oxidant activity. In vitro and in vivo models have been developed to elucidate the role of TRIP13 in tumor development and progression useful for the development of a novel therapy approach directed at eradicating drug-resistant MM cells. It is very likely that our findings will not be unique to MM, but will also apply to other hematologic malignancies and solid tumors.

The candidate gene TRIP13, which is increased in MM cells and has been linked to drug resistance and poor prognosis, was discovered by comprehensive analyses of the MM genome from 1,500 clinical samples by the inventors. Further, its oncogenic function was determined by the transformation of normal fibroblasts into tumor cells. Tissue-specific TRIP13 transgenic mice have been generated that show enhanced B cell lymphoma progression (FIGS. 31A-B). To the best of our knowledge, this is the first report that TRIP13 localizes in both mitochondria and cytosol and binds to AIF1. A new genetically engineered MM mouse model, designated C.IL6/iMyc is used in the studies described herein. The model recapitulates key features of the human disease (e.g., serum para-protein, osteolytic lesions, kidney disease) and lends itself nicely to adoptive transfer of B cells. Treatment with high-dosed ascorbic acid produces oxidative stress, which breaks the interaction of TRIP13 with AIF1. This results in killing of MM cells. New technologies, such as tandem affinity purification followed by mass spectrometry (TAP-MS), RNA sequencing, chromatin immunoprecipitation (ChIP)-sequencing, advanced biochemical assays, adoptive B cell transplantation, and the FDG-PET-CT for mouse imaging, are employed in the experiments described herein.

TRIP13, a CIN gene, is linked to a poor survival in MM. Using sequential analyses of gene expression profiling (GEP) in the same patient, 56 genes were identified, the expression of which was significantly up-regulated compared to those at baseline after intensive chemotherapy and at relapse, early after transplantation. The major functional group including 10 genes with a significant negative impact on survival (Hazard ratio [HR]>=2), belongs to the well-established chromosomal instability (CIN) signature (Zhou W, Yang Y, Xia J, Wang H, Salama M E, Xiong W, et al. NEK2 induces drug resistance mainly through activation of efflux drug pumps and is associated with poor prognosis in myeloma and other cancers. Cancer Cell 2013 Jan. 14; 23(1): 48-62). Supervised clustering using the 10 CIN gene model, was applied to plasma cells from 22 healthy donors (NPC), 44 patients with MGUS, 351 patients with newly diagnosed MM, and 9 human myeloma cell lines (MMCL) (FIG. 26A). The correlation between gene expression and survival was determined by the p value and HR at the best expression signal cut-off. TRIP13 was one of the most significant genes associated with an inferior survival in unadjusted log rank tests. As shown in FIGS. 26A-C, the top quartile (25%) of MM patients with the highest TRIP13 expression had a significantly inferior event free survival and overall survival (FIGS. 26B & 26C, $p \leq 0.001$) in Total Therapy 2 (TT2) cohort.

Increased TRIP13 expression promotes myeloma cell growth and drug resistance. To test the role of TRIP13 on MM cell growth, TRIP13 was overexpressed by lentivirus-mediated TRIP13-cDNA transfection in the MM cell lines ARP1, OCI-MY5, and H929 with low baseline expression of TRIP13. The expression level of TRIP13 was verified by RT-PCR and western blot (FIG. 27A). TRIP13 overexpression significantly increased MM cell proliferation of ARP1, OCI-MY5, and H929 MM cell lines (FIG. 27B). The effects of TRIP13-knockdown on MM cell growth in vivo was next determined. ARP1 MM cells transduced with TRIP13-shRNA or scrambled vectors were injected subcutaneously into the abdomen of NOD-Rag1null mice. It was observed that tumor size was significantly smaller in the TRIP13-shRNA mice compared to those controls (FIGS. 27C & 27D). To determine whether high expression of TRIP13 increases drug resistance in MM cells, ARP1 MM cells were incubated with bortezomib and etoposide, which are widely used in MM treatment. As shown in FIG. 27E and FIG. 27F, treatment with bortezomib or etoposide induced significantly less growth inhibition in TRIP13-OE MM cells compared with EV controls ($p<0.05$).

TRIP13 is an oncogene that transforms normal fibroblasts to tumor cells. To determine whether TRIP13 functions as an oncogene, malignant cellular transformation in NIH3T3 fibroblasts was performed. NIH3T3 cells were transfected with mouse TRIP13 (mTRIP13) and empty vector (EV) and compared the formation of anchorage-independent colonies in soft agar. After 2-week culture, >20 colonies were observed in each well of the 6-well plates with mTRIP13 overexpression, while virtually no colonies were observed in wells with control cells (EV) (FIGS. 28A & 28B). Next, 2.5×105 NIH3T3 cells with mTRIP13 overexpression or empty vector were injected subcutaneously into each flank of NOD-Rag1null mice (n=5 and repeat n=3) and evaluated for tumor growth respectively. Tumor mass was palpable on Day 15~19 for mTRIP13 overexpressing cells, but no tumors were found after injection of control cells with empty vector after 26 days. Of the mice injected with mTRIP13 overexpressing cells, 6 of 8 (75%) developed tumors (FIG. 28C). These results implicate that mTRIP13 has oncogenic capabilities.

Determination of the Role of TRIP13 in Myeloma Pathogenesis.

Characterization of the role of TRIP13 in myeloma-like tumor development and progression. Recent work revealed that high expression of CIN genes, including TRIP13, induces MM cell proliferation and drug resistance. Data demonstrate that TRIP13 has an oncogenic function, such that overexpression of TRIP13 in NIH3T3 cells induces tumor transformation (FIG. 28A-C). Given that plasma cells in MM originate from terminally differentiated B cells, a lymphocyte-specific TRIP13-transgenic C57/BL6 mouse was generated in which TRIP13 expression is controlled by the LCK promoter. Although tumor formation was not observed in Tg TRIP13 mice, TRIP13 significantly promoted B cell tumor development by crossing with Eµ-Myc mice (FIGS. 30A-E), further suggesting that TRIP13 plays an oncogenic role. Therefore, it is hypothesized that high TRIP13 enhances MM development and progression.

To test this hypothesis, two approaches are used that rely on engineered over- or under-expression of RIP13 in a non-germline mouse tumor model. First, a relatively inexpensive mouse model of MM has been developed that enables rapid in vivo validation of candidate MM genes (Tompkins V S, Rosean T R, Holman C J, DeHoedt C, Olivier A K, Duncan K M, et al. Adoptive B-cell transfer mouse model of human myeloma. Leukemia 2016 April; 30(4): 962-966). The cornerstone of the method is adoptive B-cell transfer (FIG. 29A-29D). Briefly, Balb/c IL6/iMyc-double transgenic (TG) mice, which develop spontaneous plasma cell tumors (PCTs) with 100% penetrance are used as the source of mature CD45.2$^-$ B-lymphocytes that are genetically "hard wired" to undergo malignant transformation when transferred to CD45.1$^+$ hosts, where the CD45.2$^+$ cells complete neoplastic transformation and form PCTs. The donor B cells can be genetically modified in vitro by retro- or lentiviral gene transduction. The new method affords numerous scientific and practical advantages including: the use of hosts genetically deficient in key factors of the MM micro-environment (see FIG. 29F for an example); the generation of "waves" of genetically tagged (CD45.2$^+$)

PCTs in CD45.1⁺ hosts in a predictable, timely, economic fashion (note that one donor mouse suffices to reconstitute up to 30 hosts); and combination of adoptive cell transfer with integrated micro-CT imaging for studies of MM bone disease (FIG. 29E). Here, the newly developed technology is employed to evaluate the role of TRIP13 in PCT development and progression.

Generation of TRIP13-silenced and TRIP13-overexpressing C.IL6/iMyc mice. The experimental model system depicted in FIG. 29A-29F is used to evaluate the biological significance of TRIP13 in PCT development and progression at sites of myeloma-like tumors in mice. C.IL6/iMyc-TG CD45.2⁺B220⁺ B cells are transduce at age 6 weeks (~30 days earlier for detection of tumor) with a lentiviral vector that co-expresses mouse TRIP13 and luciferase (Luc): TRIP13$^{OE}$ cells. These B cells are also transduced with a lentiviral vector that co-expresses scrambled control shRNA (scrCON) or two different mouse TRIP13-targeted shRNAs (designated TRIP13$^{KD}$) and Luc. 45 CD45.1⁺ mice are reconstituted with B cells in which TRIP13 expression is overexpressed (n=15, TRIP13$^{OE}$) or undetectable (n=15 for each shRNA to TRIP13), and 15 CD45.1⁺ mice with B cells infected with scrCON virus (designated TRIP13$^{WT}$ because cells express mouse TRIP13 at wild type [WT] levels). The TRIP13$^{KD}$ mice are given doxycycline in their chow immediately after adoptive transfer to achieve early downregulation of TRIP13 in the CD45.2⁺ B cells.

Characterize cancer cells and MM progression: It has been shown that increased TRIP13 accelerates tumor development and progression in the TRIP13/Eµ-Myc mice (FIGS. 30A-E). The major goal of this experiment is to assess whether TRIP13 is critical for MM development and progression. Therefore, we will determine whether knockdown (KD) of TRIP13 in pre-malignant B cells prevents PCT formation and progression. The TRIP13$^{OE}$ and scrCON mice will serve as positive and negative controls respectively. These mice will be observed for a period of 20 months. The growth of tumors in these mice will be monitored weekly based on physical examination including body weight and health status parameters and measurement of tumor burden by detection of any serum paraprotein (M-spike) through serum protein electrophoresis combined with the F18-PET-Scan. Time to tumor onset will be recorded. A comprehensive, systematic approach to analysis of the transgene in the mice is planned. This includes a complete necropsy with particular emphasis on lymph nodes, spleen, and bone marrow. Representative tissue samples from lymph nodes, spleen and bone marrow are placed in a fixative, such as Bouin's or 10% neutral buffered formalin. Cut sections of tissues, placed in mounting medium and snap-frozen, are used for immunohistochemistry testing. A large sample of whole blood (~1 ml) is collected by heart puncture and used to measure serum protein (cytokines, chemokines) levels and to isotype paraproteins (by ELISA).

Clonal cytogenetics karyotyping and spectral karyotyping (SKY) analysis. The tumor cells from Tg mice (TRIP13$^{KD}$, TRIP13$^{OE}$, and scrCON C.IL6/iMyc mice) Re-collected and grown in culture medium RPMI1640 with 20% FBS. Cell growth Re arrested by colcemid (4 µl/ml). Metaphases from the first-passage tumor cells are examined by "chromosome painting" with the use of commercially available SKY probes for mouse (Vysis Inc). This technique serves as a screen for chromosome number (gains or losses), inversion and translocations.

Identify genomic changes between TRIP13$^{KD}$ with TRIP13$^{OE}$ and scrCON C.IL6/iMyc mice. The Illumina next generation whole genomic sequencing is used to detect genomic instability, such as mutational and copy number changes at the DNA level, induced by TRIP13 overexpression. CD138⁺ MM cells from 10-15 tumors are collected from these mice. Deeper whole-genome sequencing of tumor cells will be performed. Gene mutations, chromosome amplifications, deletions, and translocations are characterized by mapping on the mouse genome browser (UCSC genomic browser GRCm38/mm10). Specific mutation patterns, such as G=>A or C=>T, and C=>T 60, 61 that are commonly observed in human MM are examined. Further, these findings are compared with the mutation pattern and chromosome changes in human MM patient samples. This may determine TRIP13 functions in chromosomal instability (CIN). RNA-sequencing is also performed on these mouse tissues.

Identify the Mechanisms by Which TRIP13 Accelerates Tumor Development and Progression.

TRIP13 accelerates tumor development and shortens mouse survival in double Tg TRIP13/Eµ-Myc mice compared to the control Eµ-Myc mice alone (FIGS. 30A-E). However, the mechanisms by which TRIP13 exerts its oncogenic function are unknown. Pre-malignant B cells (B220⁺) have been collected from both Tg TRIP13/Eµ-Myc and Tg Eµ-Myc mice at age of 6 weeks, and RNA-seq has been performed on these two groups of B cells. As shown in FIG. 31A, more than 1,900 genes are differentially expressed between these B cells (p<0.001). The TRIP13 signaling pathways were analyzed using Gene Set Enrichment Analysis (GSEA). FIG. 31B lists the 10 most significant pathways, which distinguished B cells of the TRIP13/Eµ-Myc mice from the Eµ-Myc mice and can be targeted by commercially available inhibitors. To further define how TRIP13 functions as an oncogene, it is determined if inhibition of these pathways delays or prevents TRIP13-induced tumor development using in vitro, in vivo and primary MM samples.

TRIP13 modifies the transcriptional profiles of Eµ-Myc mice. As shown in FIG. 30B and FIGS. 32A-B, c-Myc, PRC2-EZH2, p53 and PTEN signaling pathways are significantly activated or inhibited by TRIP13. More than hundreds to thousands of genes have been identified as potential binding targets of the transcription factors (c-Myc, p53, and PTEN) or the epigenetic regulator (EZH2). It is hypothesized that TRIP13 regulates the c-Myc, EZH2, p53 and PTEN activity, which accelerates tumor onset and progression. Therefore, ChIP-sequencing is performed in pre-malignant B cells derived from Tg TRIP13/Eµ-Myc mice and from the control Eµ-Myc mice at age 6 weeks (the same for RNA-seq in the FIGS. 31A-B). Briefly, DNA fragments with an average size of 0.3-0.5 kb after cross-linking and sonication are immunoprecipitated using anti-c-Myc, -EZH2, -p53 or -PTEN antibodies or IgG as a control. The DNA fragments binding to these antibodies are identified by sequencing on an Illumina HiSeq 2500 sequencer. Combined with RNA-seq described above, the above proteins—targeted genes regulated by TRIP13 in B cell lymphoma-genesis—are identifiable.

Determination of pathways for tumorigenesis. FIG. 31B shows the 10 most significant signaling pathways by comparing pre-malignant B cells from Tg TRIP13/Eµ-Myc versus Eµ-Myc mice. To determine which pathways activated by TRIP13 play a critical role in tumorigenesis, this function is investigated from the approaches depicted in FIG. 31C.

1) Soft agar assay for colony formation in NIH3T3 cells: 1×10⁴ NIH3T3 cells transduced with control vector or murine TRIP13 (mTRIP13) and N-Ras (as the positive control) are mixed with RPMI1640 media containing 10% FBS and 0.33% agar and layered on top of the base layer of 0.5% agar in each well of 6-well plates. Half of the wells are treated with the 10 drugs listed in FIG. 31B respectively. Colony numbers are counted after approximately 2~3 weeks. All plates are imaged under microscope and overall numbers of colonies in the pictures are counted by the Image J software.

2) NIH3T3 tumor transformation in vivo: For tumorigenesis assay, the most five effective drugs related to TRIP13 signaling pathways identified by the above-soft agar assays are tested. $2.5 \times 10^5$ NIH/3T3 cells that co-express mTRIP13 and luciferase (Luc): TRIP13$^{OE}$ cells or the control cells with Luc will be injected subcutaneously into each side of the NOD-Rag1$^{null}$ mice dorsa. Each group consists of 3 mice (total mice n=30) including 6 tumors. Tumor incidence and the number of tumor nodules from each group are counted and compared to each other. Tumor burden is measured by Bioluminescence Assay. Tumor length and width will also be gauged, and tumor volume will be calculated as (length× width)×0.5. For each time point, results will be presented as the mean tumor volume±SD for the indicated mice.

3) Tg TRIP13/Eμ-Myc and Eμ-Myc mice: Because this is a faithful genetic model for TRIP13 signaling, three drugs identified above from NIH3T3 tumor transformation in vivo are tested in this model. Both Tg TRIP13/Eμ-Myc or Eμ-Myc mice at age 50 days are used for this study. 24 Tg TRIP13/Eμ-Myc mice and 24 Eμ-Myc mice are randomly assigned to one of four treatment groups (three drugs and one control) with equal representation of mouse gender. Blocking the pathways by the inhibitors should delay the tumor formation in the Tg TRIP13/Eμ-Myc mice and show less impact in the Eμ-Myc mice.

4) Plasma cell tumor (PCT) in C.IL6/iMyc mice: Because this is a genetic MM mouse model, the two most effective drugs are tested as defined above. Similar to the description described above in FIGS. 29A-F, CD45.2$^+$ B220$^+$ B cells from Tg C.IL6/iMyc at age 6 weeks are reconstituted in CD45.1$^+$ mice. Six mice are required for each group and, a total of 18 mice are used for the two drugs and a control.

5) Expression and activity in MGUS, SMM, MM at diagnosis, and relapsed MM: Finally, the most two most important pathways defined above are evaluated in different stages of primary plasma cell tumor samples. Ten samples of each stage of MGUS, SMM, newly diagnosed MM, and relapsed MM are included in this study. The targeted gene or these two signaling pathways targeted are evaluated by qRT-PCR, western blotting, ELISA, and the molecular assays to measure mRNA and protein levels, protein modification, cellular localization, Cdk activity, kinase activity, and ubiquitination activity, etc.

Preliminary data showed that increased TRIP13 enhances B lymphomagenesis resulting in a shorter survival in Tg TRIP13/Eμ-Myc mice. Importantly, past experience evaluating the collaboration of other genes (e.g., Bcl2 and IL-6) with c-Myc in mouse B-cell and PCT development suggests that enforced expression of mouse TRIP13 accelerates C.IL6/iMyc-dependent tumors. It is predicted that compared to TRIP13 normal B cells, TRIP13OE B cells undergo malignant transformation more rapidly and give rise to more aggressive disease.

Characterize Molecular Mechanisms of TRIP13-Mediated Myeloma Chemoresistance.

To define the molecular mechanism by which TRIP13 promotes drug resistance and cell survival, the TAP-MS analysis was performed to identify the interacting partners of TRIP13. Interestingly, it was found and confirmed that TRIP13 binds to the apoptosis-inducing factor 1(AIF1). Although AIF1 was considered to mainly localize in mitochondria, it was further discovered that TRIP13 localizes in both cytoplasm (main) and mitochondria, and high TRIP13 decreases nuclear AIF1 protein (FIGS. 33A-E). AIF1 is a mitochondrial FAD-dependent oxidoreductase that plays a vital role in oxidative phosphorylation (OXPHOS) and redox metabolism in normal and cancer cells. AIF1 was originally discovered as an intermembrane space (IMS) component of mitochondria and characterized as a pro-apoptotic gene. The pro-apoptotic AIF1 or truncated AIF1 (tAIF) is cleaved from the full-length AIF1 by calpains and/or cathepsins after a caspase independent cell death insult. tAIF moves from the mitochondria to the cytoplasm and then to the nucleus, where it initiates caspase-independent cell apoptosis. Therefore, it is hypothesized that the interaction of TRIP13 with AIF1 prevents AIF1 nuclear translocation resulting in decreased myeloma cell apoptosis. TRIP13 shares a frequently observed AAA$^+$ ATPase architecture (FIG. 34).

Evaluate the Role of Interaction Between TRIP13 and AIF1 in MM Cell Drug Resistance.

Structural domains of TRIP13 for interacting with AIF1. TRIP13 contains a common AAA+ ATPase domain at the 3' and conserved Walker A & B motifs. The ATPase domain is required for diverse activities of AAAATPase proteins and the Walker A & B motifs are required for ATP-binding activity. Using site-directed mutagenesis, the following TRIP13 mutants are generated (FIG. 34): G184A (TRIP13$^{G184A}$), mutation localized in the Walker A motif; W221A (TRIP13$^{W221A}$), a mutant that has been previously described showing higher Kcat than WT TRIP13; E253Q (TRIP13$^{E253Q}$), a mutant that will not be able to hydrolase ATP; R385A (TRIP13$^{R385A}$), a mutant unable to bind nucleotide. Also, a D293-312 deletion mutant is generated in which the conserved ATPase domain (TRIP13$^{\Delta293-312}$) has been deleted. All the mutants are tagged with HA. HEK293T and MM cell lines ARP1 and OCI-MY5 are transduced with different constructs expressing with the HA-TRIP13$^{WT}$ or HA-TRIP13$^{G184A}$, HA-TRIP13$^{W221A}$, or HA-TRIP13$^{E253Q}$, HA-TRIP13$^{R385A}$, and HA-TRIP13$^{\Delta293-312}$. HA-Tag antibody is used to pull down TRIP13 and its binding proteins. Western blot is used to identify which TRIP13 domain binds to AIF1. The localization of each mutant is determined by immunofluorescence using HA and MytoTracker for mitochondrial localization.

Does TRIP13 bind directly to AIF1 and affect sensitivity to chemotherapy? It has been shown that AIF1 binds to TRIP13 protein and TRIP13 localizes in both mitochondria and cytoplasm of MM cells (FIGS. 33A-33C). To determine whether the interaction between AIF1 and TRIP13 is direct, in vitro GST pull down assays are performed. The GST-tagged TRIP13 is purified from bacteria using glutathione beads. The purified GSTTRIP13 is incubated with recombinant AIF1 protein. The glutathione beads are washed and western blotting analysis using the AIF1 antibody to detect whether AIF1 binds to TRIP13 protein directly.

To investigate which domain of TRIP13 is required to interact with AIF1 using GST-pull down assay, different GST-tagged mutants of TRIP13 defined above are purified from bacteria and incubated with full length recombinant AIF1 in vitro. The positive interacting domain once identified are deleted from the full length TRIP13 to generate a dominant-negative mutant ΔTRIP13 that should no longer be capable to interact with AIF1. WT-TRIP13 or ΔTRIP13 is then introduced to MM cell lines ARP1, H929 and OCI-MY5 with inducible shRNA against 3'-UTR of endogenous TRIP13. The endogenous TRIP13 is depleted by doxycycline administration. Because it is expected that TRIP13 promotes cancer cell survival and drug resistance through binding with AIF1, cell survival and drug resistance induced by ΔTRIP13 relative to the WT-TRIP13 is compared. (1) To assay the changes in G1-S progression, cells are synchronized in M phase by nocodazole or in G0 by serum starvation, released into cycle by drug removal, re-plated into media with serum, and assayed at 2 hr intervals for rates of S phase entry (via flow analysis of DNA content and BrdU positivity). (2) DNA repair is assayed by treatment of cells with a pulse of bleomycin to cause double stranded DNA breaks. Measurement of these breaks by an alkaline "comet" assay, in which single cells are subjected to electrophoresis and unrepaired DNA breaks, are visualized as a "tail". Cell survival after DNA damage is determined by a colony assay. (3) Notably, the IC50 for each drug including bortezomib, melphalan, lenalidomide and dexamethasone is determined in order to test if sensitivity is altered by changes in TRIP13 and AIF1 status. Drug resistance is also evaluated by soft agar clonogenic assays described in the FIGS. 28A-C. (4) Cell viability is assayed using Resazurin (Life Technologies), proliferation using colorimetric BrdU detection (Roche) and growth in soft agar. The dependence of AIF1 in TRIP13-induced DNA repair, cell growth and drug resistance is thereby determined in MM cells.

Does TRIP13 neutralize AIF1 in myeloma cells? AIF1-mediated caspase-independent cell apoptosis depends on the mitochondrial→cytosol→nuclear translocation. Data in FIGS. 33D and 33E show that overexpression of TRIP13 decreases nuclear AIF1 protein. To further determine if high TRIP13 inhibits AIF1-mediated apoptosis, the subcellular localization of AIF1 after an apoptotic insult is examined. The above ARP1 and OCI-MY5 transfected with WT-TRIP13 or ΔTRIP13 (no binding domain with AIF1) are transduced with AIF1-GFP. These MM cells are treated for 90 min with N-methyl-N-nitroso-N'-nitroguanidine (MNNG) 500 mM 92, which is a carcinogen and mutagen and can trigger AIF1 to be released from mitochondria and move to the nucleus. The relative mitochondria/cytoplasm/nucleus distribution of AIF1 is evaluated by both immunofluorescence confocal microscopy, cellular fractionation assays, and transmission electron microscopy (TEM) as previously described (FIGS. 36A-C) (Xia J, Xu H, Zhang X, Allamargot C, Coleman K L, Nessler R, et al. Multiple Myeloma Tumor Cells are Selectively Killed by Pharmacologically-dosed Ascorbic Acid. EBioMedicine 2017 Feb. 16).

Define TRIP13 Signaling Pathways Using Clinical Samples and Genetic Mouse Models.

Biological samples. CD138+ MM cells from patient samples are isolated using human anti-CD138+ antibody (FIG. 35).

Clinical relevance of TRIP13 with AIF1 in serial MM samples at diagnosis, remission and relapse. To determine the relevance of the interaction between TRIP13 with AIF1 in human MM disease, their expression and localization in human primary sequential MM samples at the protein level is evaluated. As we show in FIGS. 36A-C, MM cells collected in remission (FIG. 36B) and relapse (FIG. 36A) show higher expression of TRIP13 than those at diagnosis by GEP. In this study, about 30 serial MM biopsies collected at diagnosis, in remission (only samples can be isolated enough MM cells) and relapse (HawkIRB protocol 201302833; arrows in FIG. 35) are used. Immunohistochemistry on bone marrow biopsies is performed using anti-TRIP13, anti-AIF1, and anti-CD138 Abs in these serial MM samples. It has been shown that AIF1 is increased in the cytosol and decreased in the nucleus of TRIP13-OE MM cells (FIGS. 33D & 33E), suggesting a mechanism that TRIP13 sequesters AIF1 in the mitochondria or cytosol to block its apoptosis function. Protein levels and subcellular localization of TRIP13 and AIF1 are also analyzed by cellular fractionation and TEM on CD138+ primary MM cells sorted by flow cytometry. Western blots and/or TEM are performed on a smaller number of selected tumors: (i) that sufficiently represent each patient group studied, and (ii) for which there is an adequate amount of isolated protein available. The correlations between TRIP13 and AIF1 expression and localization as well as with clinical stages and outcome are analyzed.

Dissect the molecular regulation networks of TRIP13 using patient samples and genetic mouse models. Two approaches are used: 1) Microarray data analysis of clinical samples: As we showed in FIGS. 26 and 36, GEPs have been generated from 22 normal plasma cells, 44 MGUSs, 550 newly diagnosed MMs, 59 from different treatment stages including partial and complete remission, and 90 relapsed MM samples. The expression correlation of TRIP13 and its signaling pathway-related transcriptome is analyzed using the transcriptome data; Correlation and clustering methods are applied to identify TRIP13 targets and regulatory networks. 2) RNA sequencing on genetic mouse tissues: RNA-sequencing has been performed in pre-malignant B cells between Tg TRIP13/Eμ-Myc and Eμ-Myc mice (FIGS. 32A-B). To further identify and confirm upstream regulators or downstream effectors of TRIP13 in MM, deep RNA-sequencing is also performed to detect differentially expressed genes between tumors derived from TRIP13$^{KD}$, TRIP13$^{OE}$, and scrCON C.IL6/iMyc mice (see discussion above). About 10 samples from each group are collected. Briefly, CD138+ MM cells are sorted out and 10,000~30,000 sorted cells will be used to extract total RNA followed by cDNA synthesis/amplification using the Clontech SMARTer kit for RNA-Seq experiment. Deep sequencing will be performed using an Illumina HiSeq 2500 sequencer. Each sample is sequenced to a depth of 100 million read pairs to ensure sufficient depth for accurate detection of alternative transcripts. Briefly, four analysis programs are used: (i) reads that pass quality control are mapped to the genome by STAR; (ii) featureCounts are used to estimate transcript expression level; and (iii) the Deseq2 is used to determine differential expression; and (iv) enriched pathways are analyzed by GSEA and Enrichr. Integrative data analyses are performed on these both microarray data and the deep-sequencing dataset.

Structure function studies are critical to identifying the TRIP13 intermolecular interactions important for MM disease biology. It is anticipated that specific residues or domains of TRIP13 will be identified that bind to AIF1 and mediate chemotherapy resistance. It is anticipated that wild-type TRIP13 will confer resistance to bortezomib, melphalan, lenalidomide and dexamethasone treatment but that the mutant lacking binding to AIF1 will not. In human primary MM samples, it is predicted that TRIP13 will increase in remission and relapsed MM samples at the protein level, but will negatively correlate with nuclear AIF1 expression and patient outcome. Integrative analyses of RNA-sequencing data from TRIP13KD, TRIP13OE, and scrCON C.IL6/iMyc mice and microarray data from more than 1500 patient samples with clinical information, should identify novel downstream signaling pathways and networks that are associated with TRIP13-induced drug resistance in MM.

Develop Novel Therapies to Target High-TRIP13 Myeloma Cells.

TRIP13 encodes an AAA$^+$-ATPase enzyme but has received little attention in cancer including MM. Studies have shown that TRIP13 localizes in both mitochondria and cytosol and interacts with AIF1 directly (FIGS. 33A-E). It was recently reported that pharmacologically-dosed ascorbic acid (PAA), in the presence of iron, leads to the formation of highly reactive oxygen species (ROS) resulting in AIF1 cleavage and translocation from the mitochondria to the nucleus, causing cell death (FIGS. 37A-G). TRIP13 upregulates the iron importer: Transferrin Receptor (TFRC) and downregulates the iron exporter: ferroportin (FPN1) resulting in increased ferritin (a known marker of cytosolic iron) in MM cells overexpressing TRIP13 (FIG. 38A-38C). Importantly, PAA induces AIF1 nuclear translocation not only in TRIP13$^N$ MM cells but also in TRIP13$^{OE}$ MM cells, whereas Bortezomib treatment does not increase AIF1 nuclear localization (FIG. 38D). Therefore, it is hypothesized that TRIP13$^{high}$ cells are sensitive to PAA treatment by disrupting its interaction with AIF1 leading to increased apoptosis and are able to overcome TRIP13-induced drug resistance. As described in FIG. 39, TRIP13 cells have increased cytosolic ferritin leading to high levels of redox-active iron. In TRIP13-OE cells, PAA oxidizes by reacting with iron. PAA autoxidation generates cellular oxidative damage leading to AIF1 cleavage in the mitochondria with subsequently translocation to the nucleus. AIF1 nuclear translocation induces apoptosis and cell death. Based on this model, it is hypothesized that PAA treatment is a valuable therapeutic approach to overcome TRIP13-mediated drug-resistance in vivo.

Does pharmacological ascorbic acid (PAA) disrupt the TRIP13-AIF1 association and lead to nuclear accumulation of AIF1? AIF1-mediated caspase-independent cell apoptosis is the consequence of AIF1 translocation from the mitochondria to the nucleus. Preliminary data show that PAA induces MM cell necrosis and apoptosis and is partially dependent on AIF1 cleavage and nuclear translocation (FIGS. 37E & 37G). To further determine how PAA overcomes TRIP13-induced drug resistance in MM cells, the MM cell lines ARP1, H929 and OCI-MY5 transfected with WT-TRIP13 or ΔTRIP13 (lacking binding domain with AIF1) are treated with PAA at 1, 2, 4, and 8 mM for 60 min and cultured for another 16 h. The relative mitochondria/cytoplasm/nuclei distribution of AIF1 is evaluated by immunofluorescence confocal microscopy, cellular fractionation assays, and TEM. The AIF1 cleavage is detected by western blot. Chromatolysis is also evaluated in PAA treated MM cells as described above. FIG. 39 summarizes the PAA action in killing MM cells with high TRIP13 expression. Based on this data, it is tested if PAA by targeting TRIP13/AIF1 interaction overcomes TRIP13-induced drug resistance. Bortezomib is used as a negative control in these experiments.

Investigate therapeutic effects of PAA in doubly Tg TRIP13/Eμ-Myc mice, which have increased TRIP13 expression and normal immune system. Double-transgenic TRIP13/Eμ-Myc mice have recently been generated that develop B cell lymphoma in the presence of a normal immune system (FIGS. 30A-E). To investigate the effects of PAA on established TRIP13/Eμ-Myc lymphoma, paired TRIP13$^{OE}$/TRIP13$^N$ B lymphoma autografts, derived from two genetic transgenic mouse models are used: TRIP13/Eμ-Myc and Eμ-Myc. The mTORC1 inhibitor Everolimus (RAD001) is used as a control, which showed a good efficacy in inhibiting tumor development in the Eμ-Myc mice. Each group will include nine mice with equal representation of mouse gender. For lymphoma transplantation from either Tg TRIP13/Eμ-Myc or Eμ-Myc mice, a total of $2.5 \times 10^5$ cryopreserved cells are thawed and resuspended in sterile PBS before being introduced into syngeneic recipient mice by tail vein injection for each mouse. 36 mice are treated with PAA (4 mg/kg, i.p., twice a week for 4 weeks) or Everolimus (5 mg/kg, oral gavage, once/week for 4 weeks) or combination of PAA with Everolimus or no treatment. In addition to FDG-PET scanning, mice are closely monitored for signs of tumor development. This entails weekly determination of body weight, health status parameters, and lymphadenopathy by palpation. Peripheral blood lymphocytosis is monitored by serial blood tests weekly. At necropsy, a representative set of tissues are harvested for histopathology, immunological, molecular genetic and genomic analyses. The TRIP13 signaling pathways are also evaluated by qRT-PCR, western blot and the molecular assays described above to assess mRNA and protein levels in tumor cells with or without PAA treatment.

Determination of the therapeutic efficacy of PAA by analyzing primary MM cells at diagnosis and in relapse in the NOD-Rag1null –hu mouse model. The efficacy of PAA in treating human primary MM cells collected at diagnosis and at relapse using the NOD-Rag1$^{null}$ –hu mouse model is assessed.

Human fetal bones are obtained from Advanced Bioscience Resources. Briefly, human fetal long bones (tibias and femurs) from 18- to 21-week gestational fetuses are cut into two 10-mm pieces, and implanted subcutaneously, on either left or right side of the dorsum of NOD-Rag1null mice (one bone/mouse). Primary MM cells are isolated from MM patients at diagnosis (low TRIP13) and in relapse (high TRIP13) using CD138$^+$ magnetic beads or flow cytometry. The level of TRIP13 is assessed in each of these samples as outlined above. At 6 to 8 weeks after implantation of bone, about $1.5 \sim 2 \times 10^6$ MM cells (CD138$^+$) are injected directly into the marrow cavity of each bone implanted into the NOD-Rag1$^{null}$ –hu host. PAA is combined with melphalan in this study, because the preliminary data in a MM cell line and other murine models showed clearly that a synergistic effect when PAA is combined with melphalan at a lower dose (FIGS. 37F & 37G). Four treatment combinations for each sample are the following: untreated, PAA, melphalan, and PAA+melphalan. It is possible to purify $10 \times 10^6$ MM cells from a newly diagnosed MM sample or from a relapsed MM patient, respectively. Therefore, one sample is sufficient to cover the four combinations outlined above. Drug concentration of the PAA is described above, and melphalan dosing is 3 mg/kg (twice a week, i.p., on the same days as PAA administration for 4 weeks). This study utilizes nine paired MM samples obtained at diagnosis and in relapse. A total of 72 mice with equal representation of mouse gender within each treatment group at each time point are required. Tumor growth is monitored by measuring human serum free light chains and M protein. Mice survival and time to tumor recurrence time are compared among the above outlined groups. M cell apoptosis is evaluated by double staining with a CD138$^+$ antibody and the deoxyuridine triphosphate nick-end labeling (TUNEL) assay in the fixed fetal bone sections. The number and size of bone lesions are determined by X-ray and micro-CT. TRIP13 expression and activity are analyzed as described above.

Statistical Analyses: Statistical analysis is performed to compare treatment groups within each experiment with respect to the proportion of mice that develop B cell lymphomas, MM or relapse by the end of the study. Power is estimated based on pairwise treatment group comparisons performed with a simpler one-sided Fisher's exact test at a single time point. Without treatment, the rate of tumor development or relapse is conservatively estimated to be 95%. Accordingly, the use of nine mice per group achieves 80% power to detect a difference of at least 60% (95% vs 35%) between the untreated and an active treatment group at the 5% significance level. In addition, time to relapse or time to B lymphoma is explored in a full analysis comparing treatment groups. Survival curves are constructed using the Kaplan-Meier method and compared between treatment groups using the log-rank test. It is anticipated that PAA should break the interaction of TRIP13 with AIF1 and induce AIF1 nuclear translocation in TRIP13-OE MM cells as depicted in FIG. 39. It is predicted that it is possible to define the best way to prevent TRIP13-mediated B cell lymphoma development and/or MM disease progression. Considering that transgenic TRIP13/Eµ-Myc mice provide one of the most faithful experimental model systems of TRIP13 signaling in mammalian cells currently available, it is expected to gain insight into TRIP13-dependent tumor inhibition. It is also anticipated that PAA delays or prevents development of B cell lymphoma in Tg TRIP13/Eµ-Myc mice. It is predicted that the PAA kills primary MM cells especially when using relapsed MM cells, which contain high cellular iron. The combination with PAA should result in lower dosage of commonly used drugs, such as melphalan, without losing efficacy in the NOD-Rag1$^{null}$-hu mice model when compared to high-dose melphalan by itself.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a hyperproliferative disorder associated with high intracellular iron comprising administering pharmacological ascorbic acid or a pharmaceutically acceptable salt thereof and melphalan, wherein the pharmacological ascorbic acid is administered at a dose of about 15 g-100 g, wherein the hyperproliferative disorder is smoldering multiple myeloma.

2. The method of claim 1, wherein the melphalan is administered at a dosage of about 2 mg/m$^2$ to 200 mg/m$^2$.

3. The method of claim 1, wherein the pharmacological ascorbic acid and the melphalan are administered simultaneously or sequentially.

4. The method of claim 1, further comprising administering a proteasome inhibitor.

5. The method of claim 4, wherein the pharmacological ascorbic acid and the proteasome inhibitor are administered simultaneously or sequentially.

6. The method of claim 1, further comprising administering an anti-cancer therapy.

7. The method of claim 6, wherein the anti-cancer therapy is immunotherapy or biologic therapy.

8. The method of claim 1, wherein the melphalan is administered at a dosage of about 50 mg/m$^2$ and 100 mg/m$^2$.

* * * * *